(12) United States Patent
Nagarajan et al.

(10) Patent No.: US 9,757,254 B2
(45) Date of Patent: Sep. 12, 2017

(54) INTEGRAL ADMITTANCE SHAPING FOR AN EXOSKELETON CONTROL DESIGN FRAMEWORK

(71) Applicant: Honda Motor Co., Ltd., Minato-ku, Tokyo (JP)

(72) Inventors: Umashankar Nagarajan, Sunnyvale, CA (US); Gabriel Aguirre-Ollinger, Chatswood (AU); Ambarish Goswami, Fremont, CA (US)

(73) Assignee: HONDA MOTOR CO., LTD., Tokyo (JP)

( * ) Notice: Subject to any disclaimer, the term of this patent is extended or adjusted under 35 U.S.C. 154(b) by 79 days.

(21) Appl. No.: 14/823,655

(22) Filed: Aug. 11, 2015

(65) Prior Publication Data

US 2016/0067061 A1    Mar. 10, 2016

Related U.S. Application Data

(60) Provisional application No. 62/037,773, filed on Aug. 15, 2014.

(51) Int. Cl.
| | | |
|---|---|---|
| *B25J 9/16* | (2006.01) | |
| *A63B 23/035* | (2006.01) | |
| *A61F 2/70* | (2006.01) | |
| *B25J 9/00* | (2006.01) | |

(52) U.S. Cl.
CPC ............... *A61F 2/70* (2013.01); *B25J 9/0006* (2013.01)

(58) Field of Classification Search
CPC combination set(s) only.
See application file for complete search history.

(56) References Cited

U.S. PATENT DOCUMENTS

| | | | |
|---|---|---|---|
| 7,217,247 B2 * | 5/2007 | Dariush | A61H 1/00 600/595 |
| 7,390,309 B2 * | 6/2008 | Dariush | A61H 1/00 601/35 |
| 7,398,255 B2 * | 7/2008 | Lauer | A61B 5/0488 623/24 |
| 7,553,266 B2 * | 6/2009 | Abdoli-Eramaki | A61F 5/026 482/124 |
| 7,650,204 B2 * | 1/2010 | Dariush | A61H 3/008 600/587 |

(Continued)

FOREIGN PATENT DOCUMENTS

| | | |
|---|---|---|
| WO | WO2013086035 | 6/2013 |
| WO | WO2013142777 | 9/2013 |

(Continued)

OTHER PUBLICATIONS

A. M. Dollar and H. Herr, "Lower extremity exoskeletons and active orthoses: Challenges and state-of-the-art," IEEE Trans. Robotics, vol. 24, No. 1, pp. 144-158, 2008.

(Continued)

*Primary Examiner* — Jonathan L Sample
(74) *Attorney, Agent, or Firm* — Arent Fox LLP

(57) ABSTRACT

An assistive exoskeleton control system has a controller generating a positive assistance by shaping a closed loop integral admittance of a coupled human exoskeleton system to a desired assistance ratio $A_d$ by modifying a control transfer function using a cut-off frequency of a low pass filter.

19 Claims, 28 Drawing Sheets

(56) References Cited

U.S. PATENT DOCUMENTS

| | | | |
|---|---|---|---|
| 7,774,177 B2* | 8/2010 | Dariush | B25J 9/0006 600/587 |
| 7,901,368 B2* | 3/2011 | Flaherty | A61H 1/0255 601/33 |
| 8,082,062 B2* | 12/2011 | Dariush | B25J 9/0006 700/245 |
| 8,562,691 B2* | 10/2013 | Endo | G09B 19/0038 623/24 |
| 2002/0150302 A1* | 10/2002 | McCarthy | G06T 9/00 382/254 |
| 2003/0120183 A1 | 6/2003 | Simmons | |
| 2004/0143364 A1* | 7/2004 | Colgate | B66D 3/18 700/213 |
| 2006/0211956 A1* | 9/2006 | Sankai | A61B 5/04888 601/5 |
| 2006/0247904 A1 | 11/2006 | Dariush | |
| 2006/0293791 A1* | 12/2006 | Dariush | B25J 9/0006 700/245 |
| 2007/0016116 A1 | 1/2007 | Reinkensmeyer et al. | |
| 2007/0056592 A1 | 3/2007 | Angold et al. | |
| 2007/0123997 A1* | 5/2007 | Herr | A61F 2/60 623/27 |
| 2008/0009771 A1* | 1/2008 | Perry | B25J 9/0006 600/587 |
| 2008/0188907 A1* | 8/2008 | Aguirre-Ollinger | A61H 1/0237 607/48 |
| 2009/0036815 A1* | 2/2009 | Ido | A61H 1/0237 602/23 |
| 2009/0048686 A1* | 2/2009 | Ikeuchi | A61H 3/008 623/27 |
| 2009/0227925 A1* | 9/2009 | McBean | A61F 5/0127 602/16 |
| 2009/0255531 A1* | 10/2009 | Johnson | A61F 5/24 128/99.1 |
| 2009/0292369 A1* | 11/2009 | Kazerooni | A61H 3/00 623/27 |
| 2010/0010639 A1* | 1/2010 | Ikeuchi | A61H 3/008 623/24 |
| 2010/0256537 A1* | 10/2010 | Menga | B25J 9/0006 601/34 |
| 2010/0256538 A1* | 10/2010 | Ikeuchi | B25J 9/0006 601/35 |
| 2011/0105966 A1 | 5/2011 | Kazerooni et al. | |
| 2011/0256983 A1 | 10/2011 | Malack et al. | |
| 2011/0266323 A1* | 11/2011 | Kazerooni | B25J 9/0006 224/575 |
| 2012/0156661 A1 | 6/2012 | Smith et al. | |
| 2012/0165158 A1 | 6/2012 | Ren et al. | |
| 2012/0259259 A1* | 10/2012 | Chugunov | A61F 5/0102 602/16 |
| 2012/0259431 A1* | 10/2012 | Han | A61F 5/0125 623/24 |
| 2013/0158445 A1* | 6/2013 | Kazerooni | A61H 3/00 601/35 |
| 2013/0253385 A1* | 9/2013 | Goffer | A61H 1/024 601/35 |
| 2013/0289452 A1 | 10/2013 | Smith et al. | |
| 2014/0100492 A1* | 4/2014 | Nagasaka | A61H 3/061 601/34 |
| 2014/0121573 A1* | 5/2014 | Kazerooni | A61F 5/02 601/23 |
| 2014/0221894 A1* | 8/2014 | Nagasaka | A61H 3/00 602/23 |
| 2014/0277739 A1* | 9/2014 | Kornbluh | B25J 9/0006 700/260 |
| 2015/0081036 A1* | 3/2015 | Nakanishi | A61H 1/024 623/24 |
| 2015/0173993 A1* | 6/2015 | Walsh | A61H 1/024 414/4 |
| 2015/0366739 A1* | 12/2015 | Endo | A61H 3/00 482/4 |

FOREIGN PATENT DOCUMENTS

| | | |
|---|---|---|
| WO | WO2013188510 | 12/2013 |
| WO | WO2014057410 | 4/2014 |
| WO | WO2014109799 | 7/2014 |

OTHER PUBLICATIONS

D. P. Ferris, "The exoskeletons are here," Journal of Neuroengineering and Rehabilitation, vol. 6, No. 17, pp. 1-3, 2009.

R. A. R. C. Gopura, K. Kiguchi, and D. S. V. Bandara, "A brief review on upper extremity robotic exoskeleton systems," in Proc. IEEE Int. Conf. Industrial and Information Systems (ICIIS), 2011, pp. 346-351.

N. G. Tsagarakis and D. G. Caldwell, "Development and control of a 'soft-actuated' exoskeleton for use in physiotherapy and training," Autonomous Robots, vol. 15, No. 1, pp. 21-23, 2003.

A. Gupta and M. K. O'Malley, "Design of a haptic arm exoskeleton for training and rehabilitation," IEEE/ASME Trans. Mechatronics, vol. 11, No. 3, pp. 280-289, 2006.

A. U. Pehlivan, O. Celik, and M. K. O'Malley, "Mechanical design of a distal arm exoskeleton for stroke and spinal cord injury rehabilitation," in Proc. IEEE Int'l Conf. Rehabilitation Robotics, 2011.

T. Koyama, I. Yamano, K. Takemura, and T. Maeno, "Multifingered exoskeleton haptic device using passive force feedback for dextrous teleoperation," in Proc. IEEE/RSJ Int. Conf. Intelligent Robots and Systems (IROS), 2002, pp. 2905-2910.

A. Frisoli, F. Rocchi, S. Marcheschi, A. Dettori, F. Salsedo, and M. Bergamasco, "A new force-feedback arm exoskeleton for haptic interaction in virtual environments," in Proc. World Haptics Conf., IEEE Computer Society, 2005, pp. 195-201.

H. Kawamoto and Y. Sankai, "Power assist system hal-3 for gait disorder person," in Proc. Int. Conf. Comput. Helping People Special Needs (ICCHP), 2002, pp. 196-203.

H. Kazerooni and R. Steger, "Berkeley lower extremity exoskeleton," ASME J. Dyn. Syst., Meas., Control, vol. 128, pp. 14-25, 2006.

G. T. Huang, "Wearable robots," Technol. Rev., pp. 70-73, Jul./Aug. 2004.

J. E. Pratt, B. T. Krupp, C. J. Morse, and S. H. Collins, "The RoboKnee: An exoskeleton for enhancing strength and endurance during walking," in Proc. IEEE Int. Conf. Robotics and Automation (ICRA), 2004, pp. 2430-2435.

C. J. Walsh, K. Endo, and H. Herr, "A quasi-passive leg exoskeleton for load-carrying augmentation," Int. J. Humanoid Robotics, vol. 4, No. 3, pp. 487-506, 2007.

K. Kiguchi, K. Iwami, M. Yasuda, K. Watanabe, and T. Fukuda, "An exoskeletal robot for human shoulder joint motion assist," EEE/ASME Trans. Mechatronics, vol. 8, No. 1, pp. 125-135, 2003.

J. C. Perry, J. Rosen, and S. Burns, "Upper-limb powered exoskeleton design," IEEE/ASME Trans. Mechatronics, vol. 12, No. 4, pp. 408-417,2007.

R. A. R. C. Gopura and K. Kiguchi, "SUEFUL-7: A 7-dof upper limb exoskeleton robot with muscle-model-oriented emg-based control," in Proc. IEEE/RSJ Int. Conf. Intelligent Robots and Systems (IROS), 2009, pp. 1126-1131.

S. Marcheschi, F. Salsedo, and M. Bergamasco, "Body Extender: Whole body exoskeleton for human power augmentation," in Proc. IEEE Int. Conf. Robotics and Automation (ICRA), 2011, pp. 611-616.

R. Versluys, G. Lenaerts, M. V. Damme, I. Jonkers, A. Desomer, B. Vanderborght, L. Peeraer, G. V. der Perre, and D. Lefeber, "Successful preliminary walking experiments on a transtibial amputee fitted with a powered prosthesis," Prosthetics and Orthotics International, vol. 33, No. 4, pp. 368-377, 2009.

J. K. Hitt, T. G. Sugar, M. Holgate, and R. Bellman, "An active foot-ankle prosthesis with biomechanical energy regeneration," Journal of Medical Devices, vol. 4, No. 1, p. 011003011011, 2010.

H. M. Herr and A. M. Grabowski, "Bionic ankle-foot prosthesis normalizes walking gait for persons with leg amputation," Proc. Biol. Sci., The Royal Society, vol. 279, No. 1728, pp. 457-464, 2012.

(56) References Cited

OTHER PUBLICATIONS

K. Suzuki, G. Mito, H. Kawamoto, Y. Hasegawa, and Y. Sankai, "Intention-based walking support for paraplegia patients with robot suit hal," Advanced Robot., vol. 21, pp. 1441-1469, 2007.
A. Tsukahara, R. Kawanishi, Y. Hasegawa, and Y. Sankai, "Sit-to-stand and stand-to-sit transfer support for complete paraplegic patients with robot suit hal," Advanced Robot., vol. 24, pp. 1615-1638, 2010.
R. Farris, H. Quintero, and M. Goldfarb, "Preliminary evaluation of a powered lower limb orthosis to aid walking in paraplegic individuals," IEEE Trans. Neural Syst. Rehabil. Eng., vol. 19, No. 6, pp. 652-659, 2011.
D. Ferris, G. Sawicki, and M. Daley, "A physiologist's perspective on robotic exoskeletons for human locomotion," Int. J. Humanoid Robots, vol. 4, No. 3, pp. 507-528, 2007.
D. P. Ferris, J. M. Czerniecki, and B. Hannaford, "An ankle-foot orthosis powered by artificial pneumatic muscles," J. Appl. Biomech., vol. 21, No. 2, pp. 189-197, 2005.
G. S. Sawicki and D. P. Ferris, "Mechanics and energetics of level walking with powered ankle exoskeletons," J. Exp. Biol., vol. 211, No. Pt. 9, pp. 1402-1413, 2008.
P. Malcolm, W. Derave, S. Galle, and D. D. Clercq, "A simple exoskele-ton that assists plantarflexion can reduce the metabolic cost of human walking," PLoS One, vol. 8, No. 2, p. e56137, 2013.
A. M. Grabowski and H. M. Herr, "Leg exoskeleton reduces the metabolic cost of human hopping," J. Appl. Physiol., vol. 107, No. 3, pp. 670-678, 2009.
D. J. Farris and G. S. Sawicki, "Linking the mechanics and energetics of hopping with elastic ankle exoskeletons," J. Appl. Physiol., vol. 113, No. 12, pp. 1862-1872, 2012.
L. M. Mooney, E. J. Rouse, and H. M. Herr, "Autonomous exoskeleton reduces metabolic cost of human walking during load carriage," Journal of Neuroengineering and Rehabilitation, vol. 11, No. 80, 2014.
N. Hogan and B. S, O, Impedance and Interaction Control, Robotics and Automation Handbook. CRC Press, LLC., 2005, ch. 19.
U. Nagarajan, G. A.-Ollinger, and A. Goswami, "Defining assistance: A linear systems perspective," IEEE Trans. Robotics (In Submission), 2014.
S. P. Buerger, "Stable, high-force, low-impedance robotic actuators for human-interactive machines," Ph.D. dissertation, Massachusetts Institute of Technology, Cambridge, MA, 2005.
S. P. Buerger and N. Hogan, "Complementary stability and loop shaping for improved human-robot interaction," IEEE Trans. Robotics, vol. 23, No. 2, pp. 232-244, 2007.
J. Nelder and R. Mead, "A simplex method for function minimization," The Computer Journal, vol. 7, pp. 308-313, 1964.
P. Canet, "Kalman filter estimation of angular velocity and acceleration: On-line implementation," McGill University, Montreal, Canada, Tech. Rep. TR-CIM-94-15, Nov. 1994.
D. A. Winter, Biomechanics and Motor Control of Human Movement (4th Edition). Wiley, 2009, p. 86.
K. C. Hayes and H. Hatze, "Passive visco-elastic properties of the structures spanning the human elbow joint," European Journal Applied Physiology, vol. 37, pp. 265-274, 1977.
J. Doke, J. M. Donelan, and A. D. Kuo, "Mechanics and energetics of swinging the human leg," Journal of Experimental Biology, vol. 208,pp. 439-445, 2005.
E. Burdet, R. Osu, D. W. Franklin, T. E. Milner, and M. Kawato, "The central nervous system stabilizes unstable dynamics by learning optimal impedance," Nature, vol. 414, No. 6862, pp. 446-449, 2001.
W. van Dijk, H. van der Kooij, and E. Hekman, "A passive exoskeleton with artificial tendons: Design and experimental evaluation," in Proc. IEEE Int. Conf. Rehabilitation Robotics (ICORR), 2011, pp. 1-6.
J. E. Colgate, "The control of dynamically interacting systems," Ph.D. dissertation, Massachusetts Institute of Technology, Cambridge, MA, 1988.
N. Hogan, "Impedance control: An approach to manipulation," in Proc. American Control Conference, 1984, pp. 304-313.
G. A.-Ollinger, J. E. Colgate, M. A. Peshkin, and A. Goswami, "Active-impedance control of a lower-limb assistive exoskeleton," in Proc. IEEE Int. Conf. Rehabil. Robot. (ICORR), 2007, pp. 188-195.
G. A.-Ollinger, "Active impedance control of a lower-limb assistive exoskeleton," Ph.D. dissertation, Northwestern University, Evanston, IL, 2007.
G. A.-Ollinger, J. E. Colgate, M. A. Peshkin, and A. Goswami, "A 1-DOF assistive exoskeleton with virtual negative damping: Effects on the kinematic response of the lower limbs," in Proc. IEEE Int. Conf. Intelligent Robots and Systems (IROS), 2007, pp. 1938-1944.

* cited by examiner

INTEGRAL ADMITTANCE SHAPING FOR AN EXOSKELETON CONTROL DESIGN FRAMEWORK

RELATED APPLICATIONS

The present application claims the benefit of U.S. Provisional Application No. 62/037,773, filed Aug. 15, 2014, entitled "INTEGRAL ADMITTANCE SHAPING: A NOVEL EXOSKELETON CONTROL DESIGN FRAMEWORK" in the name of Umashankar Nagarajan, Gabriel Aguirre-Ollinger, and Ambarish Goswami, and which is incorporated herein by reference in its entirety.

BACKGROUND

The present application generally relates to exoskeletons, and, more particularly, to an exoskeleton control design framework that shapes the frequency response magnitude profile of an integral admittance of a coupled human-exoskeleton joint so that a desired assistance is achieved, while ensuring coupled stability and passivity.

Exoskeletons are electromechanical devices that may physically and energetically interact with and provide assistance in the motion of human joints and/or limbs. Over the last two decades, exoskeleton devices have been developed to assist humans in their physical activities. (A. M. Dollar and H. Herr, "Lower extremity exoskeletons and active orthoses: Challenges and state-of-the-art," IEEE Trans. Robotics, vol. 24, no. 1, pp. 144-158, 2008; D. P. Ferris, "The exoskeletons are here," Journal of Neuroengineering and Rehabilitation, vol. 6, no. 17, pp. 1-3, 2009; and R. A. R. C. Gopura, K. Kiguchi, and D. S. V. Bandara, "A brief review on upper extremity robotic exoskeleton systems," in Proc. IEEE Int. Conf. Industrial and Information Systems (ICIIS), 2011, pp. 346-351.). Exoskeleton devices have been used for rehabilitation (N. G. Tsagarakis and D. G. Caldwell, "Development and control of a 'soft-actuated' exoskeleton for use in physiotherapy and training," Autonomous Robots, vol. 15, no. 1, pp. 21-23, 2003; A. Gupta and M. K. O'Malley, "Design of a haptic arm exoskeleton for training and rehabilitation," IEEE/ASME Trans. Mechatronics, vol. 11, no. 3, pp. 280-289, 2006; and A. U. Pehlivan, O. Celik, and M. K. O'Malley, "Mechanical design of a distal arm exoskeleton for stroke and spinal cord injury rehabilitation," in Proc. IEEE Int'l. Conf. Rehabilitation Robotics, 2011. Exoskeleton devices have been used for haptic interaction (T. Koyama, I. Yamano, K. Takemura, and T. Maeno, "Multi-fingered exoskeleton haptic device using passive force feedback for dextrous teleoperation," in Proc. IEEE/RSJ Int. Conf. Intelligent Robots and Systems (IROS), 2002, pp. 2905-2910 and A. Frisoli, F. Rocchi, S. Marcheschi, A. Dettori, F. Salsedo, and M. Bergamasco, "A new force-feedback arm exoskeleton for haptic interaction in virtual environments," in Proc. World Haptics Conf., IEEE Computer Society, 2005, pp. 195-201) as well as for performance augmentation (H. Kawamoto and Y. Sankai, "Power assist system hal-3 for gait disorder person," in Proc. Int. Conf. Comput. Helping People Special Needs (ICCHP), 2002, pp. 196-203; H. Kazerooni and R. Steger, "Berkeley lower extremity exoskeleton," ASME J. Dyn. Syst., Meas., Control, vol. 128, pp. 14-25, 2006 and G. T. Huang, "Wearable robots," Technol. Rev., pp. 70-73, July/August 2004).

Exoskeleton devices have been developed for assisting in walking and load carrying (H. Kazerooni and R. Steger, "Berkeley lower extremity exoskeleton, ASME J. Dyn. Syst., Meas., Control, vol. 128, pp. 14-25, 2006; J. E. Pratt, B. T. Krupp, C. J. Morse, and S. H. Collins, "The RoboKnee: An exoskeleton for enhancing strength and endurance during walking," in Proc. IEEE Int. Conf. Robotics and Automation (ICRA), 2004, pp. 2430-2435; and C. J. Walsh, K. Endo, and H. Herr, "A quasi-passive leg exoskeleton for load-carrying augmentation," Int. J. Humanoid Robotics, vol. 4, no. 3, pp. 487-506, 2007.); upper body motions (K. Kiguchi, K. Iwami, M. Yasuda, K. Watanabe, and T. Fukuda, "An exoskeletal robot for human shoulder joint motion assist," IEEE/ASME Trans. Mechatronics, vol. 8, no. 1, pp. 125-135, 2003; J. C. Perry, J. Rosen, and S. Burns, "Upper-limb powered exoskeleton design," IEEE/ASME Trans. Mechatronics, vol. 12, no. 4, pp. 408-417, 2007; and R. A. R. C. Gopura and K. Kiguchi, "SUEFUL-7: A 7-dof upper limb exoskeleton robot with muscle-model-oriented emg-based control," in Proc. IEEE/RSJ Int. Conf. Intelligent Robots and Systems (IROS), 2009, pp. 1126-1131.) and whole body motions (H. Kawamoto and Y. Sankai, "Power assist system hal-3 for gait disorder person," in Proc. Int. Conf Comput. Helping People Special Needs (ICCHP), 2002, pp. 196-203; G. T. Huang, "Wearable robots," Technol. Rev., pp. 70-73, July/August 2004; and S. Marcheschi, F. Salsedo, and M. Bergamasco, "Body Extender: Whole body exoskeleton for human power augmentation," in Proc. IEEE Int. Conf Robotics and Automation (ICRA), 2011, pp. 611-616.).

While assisting a human appears to be the objective of most exoskeleton devices, the term "assist" varies depending on the application. For example, an exoskeleton may be a prosthetic device that assists an amputee by providing a substitute to the lost limb (R. Versluys, G. Lenaerts, M. V. Damme, I. Jonkers, A. Desomer, B. Vanderborght, L. Peer-aer, G. V. der Perre, and D. Lefeber, "Successful preliminary walking experiments on a transtibial amputee fitted with a powered prosthesis," Prosthetics and Orthotics International, vol. 33, no. 4, pp. 368-377, 2009; J. K. Hitt, T. G. Sugar, M. Holgate, and R. Bellman, "An active foot-ankle prosthesis with biomechanical energy regeneration," Journal of Medical Devices, vol. 4, no. 1, p. 011003-011011, 2010; and H. M. Herr and A. M. Grabowski, "Bionic ankle-foot prosthesis normalizes walking gait for persons with leg amputation," Proc. Biol. Sci., The Royal Society, vol. 279, no. 1728, pp. 457-464, 2012.); or a device that assists a paraplegic to recover the motor function of the limb (K. Suzuki, G. Mita, H. Kawamoto, Y. Hasegawa, and Y. Sankai, "Intention-based walking support for paraplegia patients with robot suit hal," Advanced Robot., vol. 21, pp. 1441-1469, 2007; A. Tsukahara, R. Kawanishi, Y. Hasegawa, and Y. Sankai, "Sit-to-stand and stand-to-sit transfer support for complete paraplegic patients with robot suit hal," Advanced Robot., vol. 24, pp. 1615-1638, 2010; and R. Farris, H. Quintero, and M. Goldfarb, "Preliminary evaluation of a powered lower limb orthosis to aid walking in paraplegic individuals," IEEE Trans. Neural Syst. Rehabil. Eng., vol. 19, no. 6, pp. 652-659, 2011.).

One type of exoskeleton device provides performance augmentation to non-pathological humans. Such exoskeleton devices focus on assisting physically weak humans regain their lost power and agility, as well as focusing on assisting physically strong humans achieve improved human performance. Assistance for performance augmentation devices may be defined as the reduction in metabolic cost of a human activity (D. Ferris, G. Sawicki, and M. Daley, "A physiologist's perspective on robotic exoskeletons for human locomotion," Int. J. Humanoid Robots, vol. 4, no. 3, pp. 507-528, 2007.). Researchers have demonstrated reduction in metabolic cost for human walking with tethered exoskeleton devices, whose power supply is off-board the device (D. P. Ferris, J. M. Czerniecki, and B. Hannaford, "An ankle-foot orthosis powered by artificial pneumatic muscles," J. Appl. Biomech., vol. 21, no. 2, pp. 189-197, 2005; G. S. Sawicki and D. P. Ferris, "Mechanics and energetics of level walking with powered ankle exoskeletons," J. Exp. Biol., vol. 211, no. Pt. 9, pp. 1402-1413, 2008; and P. Malcolm, W. Derave, S. Galle, and D. D. Clercq, "A simple exoskele-ton that assists plantarflexion can reduce the metabolic cost of human walking," PLoS One, vol. 8, no. 2, p. e56137, 2013). For activities like hopping, which involve spring-like behavior, researchers have demonstrated reduction in metabolic cost by adding passive elements parallel with the human joints (A. M. Grabowski and H. M. Herr, "Leg exoskeleton reduces the metabolic cost of human hopping," J. Appl. Physiol., vol. 107, no. 3, pp. 670-678, 2009 and D. J. Farris and G. S. Sawicki, "Linking the mechanics and energetics of hopping with elastic ankle exoskeletons," J. Appl. Physiol., vol. 113, no. 12, pp. 1862-1872, 2012.). However, this is an exception since the activity of hopping is particularly suited for such assistance.

Presently, no autonomous, self-contained exoskeleton devices have provided a reduction in metabolic cost for walking or running. Therefore, it would be desirable to provide a system and method that overcome the above. The system and method would modify the coupled human-exoskeleton system dynamics such that the desired assistance is achieved by using integral admittance shaping to shape the frequency response magnitude profile of the integral admittance of the coupled human-exoskeleton joint such that the desired assistance is achieved, while guaranteeing coupled stability and passivity.

SUMMARY

In accordance with one embodiment, an assistive exoskeleton control system is disclosed. The assistive exoskeleton control system has a controller generating a positive assistance by shaping a closed loop integral admittance of a coupled human exoskeleton system to a desired assistance ratio $A_d$ by modifying a control transfer function using a cut-off frequency of a low pass filter.

In accordance with one embodiment, an assistive exoskeleton control system is disclosed. The assistive exoskeleton control system has a controller shaping a closed loop integral admittance of a coupled human exoskeleton system, wherein a frequency response magnitude of the closed loop integral admittance is greater than that of a natural human joint. The controller generates a control transfer function defined by:

$$U_e(s) = \frac{K_\alpha H_{lo}(s)s^2 + K_\omega s + K_\theta}{s},$$

where $K_\alpha = I_e - I_e^d$, $K_\omega = b_e - b_e^d$, and $K_\theta = k_e - k_e^d$ are the feedback gains on angular acceleration $\ddot{\theta}_o$, angular velocity $\dot{\theta}_e$ and angle $\theta_e$ respectively and $H_{lo}(s)$ is the second-order Butterworth low-pass filter defined by $$H_{lo}(s) = \frac{\omega_{lo}^2}{s^2 + \sqrt{2}\,\omega_{lo}s + \omega_{lo}^2}$$

where $\omega_{lo}$ is the cut-off frequency of the second-order Butterworth low-pass filter.

In accordance with one embodiment, an assistive exoskeleton control system is disclosed. The assistive exoskeleton system has a controller generating a positive assistance by shaping a closed loop integral admittance of a coupled human exoskeleton system to a desired assistance ratio $A_d$ by generating a control transfer function defined by:

$$U_c(s) = \frac{K_\alpha H_{lo}(s)s^2 + K_\omega s + K_\theta}{s},$$

where $K_\alpha = I_e - I_e^d$, $K_\omega = b_e - b_e^d$, and $K_\theta = k_e - k_e^d$ are the feedback gains on angular acceleration $\ddot{\theta}_e$, angular velocity $\dot{\theta}_e$ and angle $\theta_e$ respectively and $H_{lo}(s)$ is the second-order Butterworth low-pass filter defined by:

$$H_{lo}(s) = \frac{\omega_{lo}^2}{s^2 + \sqrt{2}\,\omega_{lo}s + \omega_{lo}^2}$$

where $\omega_{lo}$ is the cut-off frequency of the second-order Butterworth low-pass filter. The controller optimizes the desired assistance ratio $A_d$ by minimizing an optimization equation defined by: $|A-A_d|^2+\omega R$ wherein A is an assistance ratio over a desired frequency range and R is a resistance ratio over the desired frequency range. The controller controls a damping ratio defined by: $|\zeta_{heu}-\zeta_h|/|\zeta_h|<\epsilon$, where $\zeta_{heu}$ is a damping ratio of the coupled human-exoskeleton system, $\zeta_h$ is a damping ration of an unassisted human joint and $\epsilon$ is a desired variation in the damping ratio of human joint dynamics. The controller is stable and passive.

BRIEF DESCRIPTION OF THE DRAWINGS

In the descriptions that follow, like parts are marked throughout the specification and drawings with the same numerals, respectively. The drawing figures are not necessarily drawn to scale and certain figures may be shown in exaggerated or generalized form in the interest of clarity and conciseness. The disclosure itself, however, as well as a preferred mode of use, further objectives and advantages thereof, will be best understood by reference to the following detailed description of illustrative embodiments when read in conjunction with the accompanying drawings, wherein.

DESCRIPTION OF THE INVENTION

Figure 1:
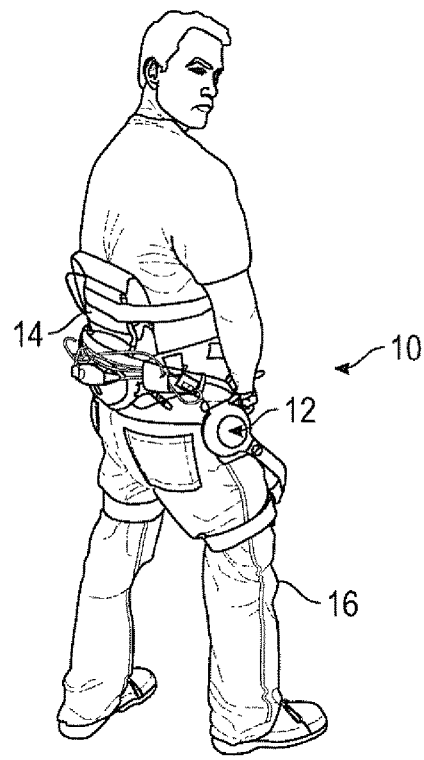
FIG. 1 is a perspective view of an exoskeleton device implementing an exemplary admittance shaping controller in accordance with one aspect of the present application.

The description set forth below in connection with the appended drawings is intended as a description of presently preferred embodiments of the disclosure and is not intended to represent the forms in which the present disclosure may be constructed and/or utilized. The description sets forth the functions and the sequence of steps for constructing and operating the disclosure in connection with the illustrated embodiments. It is to be understood, however, that the same or equivalent functions and sequences may be accomplished by different embodiments that are also intended to be encompassed within the spirit and scope of this disclosure.

Embodiments of the disclosure provide a control design framework for designing exoskeleton devices aimed at providing performance augmentation. Assistance may be achieved by increasing the admittance and decreasing the impedance of the coupled human-exoskeleton joint, which produces motion amplification and torque reduction. The control design framework may modify the coupled human-exoskeleton system dynamics such that the desired assistance may be achieved by using integral admittance shaping to shape the frequency response magnitude profile of the integral admittance of the coupled human-exoskeleton joint such that the desired assistance is achieved, while guaranteeing coupled stability and passivity.

Embodiments of the disclosure take a systems interaction approach to defining assistance for joint exoskeleton devices that may achieve performance augmentation. In order to be assistive, a joint exoskeleton should achieve motion amplification, i.e., larger joint motion amplitude for the same joint torque, or torque reduction, i.e., reduced joint torque amplitude required to achieve the same joint motion. This should result in a reduction of human effort to achieve nominal human tasks and also enable super-human capabilities with nominal human effort. The motion amplification and torque reduction have a direct correspondence to decreasing the impedance and increasing the admittance (inverse of impedance (N. Hogan and B. S, O, Impedance and Interaction Control, Robotics and Automation Handbook. CRC Press, LLC., 2005, ch. 19.). Hence, a joint exoskeleton device may be considered assistive if it decreases the impedance or increases the admittance of the human joint. It should be noted that reducing the impedance and increasing the admittance has the potential to reduce the metabolic cost (E.

Burdet, R. Osu, D. W. Franklin, T. E. Milner, and M. Kawato. "The central nervous system stabilizes unstable dynamics by learning optimal impedance," Nature, vol. 414, no. 6862, pp. 446-449, 2001.).

One issue with designing exoskeleton devices is that a passive (unpowered) exoskeleton may add inertia to the human joint resulting in an increase in the impedance of the human joint. This in turn may increase the metabolic cost. Hence, in general, a passive exoskeleton cannot provide sufficient positive power to overcome the negative metabolic effects of the added exoskeleton inertia (C. J. Walsh, K. Endo, and H. Herr, "A quasi-passive leg exoskeleton for load-carrying augmentation," Int. J. Humanoid Robotics, vol. 4, no. 3, pp. 487-506, 2007; L. M. Mooney, E. J. Rouse, and H. M. Herr, "Autonomous exoskeleton reduces metabolic cost of human walking during load carriage," Journal of Neuroengineering and Rehabilitation, vol. 11, no. 80, 2014; and W. van Dijk, H. van der Kooij, and E. Heiman, "A passive exoskeleton with artificial tendons: Design and experimental evaluation," in Proc. IEEE Int. Conf. Rehabilitation Robotics (ICORR), 2011, pp. 1-6.). On the other hand, active exoskeletons may use actuators to directly add power to human joints. Embodiments of this disclosure focus on such active joint exoskeleton devices. In order to add sufficient positive power to decrease the impedance of the human joint, the exoskeleton controller generally needs to overcome its own impedance and then compensate for the impedance of the human joint. This may result in an active exoskeleton behavior, which may raise stability concerns. Hence, it may be important to ensure that the coupled human-exoskeleton system is stable. However, a stable coupled human-exoskeleton system may still be prone to instability when contacting passive environments (E. Colgate and N. Hogan, "An analysis of contact instability in terms of passive physical equivalents," in Proc. IEEE Int. Conf Robotics and Automation (ICRA), 1989, pp. 404-409.). The risk of instability may be avoided if the coupled system exhibits passivity (J. E. Colgate, "The control of dynamically interacting systems," Ph.D. dissertation, Massachusetts Institute of Technology, Cambridge, Mass., 1988.). Hence, the exoskeleton controller should try to ensure that the coupled system is passive, in addition to being stable Impedance control (N. Hogan, "Impedance control: An approach to manipulation," in Proc. American Control Conference, 1984, pp. 304-313.) has emerged as a popular approach for designing physical interaction controllers. Active impedance control (G. A.-Ollinger, J. E. Colgate, M. A. Peshkin, and A. Goswami, "Active-impedance control of a lower-limb assistive exoskeleton," in Proc. IEEE Int. Conf. Rehabil. Robot. (ICORR), 2007, pp. 188-195; and G. A.-Ollinger, "Active impedance control of a lower-limb assistive exoskeleton," Ph.D. dissertation, Northwestern University, Evanston, Ill. 2007.) has been used to achieve virtual negative damping (G. A.-Ollinger, J. E. Colgate, M. A. Peshkin, and A. Goswami, "A 1-DOF assistive exoskeleton with virtual negative damping: Effects on the kinematic response of the lower limbs," in Proc. IEEE Int. Conf. Intelligent Robots and Systems (IROS), 2007, pp. 1938-1944.) for a 1-DOF exoskeleton that assists a free swinging leg. It has also been used to achieve inertia compensation ("Design of an active one-degree-of-freedom lower-limb exoskeleton with inertia compensation," Int. J. Robotics Research, vol. 30, no. 4, pp. 486-499, 2011; and "Inertia compensation control of a one-degree-of-freedom exoskeleton for lower-limb assistance: Initial experiments," IEEE Trans. Neural Syst. Rehabil. Eng., vol. 20, no. 1, pp. 68-77, 2012.) which may increased the natural frequency of steady-state swinging compared to its natural frequency with the passive exoskeleton. However, the exoskeletons used in the aforementioned citations were statically supported, and the power supply and motor were isolated from the human. Moreover, there was no evidence of an increase in the natural frequency of the steady-state swinging over its natural frequency without the exoskeleton.

The present control design framework focuses its study on an elementary assistive exoskeleton with a single degree of freedom (DOE) assisting a 1-DOF human joint and presents conceptual and quantitative definitions of assistance and resistance for a 1-DOF joint based on the frequency response of its integral admittance (integral of admittance, i.e., torque-to-angle relationship). However, it may be extend to multiple degrees of freedom. A detailed study on the effect of assisting one DOF on another DOF may be useful in designing multi-DOF assistive exoskeleton devices. Moreover, the definitions and approach presented below may be extended to include task-level assistance rather than joint-level assistance. For example, the output of the linear system presented below is a joint angle, whereas the output may be used chosen as a task-level output like the position of the foot.

Assistance for a 1-DOF joint may be defined based on the concept of motion amplification, which in turn corresponds to increasing its admittance (U. Nagarajan, G. A.-Ollinger, and A. Goswami, "Defining assistance: A linear systems perspective," IEEE Trans. Robotics (In Submission), 2014.). Using the quantitative metrics for assistance and resistance presented, the present control design framework uses Integral Admittance Shaping that finds exoskeleton control parameters that shape the frequency response of the integral admittance of the coupled human-exoskeleton joint such that the user-defined desired assistance is achieved. The present control design framework may ensure that the coupled human-exoskeleton system is both stable and passive, in order to ensure stability while interacting with passive environments (J. E. Colgate and N. Hogan, "An analysis of contact instability in terms of passive physical equivalents," in Proc. IEEE Int. Conf Robotics and Automation (ICRA), 1989, pp. 404-409.).

The system parameters of the coupled human-exoskeleton system used in the analysis and experimental results presented in the exemplary embodiments of the disclosure may be seen in Table 1 shown below. The human limb data corresponds to the leg of a human whose weight may be approximately 65 kg and height approximately 1.65 m. In the exemplary embodiments of the disclosure, the knee may be assumed to be locked and all parameters may be computed for the hip joint. The moment of inertia $I_h$ may be obtained from Cadaver data provided in "Biomechanics and Motor Control of Human Movement" by D. A. Winter ($4^{th}$ Edition, Wiley, 2009, p. 86), and may be scaled to the human weight and height. The joint damping coefficient may be taken from "Passive visco-elastic properties of the structures spanning the human elbow joint," by K. C. Hayes and H. Hatze (European Journal Applied Physiology, vol. 37, pp. 265-274, 1977), and the joint stiffness coefficient may be obtained using $k_h = I_h \omega^2_{nh}$ where the natural frequency $\omega_{nh}$ may be obtained from "Mechanics and energetics of swinging the human leg" by J. Doke, J. M. Donelan, and A. D. Kuo (Journal of Experimental Biology, vol. 208, pp. 439-445, 2005).

Coupled Human-Exoskeleton System Parameters

TABLE 1

| Parameters | Symbol | Value |
|---|---|---|
| Human Leg Mass (locked knee) | $m_h$ | 10.465 kg |
| Human Leg Length | $l_h$ | 0.875 m |
| Human Leg Moment of Inertia | $I_h$ | 3.381 kg·m² |
| Human Hip Joint Damping Coefficient | $b_h$ | 3.5 N·m·s/rad |
| Human Hip Joint Stiffness Coefficient | $k_h$ | 54.677 N·m/rad |
| Human Leg Natural Angular Frequency | $w_{nh}$ | 4.021 rad/s |
| Exoskeleton Arm Moment of Inertia | $I_e$ | 0.01178 kg·m² |
| Exoskeleton Joint Damping Coefficient | $b_e$ | 0.34512 N·m·s/rad |
| Exoskeleton Joint Stiffness Coefficient | $k_e$ | 0.33895 N·m/rad |
| Coupling Damping Coefficient | $b_c$ | 9.474 N·m·s/rad |
| Coupling Stiffness Coefficient | $k_c$ | 1905.043 N·m/rad |

The exoskeleton parameters listed in Table 1 may be obtained from system identification experiments on a 1-DOF hip exoskeleton shown in FIG. 1, which is described in greater detail below. The coupling parameters listed in Table 1 may be obtained with the assumption that the coupling parameters second-order dynamics with the exoskeleton inertia $I_e$ may have a damping ratio $\zeta_c = 1$ and natural frequency $\omega_{nc} = 100\, \omega_{nh}$, where $\omega_{nh}$ is the natural frequency of the human limb.

Figure 2A:
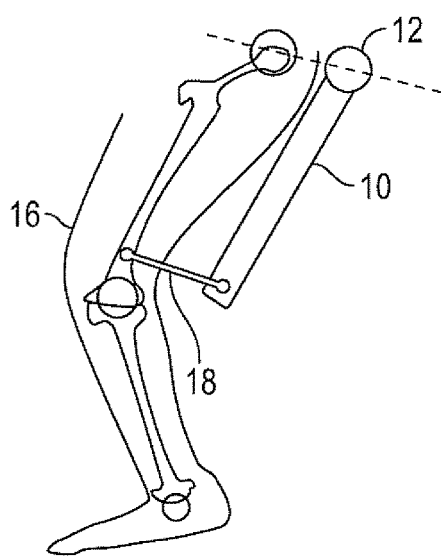
FIG. 2A and FIG. 2B show representations of an exemplary one degree-of-freedom (1-DOF) coupled human-exoskeleton system with rigid coupling (FIG. 2A) and soft coupling (FIG. 2B) in accordance with one aspect of the present application.
Figure 2B:
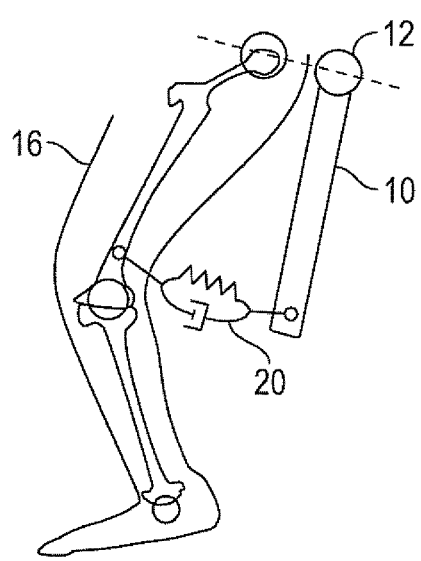

Referring now to the figures, FIG. 1 shows an embodiment of a Stride Management Assist (SMA) exoskeleton device 10 in accordance with embodiments of the invention. The SMA device 10 may have two 1-DOF hip joints 12. In the embodiment shown, a torso support 14 may be added to the SMA device 10 to provide greater damping and to reduce oscillations. The coupling between an exoskeleton and a human limb 16 may play a role in determining the performance of the exoskeleton 10, and the coupling may be either rigid 18 or soft 20 as shown in FIGS. 2A-2B and in FIG. 3A-3B. In the case of rigid coupling 18 as shown in FIG. 2A, there may be no relative motion between the human limb 16 and the exoskeleton 10, whereas in the case of soft coupling 20 in FIG. 2B, the human limb 16 and the exoskeleton 10 may move relative to each other. In actual implementations of an exoskeleton attached to a limb there may be a soft coupling due to muscle, skin tissue, fat layers, and other body substances between the bone and the exoskeleton device. The soft couple may be modeled in embodiments with a linear torsional spring with a coefficient $k_c$ and a linear torsional damper with coefficient $b_c$ as shown in FIG. 3B.

Figure 3A:
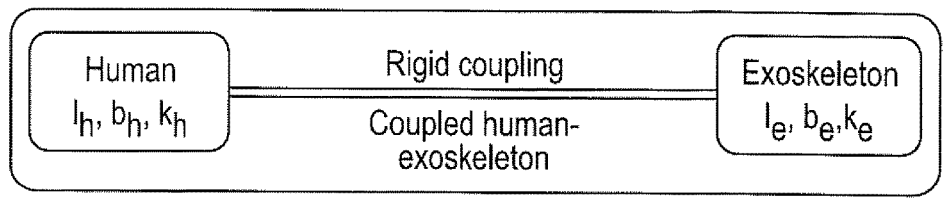
FIGS. 3A and 3B are block diagram summarizing equations for the 1-DOF coupled human-exoskeleton system with rigid coupling (FIG. 3A) and soft coupling (FIG. 3B) in accordance with one aspect of the present application.
Figure 3B:
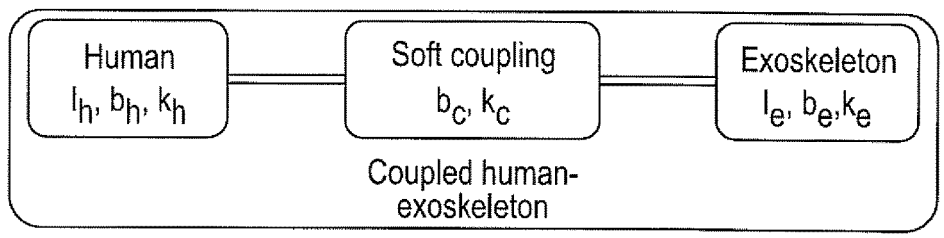

As shown in FIG. 3A-3B, a coupled human-exoskeleton system with rigid coupling (FIG. 3A) and soft coupling (FIG. 3B) may be modeled with second-order linear models to represent the joint dynamics of a human as shown in Equation 1 below, and the exoskeleton in Equation 2 shown below. The moment of inertia, joint damping and joint stiffness of the 1-DOF human joint may be given by $I_h$, $b_h$, $k_h$ respectively, and that for the exoskeleton may be given by $\{I_e, b_e, k_e\}$. In the of a soft coupling, the coupling damping and stiffness coefficients may be given by $b_c$, $k_c$, respectively and the coupled dynamics is of the fourth-order as given by Equations 4-5 shown below.

The linear equations of motion of an isolated 1-DOF human joint of an exemplary embodiment of the disclosure may be given by $$I_h \ddot{\theta}_h(t) + b_h \dot{\theta}_h(t) + k_h \theta_h(t) = \tau_h(t) \tag{1}$$

where $\theta_h(t)$ is the joint angle trajectory, $I_h$, $b_h$, $k_h$ are the associated moment of inertia, joint damping coefficient and joint stiffness coefficient respectively, and $\tau_h(t)$ is the joint torque trajectory. The stiffness term $k_h \theta_h(t)$ may include the linearized gravitational terms.

Similarly, the linear equations of motion of an isolated 1-DOF exoskeleton may be given by:

$$I_e \ddot{\theta}_e(t) + b_e \dot{\theta}_e(t) + k_e \theta_e(t) = \tau_e(t), \tag{2}$$

where $\theta_h(t)$ is the joint angle trajectory, $I_e$, $b_e$, $k_e$ is the associated moment of inertia, joint damping coefficient and joint stiffness coefficient respectively, and $\tau_h(t)$ is the joint torque trajectory.

The linear equations of motion of a coupled human exoskeleton system with rigid coupling as shown in FIGS. 2A and 3A may be given by:

$$I_h + I_e \ddot{\theta}_h(t) + b_h + b_e \dot{\theta}_h(t) + k_h + k_e \theta_h(t) = \tau_h(t) + \tau_e(t) \tag{3}$$

Since there is no relative motion between the exoskeleton and the human limb, the exoskeleton joint angle $\theta_e = \theta_h$, and hence $\theta_e$ may be ignored in Equation 3.

Rigid coupling between the exoskeleton and the human limb may generally imply rigidly attaching the exoskeleton to the bone as shown in FIG. 2A, which is generally not realistic. Realistic and practical exoskeleton device may generally be attached to the limb, wherein muscle, tissue, fat and other body substances may produce a soft coupling between the exoskeleton device and the bone as shown in FIG. 2B. This soft coupling may be modeled with a linear torsional spring with coefficient $k_c$ and a linear torsional damper with coefficient $b_c$ as shown in FIG. 3B.

The linear equations of motion of a coupled human exoskeleton system with soft coupling may be given by:

$$I_h \ddot{\theta}_h(t) + b_h \dot{\theta}_h(t) + k_h \theta_h(t) = \tau_h(t) + \tau_c(t) \tag{4}$$

$$I_e \ddot{\theta}_e(t) + b_e \dot{\theta}_e(t) + k_e \theta_e(t) = \tau_e(t) - \tau_c(t) \tag{5}$$

where $\tau_c$ is the coupling joint torque given by:

$$\tau_c(t) = b_c(\dot{\theta}_e(t) - \dot{\theta}_h(t)) + k_c(\theta_e(t) - \theta_h(t)). \tag{6}$$

Unlike in Equation 3, the exoskeleton joint angle $\theta_e$ is different from the human joint angle $\theta_h$ because of the soft coupling, and hence results in an extra DOF. Therefore, the coupled system dynamics with soft coupling in Equations 4-6 is of a fourth-order, whereas the coupled system dynamics with rigid coupling in Equation 3 is of a second-order.

Embodiments of the disclosure aim to modify the joint dynamics of the coupled human-exoskeleton system by modifying the impedance and admittance of the coupled system.

The mechanical impedance, denoted by z(t), of a system may be defined as the dynamic operator that determines the output force/torque function from an input velocity/angular velocity function (N. Hogan and S. O. Buerger, Impedance and Interaction Control, Robotics and Automation Handbook. CRC Press, LLC., 2005, ch. 19.). The mechanical admittance, denoted by y(t), of a system may be defined as the dynamic operator that determines the output velocity/angular velocity function from an input force/torque function (N. Hogan and S. O. Buerger, Impedance and Interaction Control, Robotics and Automation Handbook. CRC Press, LLC., 2005, ch. 19.). Thus, the impedance of a system may be defined as its property to resist motion, whereas the admittance may be defined as its property to allow motion.

For the linear human joint dynamics in Equation (1), the impedance transfer function $Z_h(s)$ may be given by:

$$Z_h(s) = \frac{\tau_h(s)}{\Omega_h(s)} \quad (7)$$

$$= \frac{I_h s^2 + b_h s + k_h}{s},$$

and the admittance transfer function $Y_h(s)$ may be given by:

$$Y_h(s) = \frac{\Omega h(s)}{\tau h(s)} \quad (8)$$

$$= \frac{s}{I_h s^2 + b_h s + k_h}$$

where $\Omega_h(s)$ is the Laplace transform of $\dot{\theta}_h$, and $\tau_h(s)$ is the Laplance transform of $\tau_h(t)$. For a linear system, its impedance may be the inverse of its admittance and vice-versa, as it can be seen in Equations 7-8.

The integral admittance transfer function $X_h(s)$ may be defined as the integral of the admittance transfer function and may be given by:

$$X_h(s) = \frac{\Theta h(s)}{\tau h(s)} \quad (9)$$

$$= \frac{1}{I_h s^2 + b_h s + k_h}$$

where $\Theta_h(s)$ is the Laplace transform of $\theta_h(t)$. The admittance $Y_h(s)$ maps torque to angular velocity, while the integral admittance $X_h(s)$ maps torque to angle. The integral admittance may be used extensively in the further sections of this disclosure.

In embodiments described in this disclosure the human joint, exoskeleton, and coupling element may be treated as three isolated systems, and their corresponding impedance and admittance transfer functions may be written as follows. The admittance transfer function of an isolated human joint $Y_h(s)$ may be given by Equation 8, while the admittance transfer function of an isolated exoskeleton $Y_e(s)$ may be given by:

$$Y_e(s) = \frac{\Omega_e(s)}{\tau_e(s)} \quad (10)$$

$$= \frac{s}{I_e s^2 + b_e s + k_e}$$

and the impedance transfer function of an isolated coupling element $Z_c(s)$ may be given by:

$$Z_c(s) = \frac{\tau c(s)}{\Omega c(s)} \quad (11)$$

$$= \frac{b_c s + k_c}{s}$$

where $\Omega_c(s) = \Omega_e(s) - \Omega_h(s)$ is the Laplace transform of the joint angular velocity of the coupling element. Using Equations 8, 10 and 11, the whole coupled system dynamics with the human joint, exoskeleton and coupling element given by Equations 4-6 may be represented as a block diagram shown in FIG. 4. The block diagram represents a coupled human-exoskeleton system with soft coupling where $Y_h(s)$, $Y_e(s)$ and $Z^c(s)$ are the isolated human admittance, exoskeleton admittance and coupling impedance transfer functions respectively.

As disclosed herein exoskeleton controllers may be designed to modify the coupled system joint dynamics, i.e., the joint impedance, admittance, and integral admittance of the coupled human exoskeleton system. The following is a derivation of an embodiment of the closed-loop dynamics of a coupled human-exoskeleton system with an exoskeleton controller, and presents the coupled stability and passivity conditions.

Figure 4:
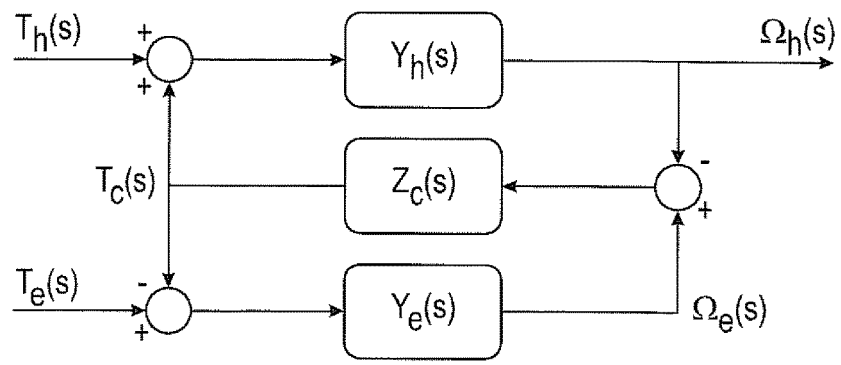
FIG. 4 is a block diagram of a coupled human-exoskeleton system with soft coupling in accordance with one aspect of the present application.
Figure 5A:
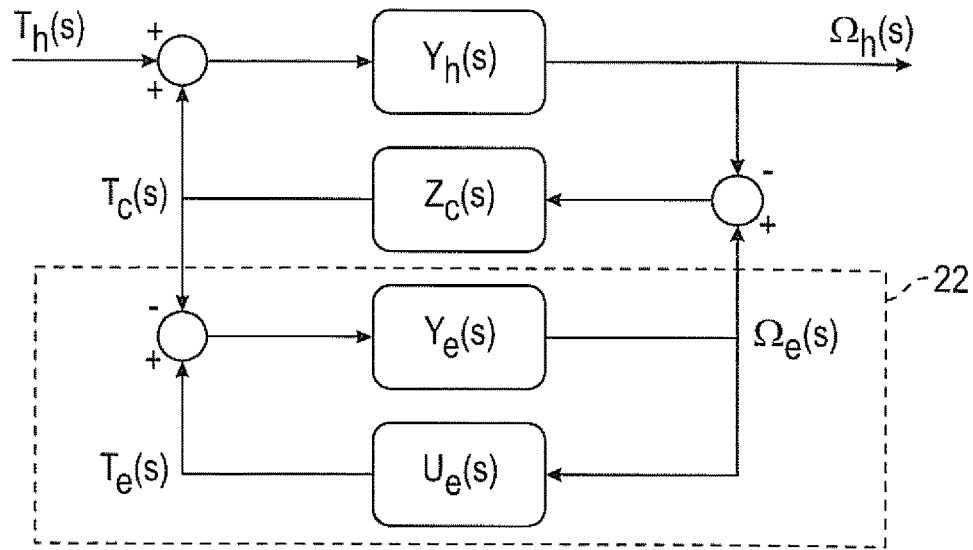
FIG. 5A-FIG. 5C are block diagrams of illustrative coupled human-exoskeleton systems with the exoskeleton controller $U_e(s)$ in accordance with one aspect of the present application.

For exoskeleton control transfer function $U_e(s)$ that feeds back the exoskeleton joint information, the coupled human-exoskeleton system in FIG. 4 reduces to the closed-loop system shown in FIG. 5A. The analysis presented below may be applicable to any general exoskeleton controller $U_e(s)$, and the specific exoskeleton control structure used in this disclosure may be seen below.

Figure 5B:
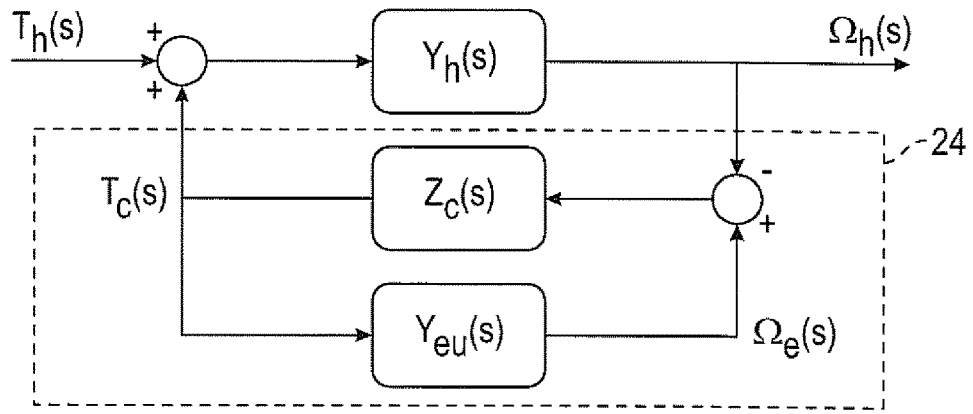
Figure 5C:
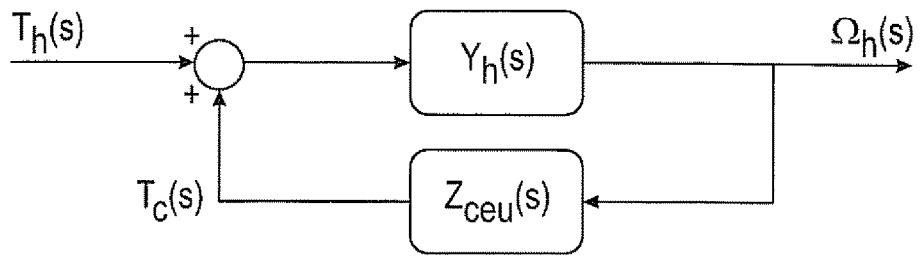

The outlined region 22 in FIG. 5A containing $Y_e(s)$ and $U_e(s)$ may be reduced to a single transfer function $Y_{eu}(s)$ which may be given by:

$$Y_{eu}(s) = \frac{-Y_e(s)}{1 - Y_e(s)U_e(s)} \quad (12)$$

as shown in FIG. 5B. Similarly, the highlighted region 24 containing $Z_c(s)$ and $Y_{eu}(s)$ in FIG. 5B may be reduced to a single transfer function $Z_{ceu}(s)$ given by:

$$Z_{ceu}(s) = \frac{-Z_c(s)}{1 - Z_c(s)Y_{eu}(s)} \quad (13)$$

as shown in FIG. 5C.

The loop transfer function $L_{heu}(s)$ that may be needed to evaluate the stability of the feedback system shown in FIG. 5C may be given by:

$$L_{heu}(s) = Y_h(s)Z_{eus}(s), \quad (14)$$

Since the closed-loop system in FIG. 5C has a positive feedback loop, one may need to look at the gain margin of $-L_{heu}(s)$ to evaluate the coupled stability of the overall closed-loop system. The gain margin (GM) of $-L_{heu}(s)$ may be given by:

$$GM(-L_{heu}) = \frac{1}{|-L_{heu}(j\omega_c)|} \quad (15)$$

where $\omega_c$ is the phase-crossover frequency when the phase of $-L_{heu}(s)$ is 180°, i.e. $\angle -L_{heu}(j\omega_c) = 180°$. The gain margin $GM(-L_{heu})$ may give the maximum positive gain exceeding which the closed-loop system becomes unstable. Therefore, in order for the coupled human-exoskeleton system shown in FIG. 5C to be stable, the following condition should be satisfied:

$$GM(-L_{heu}) > 1. \quad (16)$$

From FIG. 5C, the overall closed-loop admittance $Y_{heu}(s)$ of the coupled human-exoskeleton system with the exoskeleton controller $U_e(s)$ may be given by:

$$Y_{heu}(s) = \frac{Y_h(s)}{1 - Y_h(s)Z_{ceu}(s)} \quad (17)$$

and its corresponding closed-loop integral admittance $X_{heu}(s)$ may be given by:

$$X_{heu}(s) = \frac{Y_{heu}(s)}{s} \quad (18)$$
$$= \frac{X_h(s)}{1 - Y_h(s)Z_{ceu}(s)},$$

where $X_h(s) = Y_h(s)/s$ as shown in Equation 9. It should be noted that the unassisted human joint dynamics is of second-order as shown in Equation 1, while the coupled human-exoskeleton joint dynamics shown in Equations 4-6 are of a fourth-order. However, with high coupling stiffness and damping, the coupled system dynamics are predominantly of a second-order. The order of the closed-loop coupled system depends on the order of the exoskeleton controller $U_e(s)$.

In addition to coupled stability, an important requirement for dynamically interacting systems may be coupled passivity (J. E. Colgate, "The control of dynamically interacting systems," Ph.D. dissertation, Massachusetts Institute of Technology, Cambridge, Mass., 1988). Coupled passivity may ensure that the coupled human-exoskeleton system does not become unstable when in contact with any passive environment (J. E. Colgate and N. Hogan, An analysis of contact instability in terms of passive physical equivalents," in Proc. IEEE Int. Conf. Robotics and Automation (ICRA), 1989, pp. 404-409). A linear time-invariant system may be said to be passive (J. E. Colgate, "The control of dynamically interacting systems," Ph.D. dissertation, Massachusetts Institute of Technology, Cambridge, Mass., 1988) when the impedance transfer function $Z(s)$ may satisfy the following conditions:

1) $Z(s)$ has no poles in the right-hand half of the complex plane; and
2) $Z(s)$ has a Nyquist plot that lies wholly in the right-hand half of the complex.

The first condition generally requires $Z(s)$ to be stable, while the second condition generally requires the phase of $Z(s)$ to lie within $-90°$ and $90°$ for all frequencies (J. E. Colgate, "The control of dynamically interacting systems," Ph.D. dissertation, Massachusetts Institute of Technology, Cambridge, Mass., 1988), i.e., $\angle Z(j\omega) \in [-90°, 90°]$. This, in turn, may enforce that the phase of the system admittance $\angle Y(j\omega) \in [-90°, 90]$ and the phase of the system integral admittance $\angle X(j\omega) \in [-180°, 0°]$.

Therefore, in order for a stable coupled human-exoskeleton system satisfying Equation 15 to be passive, the following condition may need to be satisfied:

$$\angle X_{heu}(j\omega) \in [-180°, 0°] \forall \omega. \quad (19)$$

Figure 6A:
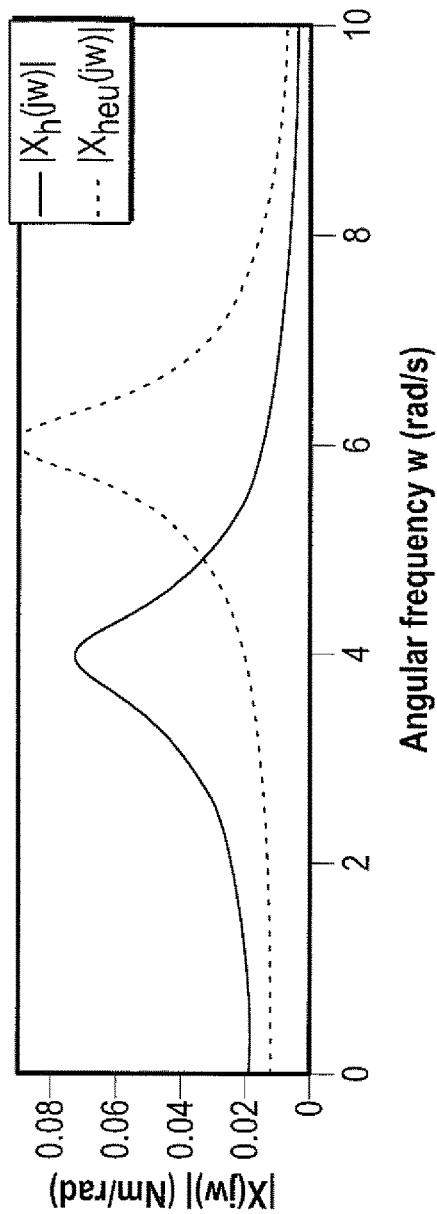
FIG. 6A-FIG. 6B are illustrative graphs of the frequency response magnitude and phase plots of an unassisted human $X_h(s)$ and a hypothetical coupled human-exoskeleton system $X_{heu}(s)$ passivity in accordance with one aspect of the present application.
Figure 6B:
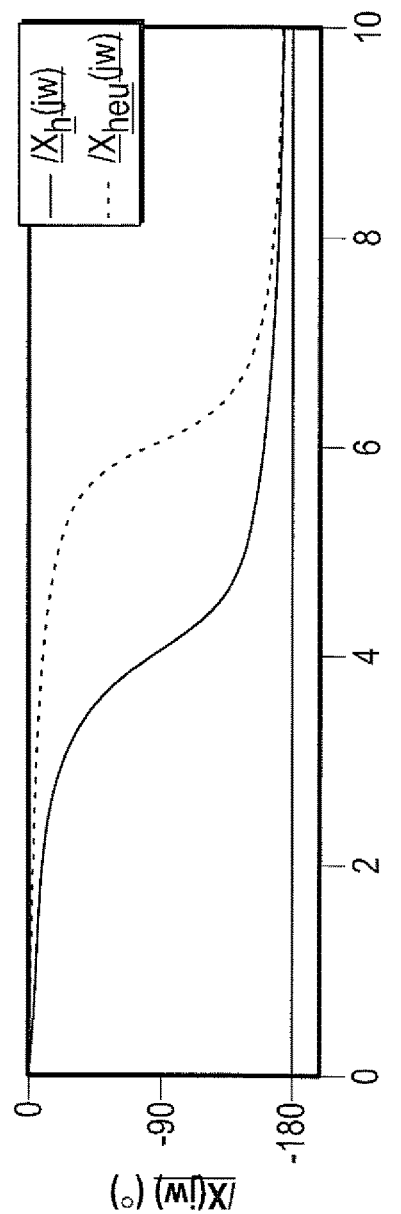

FIG. 6A-6B shows the frequency response magnitude and phase plots of the integral admittance of an unassisted human joint $X_h(s)$ and a hypothetical coupled human-exoskeleton joint $X_{heu}(s)$ with the parameters listed in Table 1. Given that the unassisted human and the coupled human-exoskeleton system considered here are stable, and it can be seen from FIG. 6B that they are also passive satisfying Equation 19.

A novel control design framework may be disclosed below that may shape the frequency response magnitude of the closed-loop integral admittance $X_{heu}(s)$ of the coupled human exoskeleton system in Equation 18 such that the 1-DOF human joint motion may be assisted. FIG. 6A presents the frequency response magnitude plot of an unassisted human joint $X_h(s)$ and a hypothetical coupled human-exoskeleton joint $X_{heu}(s)$, which is just one of many shapes that the magnitude profile of the closed-loop integral admittance may have. The magnitude of the frequency response has been traditionally preferred over its phase for defining performance objectives (S. P. Buerger, "Stable, high-force, low-impedance robotic actuators for human-interactive machines," Ph.D. dissertation, Massachusetts Institute of Technology, Cambridge, Mass., 2005; and S. P. Buerger and N. Hogan, "Complementary stability and loop shaping for improved human-robot interaction," IEEE Trans. Robotics, vol. 23, no. 2, pp. 232-244, 2007.). In this framework, the magnitude may be chosen for integral admittance shaping, while the phase is used to evaluate the passivity of the coupled system.

In order to design the shape of $|X_{heu}(j\omega)|$, an objective for the exoskeleton may need to be defined. In an exemplary embodiment, an objective may be to provide assistance and avoid resistance. In order to define the shape of $|X_{heu}(j\omega)|$ that provides assistance and avoids resistance, the assistance and resistance may need to be defined in a clear and quantitative way. Below, presents conceptual and quantitative definitions of assistance and resistance using the frequency response magnitude of the integral admittance, followed by a description of the desired characteristics of an assistive exoskeleton, and a constrained optimization formulation that shapes the closed-loop integral admittance such that the desired assistance is achieved, while guaranteeing coupled stability and passivity.

The following definitions for assistance and resistance may be use in accordance with embodiments of the disclosure. Definition 1: A 1-DOF human joint may be said to be assisted by an exoskeleton if the frequency response magnitude of the integral admittance of the coupled human-exoskeleton system is greater than that of the natural human for all frequencies of interest. According to the above definition, a human joint is assisted when $|X_{heu}(j\omega)| > |X_h(j\omega)|$, and it is resisted when $|X_{heu}(j\omega)| < |X_h(j\omega)|$. An assistive exoskeleton behavior generally produces motion amplification, i.e., for a given input joint torque, the amplitude of the joint angular motion is larger than that without assist, and torque reduction, i.e., the amplitude of joint torque required to achieve a particular joint angle motion is smaller than that required without assist. Conversely, motion reduction and torque amplification are generally characteristic of a resistive exoskeleton behavior.

Figure 7A:
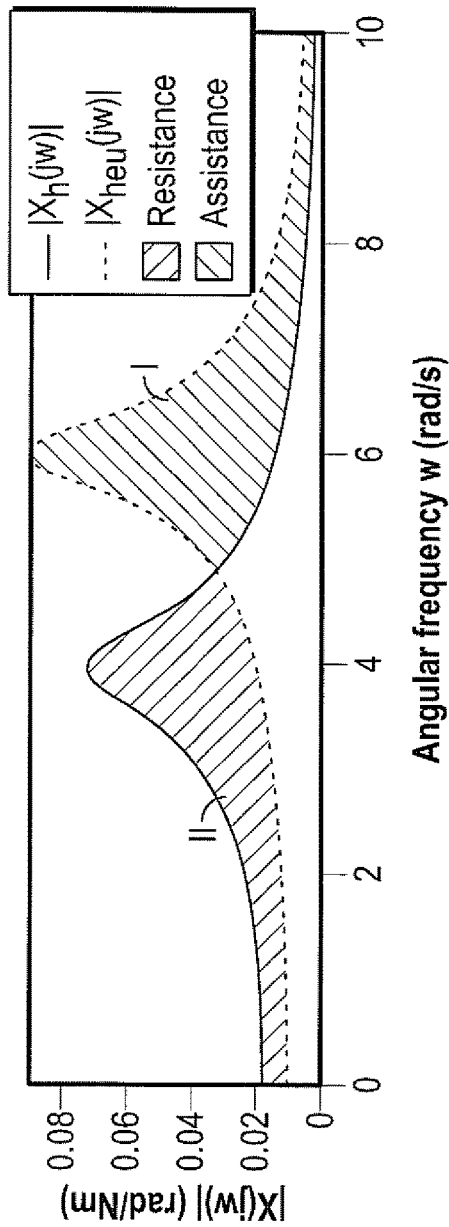
FIGS. 7A-7B are illustrative graphs of Assistance and Resistance of a 1-DOF assistive exoskeleton represented in terms of an assistance function $AF(\omega)$ and a resistance function $RF(\omega)$ in accordance with one aspect of the present application.
Figure 7B:
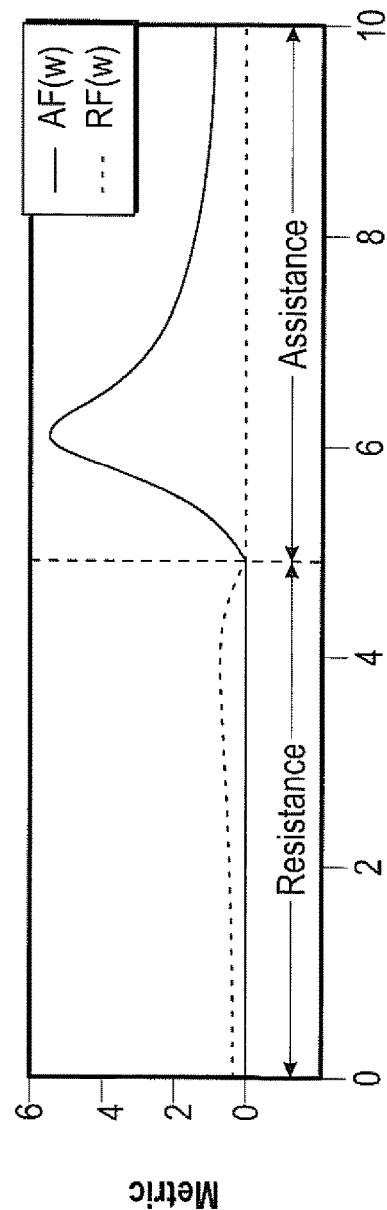

FIGS. 7A-7B show assistance and resistance of a 1-DOF assistive exoskeleton system represented in terms of integral admittance $X(s)$ (FIG. 7A), and assistance function $AF(\omega)$ and resistance function $RF(\omega)$ (FIG. 7B). The magnitude of the frequency response of the integral admittance of an unassisted human is denoted by $|X_h(j\omega)|$, and that of the closed-loop integral admittance of the coupled human-exoskeleton system is denoted by $|X_{heu}(j\omega)|$.

FIG. 7A shows the frequency response magnitude plots of an unassisted human and a hypothetical coupled human-exoskeleton system whose parameters are listed in Table 1. As per Definition 1, the area I represent the frequencies where there is assistance, wherein $|X_{heu}(j\omega)|>|X_h(j\omega)|$, and the area II represents the frequencies where there is resistance, wherein $|X_{heu}(j\omega)|<|X_h(j\omega)|$.

FIGS. 7A-7B shows that at each frequency $\omega$, the exoskeleton behavior could be either assistive or resistive. Based on this observation, the assistance function $AF(\omega)$ may be defined as:

$$AF(\omega) = \begin{cases} \frac{|X_{heu}(j\omega)| - |X_h|(j\omega)|}{|X_h(j\omega)|} & \text{if } |X_{heu}(j\omega)| \geq |X_h(j\omega)| \\ 0 & \text{if } |Xheu(j\omega)| < |X_h(j\omega)| \end{cases} \quad (20)$$

and the resistance function $RF(\omega)$ may be defined as:

$$RF(\omega) = \begin{cases} 0 & \text{if } |X_{heu}(j\omega)| \geq |X_h(j\omega)| \\ \frac{|X_h(j\omega)| - |X_{heu}(j\omega)|}{|X_h(j\omega)|} & \text{if } |Xheu(j\omega)| < |X_h(j\omega)| \end{cases}, \quad (21)$$

At any frequency $\omega$, the assistance function $AF(\omega) \in [0, \infty]$, and the resistance function $RF(\omega) \in [0, 1]$. When the coupled human-exoskeleton joint dynamics is identical to the unassisted natural human joint dynamics, i.e., $|X_{heu}(j\omega)|=|X_h(j\omega)|$, then $AF(\omega)=RF(\omega)=0$, $\forall \omega$. The upper bound $AF(\omega)=\infty$ may be achieved when $|X_{heu}(j\omega)|=\infty$, and the upper bound $RF(\omega)=1$ may be achieved when $|X_{heu}(j\omega)|=0$. Although both these cases are mathematically valid, they are generally not realistic.

In specific embodiments of the disclosure, it may be important to note that the exoskeleton may either assist or resist at any particular frequency $\omega$ for a single joint, which may be seen from FIG. 7B. Using the assistance function $AF(\omega)$ and the resistance function $RF(\omega)$ the following quantitative metrics for assistance and resistance of a 1-DOF assistive exoskeleton, namely assistance ration and resistance ratio may be defined.

Definition 2: Assistance Ratio A may be defined as the average value of the assistance function $AF(\omega)$ over a range of frequencies $[0, \omega_f]$, and may be given by:

$$\mathcal{A} = \frac{1}{\omega_f} \int_0^{\omega_f} \mathcal{AF}(\omega) d\omega. \quad (22)$$

Definition 3: Resistance Ratio R may be defined as the average value of the resistance function $RF(\omega)$ over a range of frequencies $[0, \omega_f]$ and may be given by:

$$\mathcal{R} = \frac{1}{\omega_f} \int_0^{\omega_f} \mathcal{RF}(\omega) d\omega. \quad (23)$$

Similar to the assistance and resistance functions, the assistance ratio A $\in [0, \infty]$ and resistance ratio R$\in[0, 1]$. As described above, the upper bounds A=$\infty$ and R=1 may be achieved if $|X_{heu}(j\omega)|=\infty$ and $(Xa(j\omega))|=0$ respectively $\forall \omega$. Although these bounds may be mathematically valid, the bounds may not be realistic for proper integral admittance transfer function. With the above definitions of assistance and resistance, the below section may enumerate embodiments of desired characteristics of a resistive exoskeleton.

The Net Assistance Ratio $\tilde{A}$ may be given by:

$$\tilde{A} = A - R, \quad (24)$$

which may quantitatively define the overall assistance for an exoskeleton device that is assistive for some set of frequencies and resistive for some other set of frequencies as shown in FIGS. 7A-7B. It is to be noted that $\tilde{A} \in [-\infty, \infty]$. A positive net assistance ratio ($\tilde{A}>0$) generally indicates that the exoskeleton is more assistive than resistive, whereas a negative net assistance ratio ($\tilde{A}<0$) generally indicates that the exoskeleton is more resistive than assistive. It should be noted that the net assistance ratio $\tilde{A}$ may characterizes the exoskeleton performance over the entire range of frequencies of interest, while the performance at different subsets of frequency ranges can vary substantially.

An objective of embodiments of an assistive exoskeleton may be to provide assistance to human motion while not resisting any motion. However, it may be vital to ensure that the coupled human-exoskeleton system is also stable. Furthermore, coupled passivity as defined in "The control of dynamically interacting systems," by J. E. Colgate (Ph.D. dissertation, Massachusetts Institute of Technology, Cambridge, Mass., 1988) may be needed since coupled passivity may guarantee stability even when the coupled human-exoskeleton system interacts with any passive environment.

Therefore, the necessary desired characteristics of a 1-DOF assistive exoskeleton may be listed as follows:

1) Coupled Stability, i.e., $GM(L_{heu})>1$ (Eq. 16);
2) Coupled Passivity, i.e., $\angle X_{heu}(j\omega) \in [-180°, 0°]$. $\forall \omega$ (Eq. 19);
3) Positive Assistance, i.e. A>0 (Eq. 22); and
4) No Resistance, i.e. R=0 (Eq. 23).

The above characteristics may be the necessary desired characteristics of a 1-DOF assistive exoskeleton. However, more characteristics may be added to the list depending on the task and the desired goals of the exoskeleton implementation.

Since an exoskeleton is an electromechanical device that is physically and energetically interacting with a human, the mechanical structure and dynamic behavior of the exoskeleton should be comfortable. Thus, characterizing dynamic comfort may be important in determining the desired exoskeleton behavior. A stable and passive coupled human-exoskeleton system with no resistance, as highlighted above, may contribute towards making the exoskeleton dynamically comfortable. However, a large assistance may not necessarily be comfortable. Since every individual is different, each human may generally have a certain desired assistance $A_d$ that may provide maximum dynamic comfort. This desired assistance generally varies from person to person and may even vary between tasks for the same person.

In addition to achieving the desired assistance $A_d$, there may be other constraints that may potentially determine the dynamic comfort of an exoskeleton behavior. For example, the oscillatory behavior of a second-order system may be determined by its damping ratio $\zeta$. Decreasing the damping ratio of the coupled human-exoskeleton system below that of the unassisted human ($\zeta_{heu} \ll \zeta_h$) may cause the coupled joint dynamics to be more under-damped and oscillatory, which may be uncomfortable. Similarly, increasing the damping ratio above its original value ($\zeta_{heu} \gg \zeta_h$) may cause the coupled joint dynamics to be over-damped and sluggish, which may also be uncomfortable. Therefore, damping ratio variation may be constrained to remain close to its original value in order to provide greater comfort. The damping ratio $\zeta_h$ of the human leg's second-order dynamics may be given by:

$$\zeta_h = \frac{b_b}{2\sqrt{I_h k_h}}. \quad (25)$$

Although the closed-loop dynamics $X_{heu}(s)$ of the coupled human-exoskeleton system is of a higher order, it is predominantly of second-order, and the damping ratio $\zeta_{heu}$ of the dominant second-order closed-loop dynamics may be computed as follows:

$$\zeta_{heu} = \sqrt{\frac{M_p - \sqrt{M_p^2 - 1}}{2M_p}}. \quad (26)$$

where $M\hat{}p$ is the normalized peak magnitude of $|X_{heu}(j\omega)|$ given by $$M\hat{}p = \frac{\max|X_{heu}(j\omega)|}{|X_{heu}(0)|}, \quad (27)$$

where $\max|X_{heu}(j\omega)|$ is the peak magnitude of $|X_{heu}(j\omega)|$, and $|X_{heu}(0)|$ is its magnitude at zero frequency. It should be noted that Equation 26 is valid if the closed-loop dynamics $X_{heu}(s)$ is predominantly second-order in the frequency range of interest.

From Equation 25 and Equation 26, a constraint on the damping ratio such as $|\zeta_{heu}-\zeta_h|/|\zeta_h|<\epsilon$, where $\epsilon$ is desired variation in the damping ratio of the human joint dynamics, may be added in order to make the assistive exoskeleton behavior more dynamically comfortable.

The above sections may have provided the metrics to evaluate assistance and enumerated the desired characteristics of an assistive exoskeleton. Now, embodiments of designs for an exoskeleton controller $U_e(s)$ that shapes the closed-loop integral admittance of the coupled human-exoskeleton system based on these metrics may be disclosed below.

Exoskeleton control law for $\tau_e(t)$ may produce an exoskeleton dynamics given by Equation 5, and hence given a desired exoskeleton dynamics, one can derive a corresponding controller. If the desired exoskeleton dynamics may be given by a desired moment of inertia $I_e^d$, a desired joint damping coefficient $b_c^d$ and a desired joint stiffness coefficient $k_c^d$, then the exoskeleton torque $\tau_e$ required to achieve the desired exoskeleton dynamics may be given by $$\tau_e(t)=(I_e-I_e^d)\ddot{\theta}_e(t)+(b_c-b_c^d)\dot{\theta}_e(t)+(k_c-k_c^d)\theta_e(t) \quad (28)$$

It can be verified that the control law in Equation 28 may reduce the exoskeleton dynamics in Equation 5 to:

$$I_e^d\ddot{\theta}_e(t)+b_c^d\dot{\theta}_e(t)+k_c^d\theta_e(t)=-\tau_c(t) \quad (29)$$

as desired. The exoskeleton controller $U^0_e(s)$ corresponding to the control law in Equation 28 that feeds back angular velocity $\Omega_e(s)$ may be given by:

$$U_e^0(s) = \frac{K_\alpha s^2 + K_\omega s + K_\theta}{s} \quad (30)$$

where $K_\alpha=I_e-I_e^d$, $K_\omega=b_c-b_c^d$, and $K_\theta=k_c-k_c^d$ are the feedback gains on angular acceleration $\ddot{\theta}_e$, angular velocity $\dot{\theta}_e$ and angle $\theta_e$ respectively. However, instead of Equation 30, present embodiments of this disclosure use the following modified exoskeleton control transfer function $U_e(s)$ given by:

$$U_e(s) = \frac{K_\alpha H_{lo}(s)s^2 + K_\omega s + K_\theta}{s} \quad (31)$$

where $H_{lo}(s)$ is the second-order Butterworth low-pass filter which may be given by:

$$H_{lo}(s) = \frac{\omega_{lo}^2}{s^2 + \sqrt{2}\,\omega_{lo}s + \omega_{lo}^2} \quad (32)$$

where $\omega_{lo}$ is the cut-off frequency of the filter.

It has been shown in "Design of an active one-degree-of-freedom lower-limb exoskeleton with inertia compensation," Int. J. Robotics Research, vol. 30, no. 4, pp. 486-499, 2011; "Inertia compensation control of a one-degree-of-freedom exoskeleton for lower-limb assistance: Initial experiments," IEEE Trans. Neural Syst. Rehabil. Eng., vol. 20, no. 1, pp. 68-77, 2012; and "A one-degree-of-freedom assistive exoskeleton with inertia compensation: the effects on the agility of leg swing motion," Proc. Inst. Mech. Eng. H., vol. 225, no. 3, pp. 228-245, 2011., that reducing the moment of inertia of the coupled human-exoskeleton system is a requirement for the exoskeleton controller to provide assistance to the human. Positive acceleration feedback as shown in Equation 30 is an obvious way to achieve inertia reduction. However, as may be shown below, using just acceleration feedback as in the control law in Equation 30, the moment of inertia of the coupled human-exoskeleton system may not be reduced below that of the unassisted human limb without compromising coupled stability. It shows that the exoskeleton controller $U^0_e(s)$ in Equation 30 may at the most compensate for the exoskeleton moment of inertia before going unstable. It is important to note here that coupled stability is an important requirement for the design of exoskeleton controllers, which may not be compromised. The coupled stability requirement limits the amount of inertia that may be compensated for using an exoskeleton controller with just acceleration feedback.

However, this does not rule out the possibility of stably achieving inertia reduction. As may be shown below, feedback of acceleration filtered using a low-pass filter enables the exoskeleton controller $U_e(s)$ in Equation 31 to reduce the moment of inertia of the coupled human-exoskeleton system below that of the unassisted human limb. The exoskeleton controller may compensate for the exoskeleton moment of inertia and then compensates for some portion of the human moment of inertia as well. Moreover, as may be shown, the second-order filter shown in Equation 32 helps stably achieve the largest inertia reduction among the class of Butterworth low-pass filters of orders n=1 to n=4 while guaranteeing coupled stability.

Figure 8:
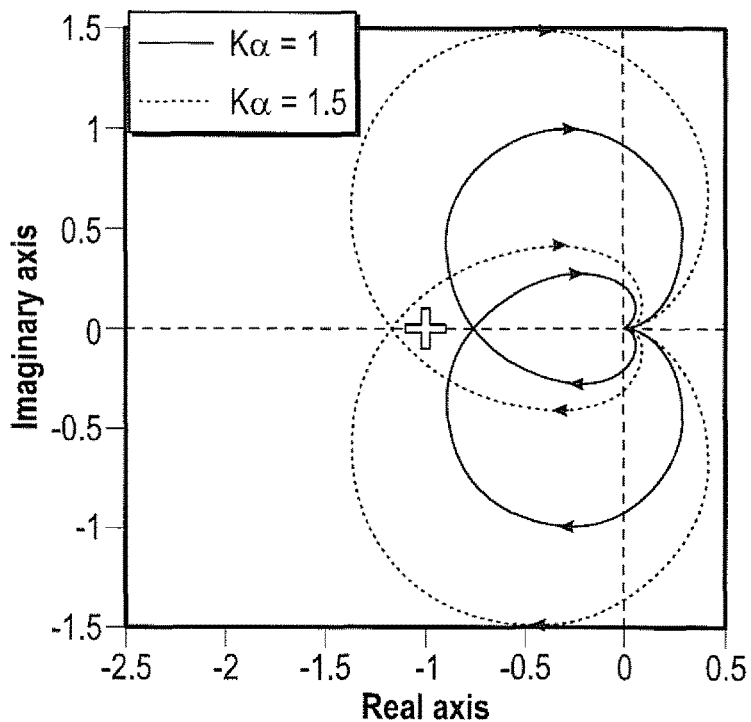
FIG. 8 shows an illustrative series of Nyquist plots of $-L_{heu}(s)$ for different control parameters that achieve both coupled stability and passivity in accordance with one aspect of the present application.

FIG. 8 shows the Nyquist plots of $-L_{heu}(s)$ for different values of $K_\alpha$, while other control parameters in Equation 31 are fixed at $K_\theta=K_\omega=0$ and $\omega_{lo}=10$ rad/s. Since $-L_{heu}(s)$ has no unstable poles, just the number of encirclements of the Nyquist plot around $-1+j0$ may be sufficient to determine the stability of the closed-loop system. For $K_\alpha=1$, its Nyquist plot does not encircle $-1+j0$ resulting in a stable closed-loop system, whereas for $K_\alpha=1.5$, its Nyquist plot encircles $-1+j0$ twice resulting in an unstable closed-loop system. Using Equation 15, for $K_\alpha=1$, the gain margin is 1.3181, which is greater than one and hence stable as per Equation 16, whereas for $K_\alpha=1.5$, the gain margin is 0.8580, which is less than one and hence unstable as per Equation 16. FIG. 8 emphasizes that there exists a set of control parameters $\{K_\theta, K_\omega, K_\alpha, \omega_{lo}\}$ for which the coupled human-exoskeleton system can be unstable, and hence it is vital to ensure that the control parameters are chosen such that the coupled stability condition (Equation 16) is satisfied.

The control transfer function $U_e(s)$ shown in Equation 31 is characterized by four control parameters, namely, $K_\theta$, $K_\omega$, $K_\alpha$ and $\omega_{lo}$. These parameters directly affect the closed-loop integral admittance $X_{heu}(s)$, and can be chosen such that the frequency response magnitude of the closed-loop integral admittance $X_{heu}(s)$ is shaped such that the desired assistance ratio $A_d$ defined above is achieved.

Given a desired assistance ratio $A_d$, the optimal set of control parameters of the 1-DOF coupled human-exoskeleton system in Equation 18 may be obtained using the following constrained optimization problem:

$$\underset{\{K_\theta, K_\omega, K_\alpha, \omega_{lo}\}}{\text{minimize}} |\mathcal{A} - \mathcal{A}_d|^2 \quad (33)$$

subject to $GM(-L_{heu}) > 1.$ $\angle X_{heu}(j\omega) \in [-180°, 0°] \forall \omega.$ $\mathcal{R} = 0.$ $\left|\frac{\zeta_{heu} - \zeta_h}{\zeta_h}\right| < \epsilon.$ The objective in Equation 33 attempts to achieve the desired assistance ratio $A_d$, while satisfying the stability (Equation 16) and passivity (Equation 19) constraints. However, in in present embodiments of this disclosure, the following constrained optimization was used to find the optimal control parameters:

$$\underset{\{K_\theta, K_\omega, K_\alpha, \omega_{lo}\}}{\text{minimize}} |\mathcal{A} - \mathcal{A}_d|^2 + w\mathcal{R} \quad (34)$$

subject to $GM(-L_{heu}) > 1.$ $\angle X_{heu}(j\omega) \in [-180°, 0°] \forall \omega.$ $\left|\frac{\zeta_{heu} - \zeta_h}{\zeta_h}\right| < \epsilon.$ The optimization in Equation 34 replaces the hard constraint of R=0 in Equation 33 with a soft constraint using a large weight w on the resistance ratio R. The soft constraint gives the optimization freedom to explore the space of control parameters that may result in non-zero resistance ratio, and, with a sufficiently large w, the optimization will converge to control parameters that result in either zero resistance ratio (R=0) or negligible resistance ratio (R≈0). It is important to note that the coupled stability, passivity and comfort constraints are retained as hard constraints in Equation 34.

In embodiments of the present disclosure, the optimizations were performed in Matlab using fminsearch( ) function, which in turn used Nelder-Mead simplex algorithm (J. Nelder and R. Mead, "A simplex method for function minimization," The Computer Journal, vol. 7, pp. 308-313, 1964.). Nelder-Mead simplex algorithm is a heuristic search method that uses function evaluations to solve unconstrained optimization problems. In embodiments of the present disclosure, analytical expressions for the assistance ratio A, resistance ratio R and their gradients with respect to the control parameters may be difficult to obtain, and hence Nelder-Mead simplex algorithm was chosen. Since Nelder-Mead simplex is an unconstrained optimization solver, the constraints had to be indirectly enforced. Large cost function values ($10^5$) were returned when the constraints were not satisfied. Moreover, the soft constraint weight was chosen to be w=$10^5$. Since the optimization attempts at minimizing the cost function, it drives the solution away from these large values and hence, indirectly enforces the constraints. The functional and parameter tolerances were both set to $10^{-5}$.

Figure 9:
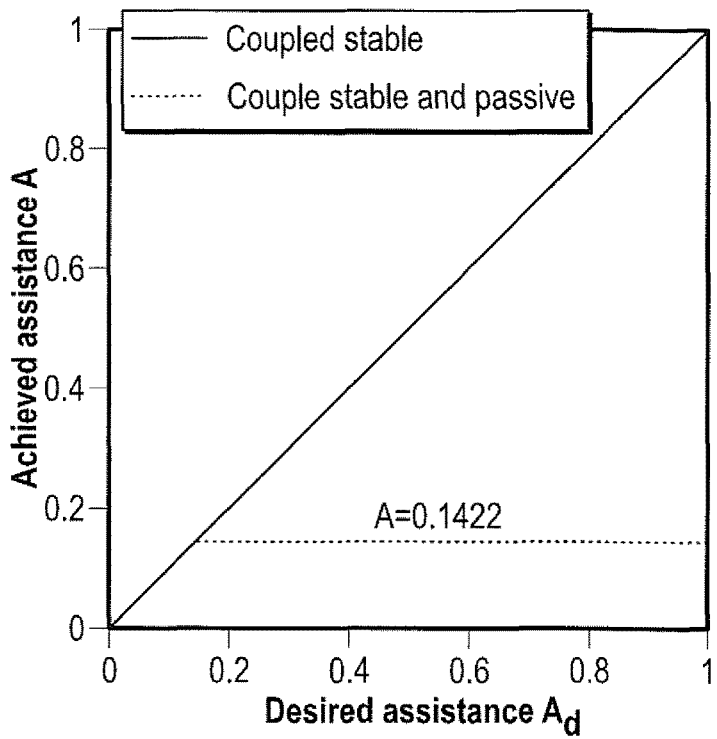
FIG. 9 shows an illustrative graph of achieved assistance rations A with and without passive constraints passivity in accordance with one aspect of the present application.

FIG. 9 shows the achieved assistance ratios A for the different desired assistance ratios $A_d \in [0, 1]$ (at 0.01 discretization) with and without the coupled passivity constraint in Equation 34. It may be seen that without the coupled passivity constraint, the optimization algorithm was able to find control parameters that achieved the desired assistance ratios $A_d \in [0, 1]$ with a functional tolerance of $10^{-5}$. These control parameters may result in coupled human-exoskeleton systems that are stable. However, for assistance ratios A>0.1422, the optimal control parameters resulted in coupled human-exoskeleton systems that are stable but not passive, i.e., the coupled system is active for some range of frequencies $\omega$.

Figure 10A:
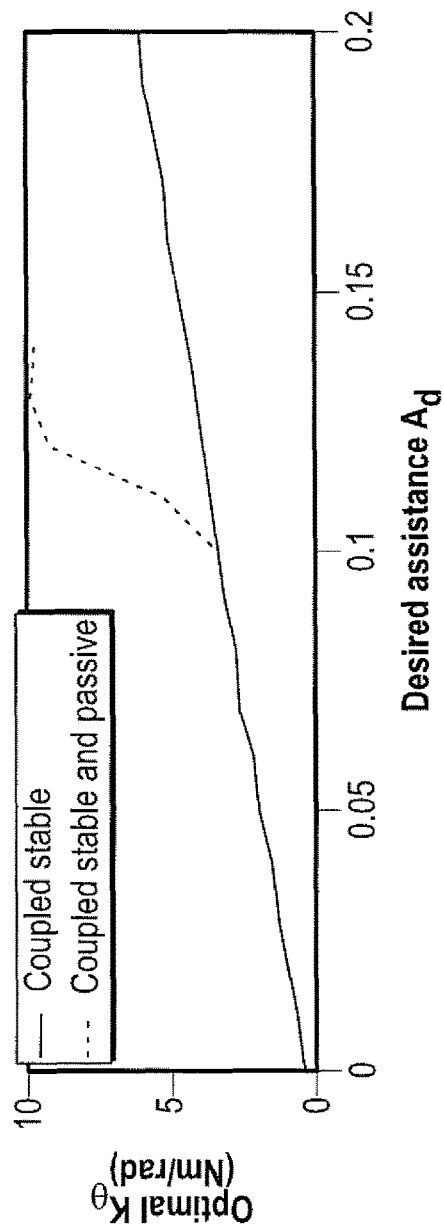
FIGS. 10A-10D are illustrative graphs showing derived optimal control parameters for different desired assistance rations $A_d$ with and without passivity constraints in accordance with one aspect of the present application.
Figure 10B:
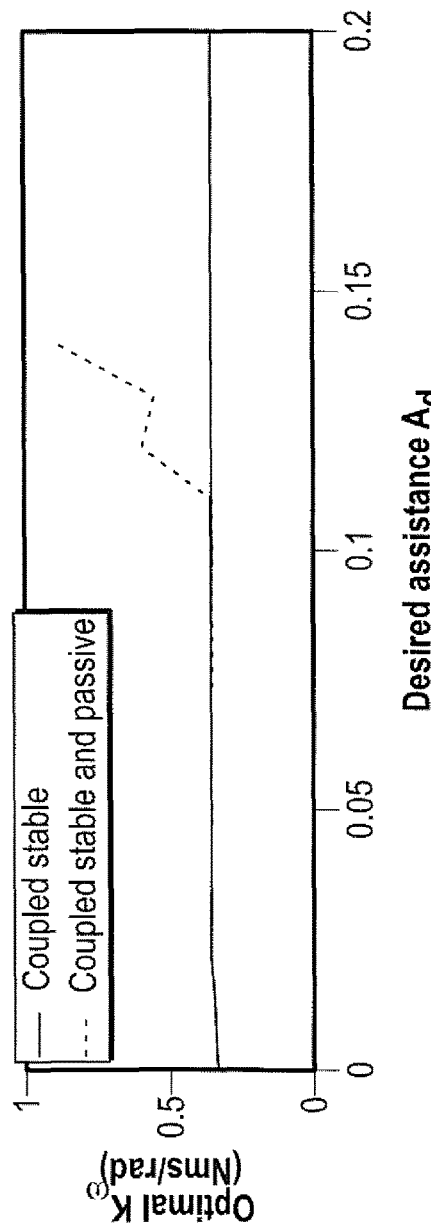
Figure 10C:
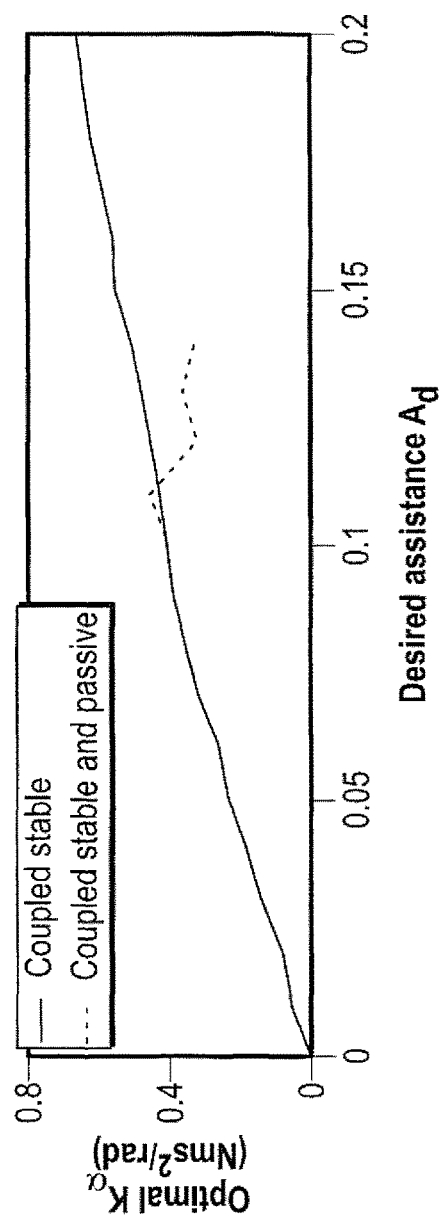
Figure 10D:
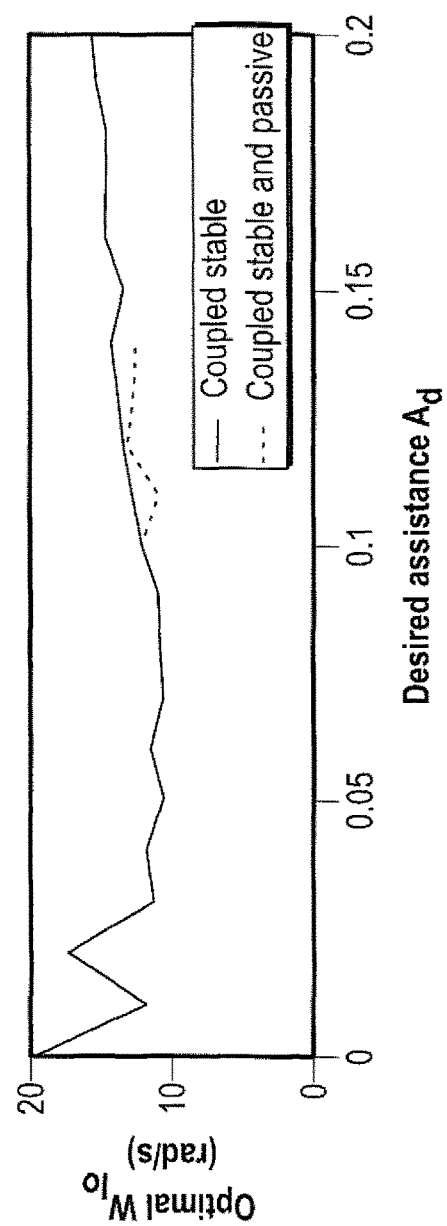

FIGS. 10A-10D shows the derived optimal control parameters for the different desired assistance ratios $A_d$ with and without the passivity constraint. FIG. 10A is for $K_\theta$, FIG. 10B is for $K\omega$, FIG. 10C is for $K_\alpha$ and FIG. 10D is for $\omega_{lo}$. It may be seen that for desired assistance ratios $A_d$>0.1, the optimal control parameters with passivity constraint deviate from the values obtained without the passivity constraint, and for desired assistance ratios $A_d$>0.1422, no set of control parameters achieved the desired assistance ratios within the functional tolerance while satisfying the passivity constraint.

For the results presented in FIGS. 10A-10D, the optimal control parameters for $A_d$=0 ($|X_{heu}(j\omega)|=|X_h(j\omega)|$) were first obtained, and then the optimal control parameters for $A_d$ were chosen as the initial optimization parameters for $A'_d=A_d+0.01$. Therefore, the optimization converges to the control parameters closest to those that match the integral admittance magnitude profile of the unassisted human.

Figure 11A:
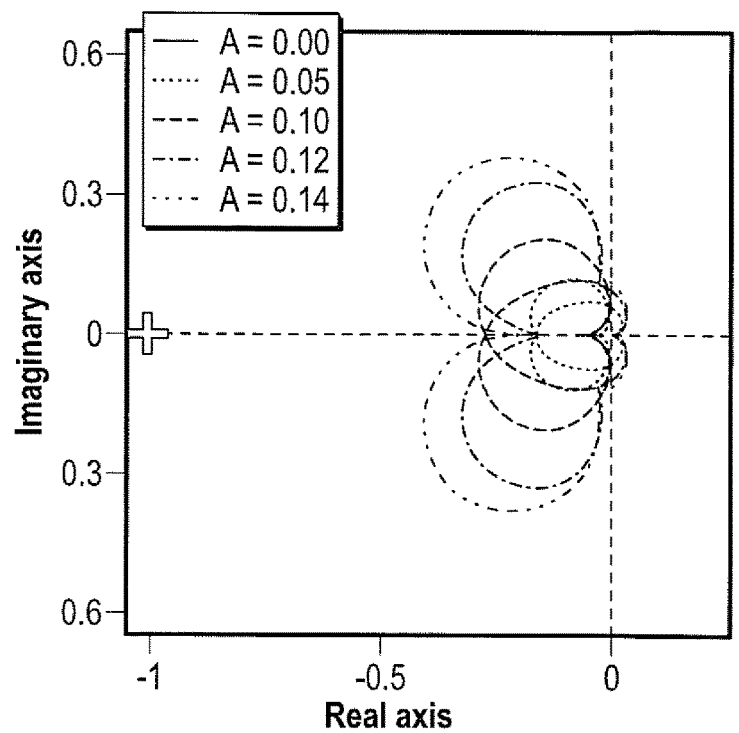
FIGS. 11A-11B are Nyquist plots of $-L_{heu}(s)$ for the optimal control parameters shown in FIGS. 10A-10D that achieve coupled stability with passivity constraints (FIG. 10A) and without the passivity constraint (FIG. 11B) in accordance with one aspect of the present application.
Figure 11B:
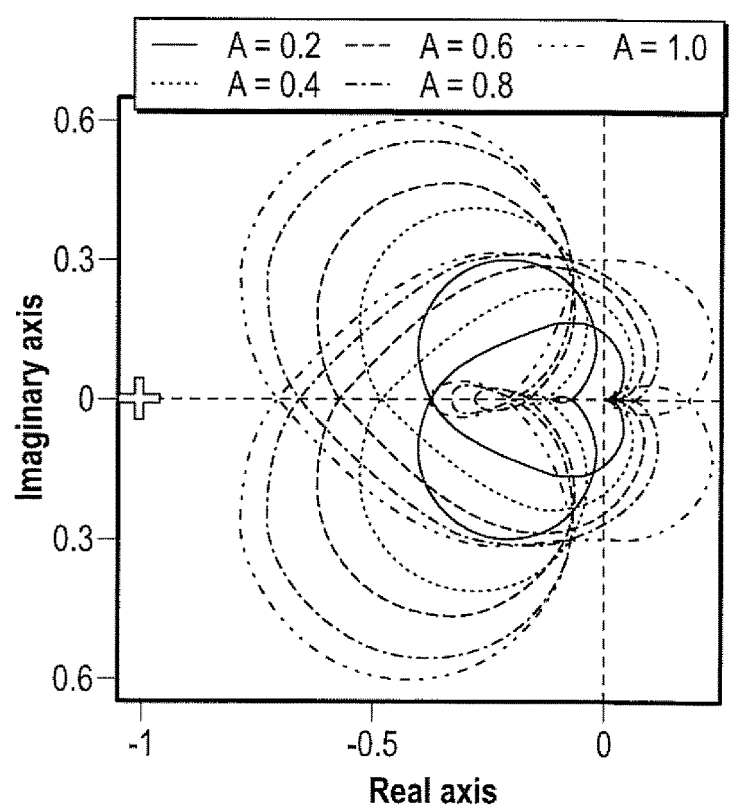
Figure 12A:
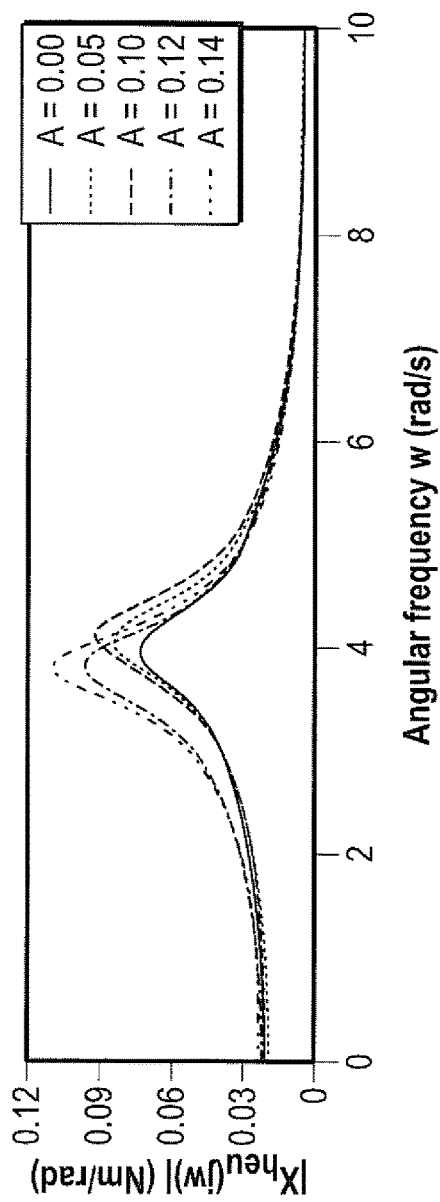
FIGS. 12A-12B are illustrative graphs showing the integral admittance magnitude $|X_{heu}(j\omega)|$ (FIG. 12A) and integral admittance phase $\angle X_{heu}(j\omega)$ (FIG. 12B) for a coupled human-exoskeleton system with optimal control parameters that achieve coupled stability and passivity in accordance with one aspect of the present application.
Figure 12B:
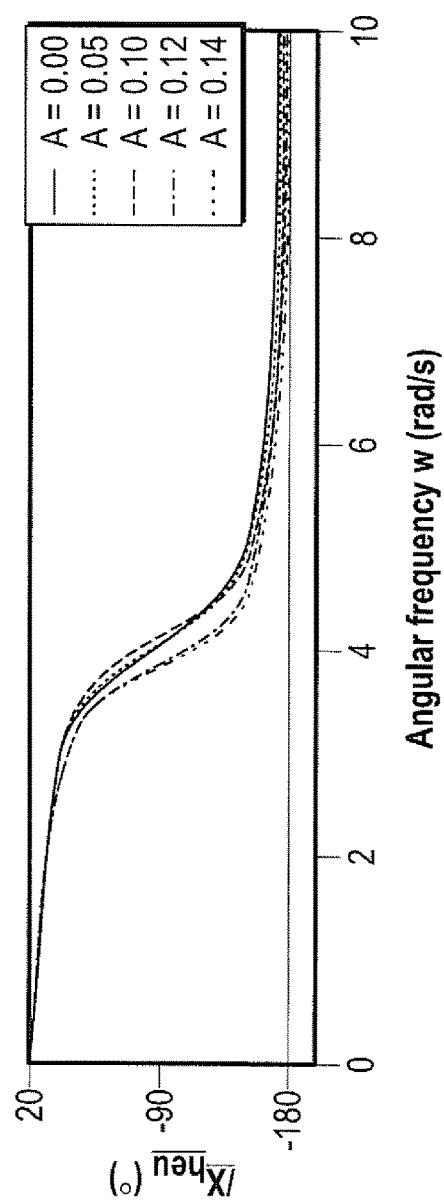
Figure 13A:
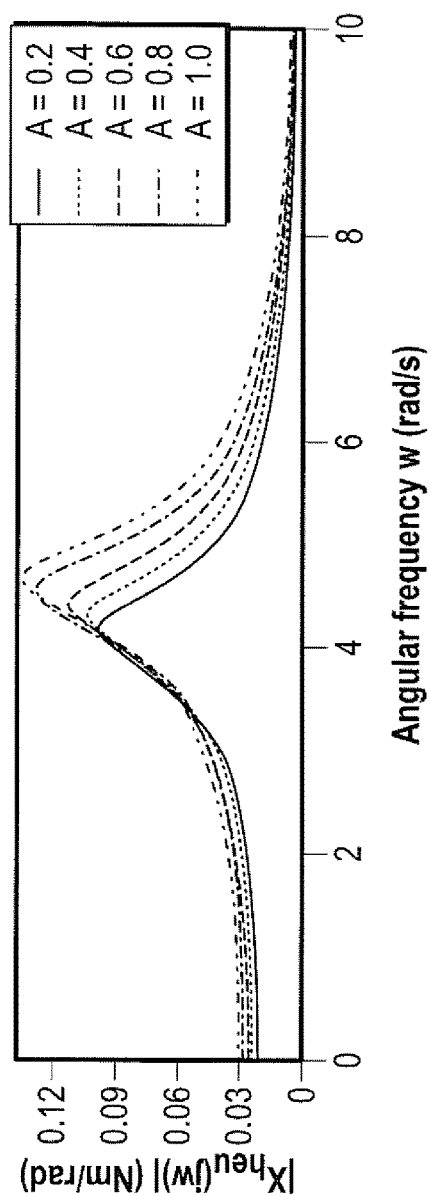
FIGS. 13A-13B are illustrative graphs showing the integral admittance magnitude $|X_{heu}(j\omega)|$ (FIG. 13A) and integral admittance phase $\angle X_{heu}(j\omega)$ (FIG. 13B) for a coupled human-exoskeleton system with optimal control parameters that achieve coupled stability but does not achieve coupled passivity in accordance with one aspect of the present application.
Figure 13B:
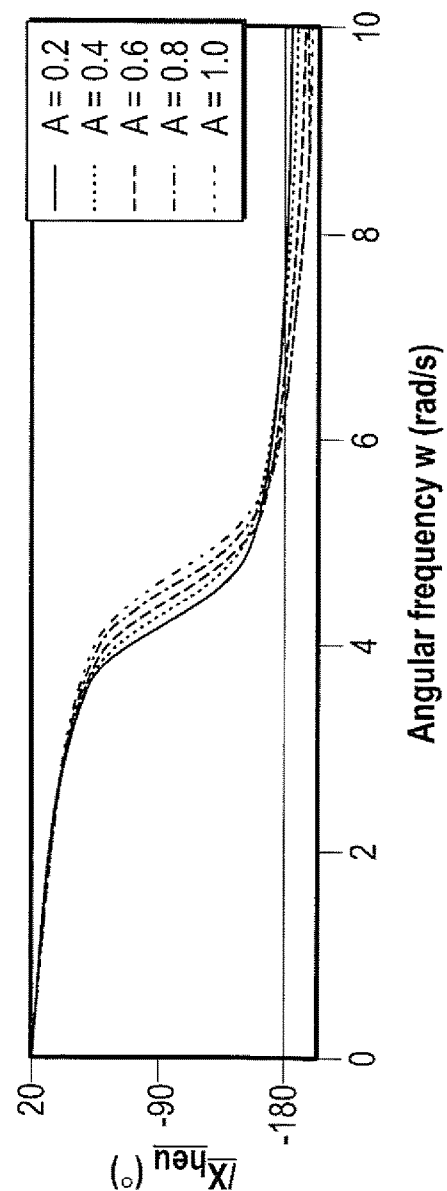
Figure 14A:
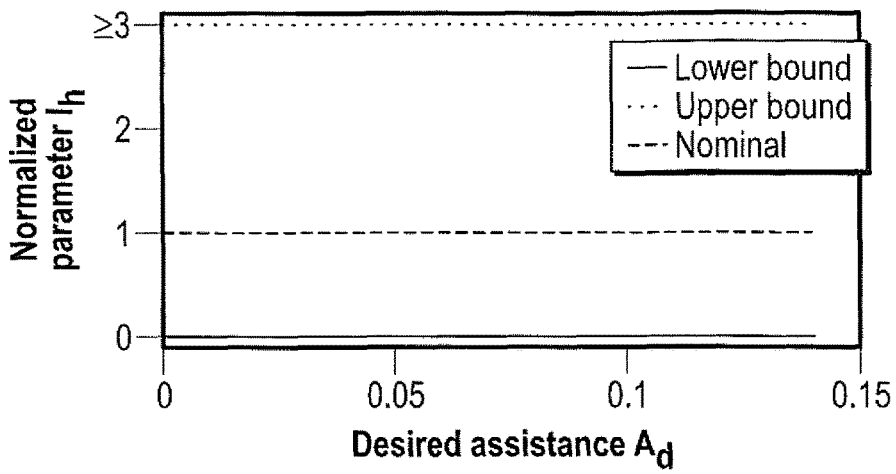
FIGS. 14A-14H are illustrative graphs showing lower and upper bounds of variations in the different normalized system parameters that a coupled human-exoskeleton system may handle while achieving coupled stability and passivity in accordance with one aspect of the present application.
Figure 14B:
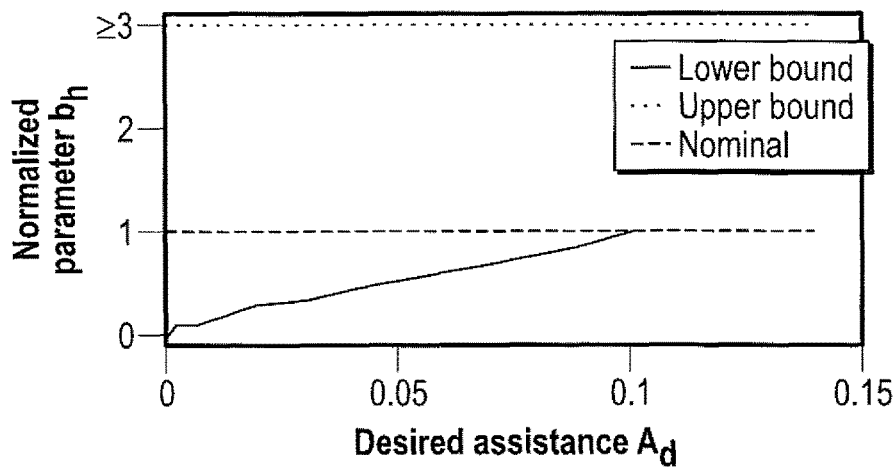
Figure 14C:
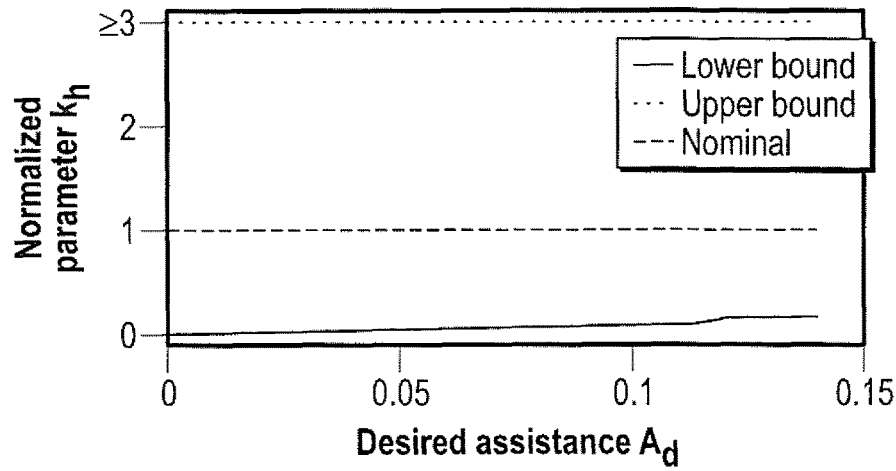
Figure 14D:
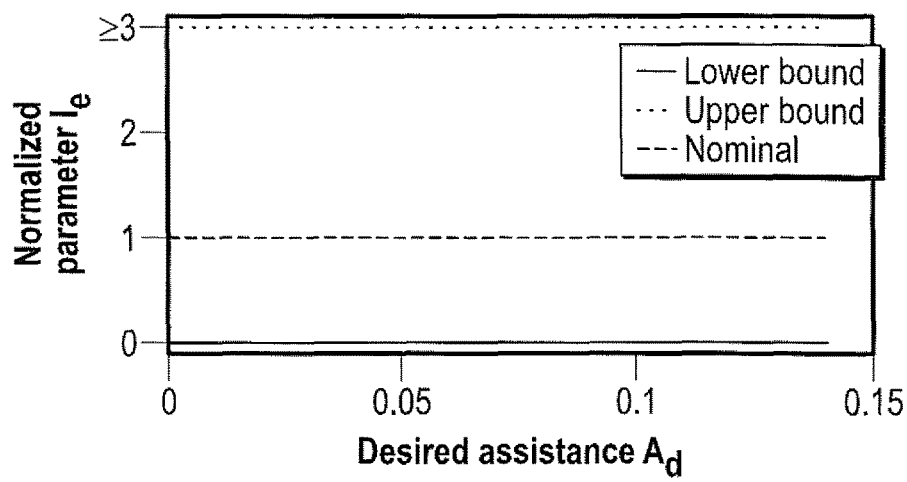
Figure 14E:
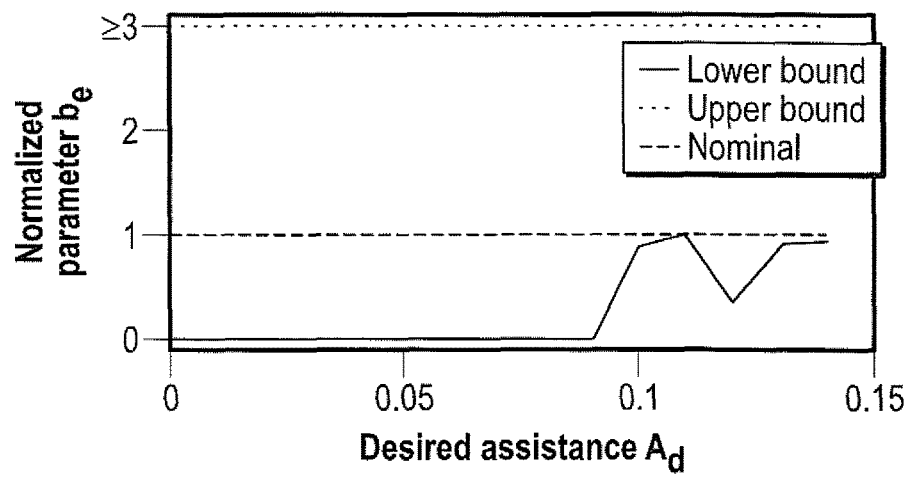
Figure 14F:
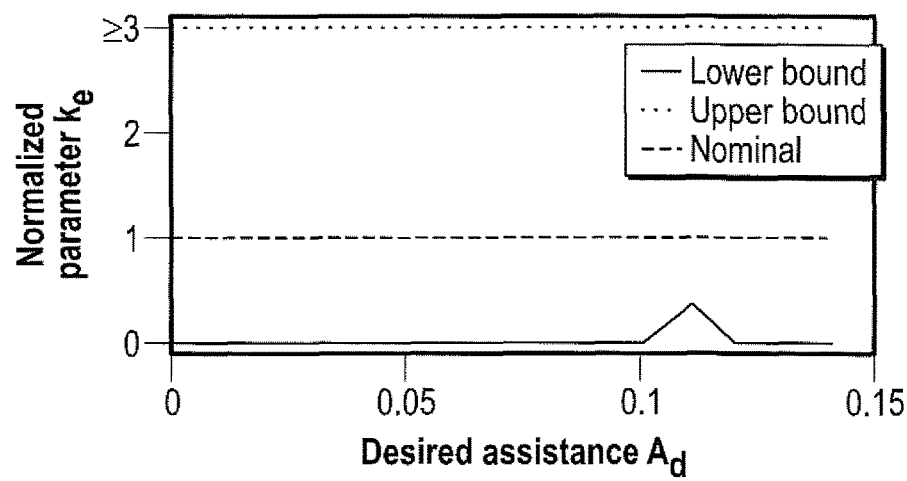
Figure 14G:
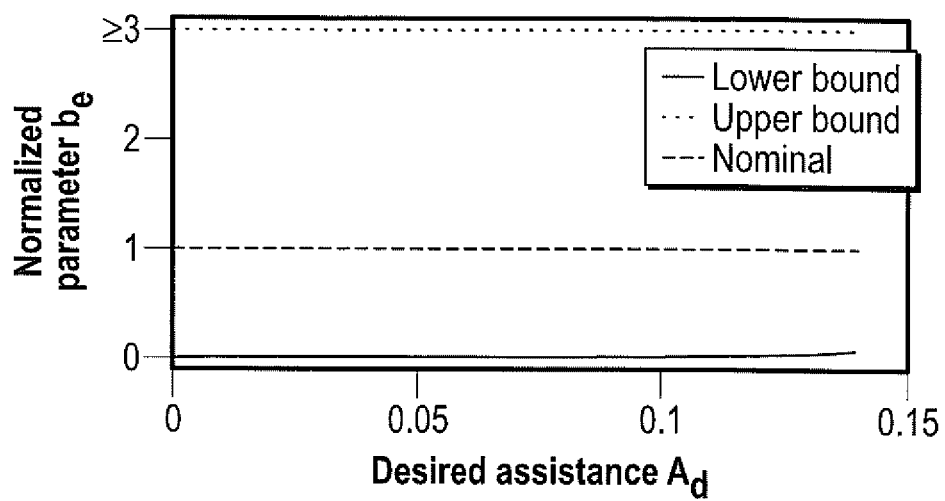
Figure 14H:
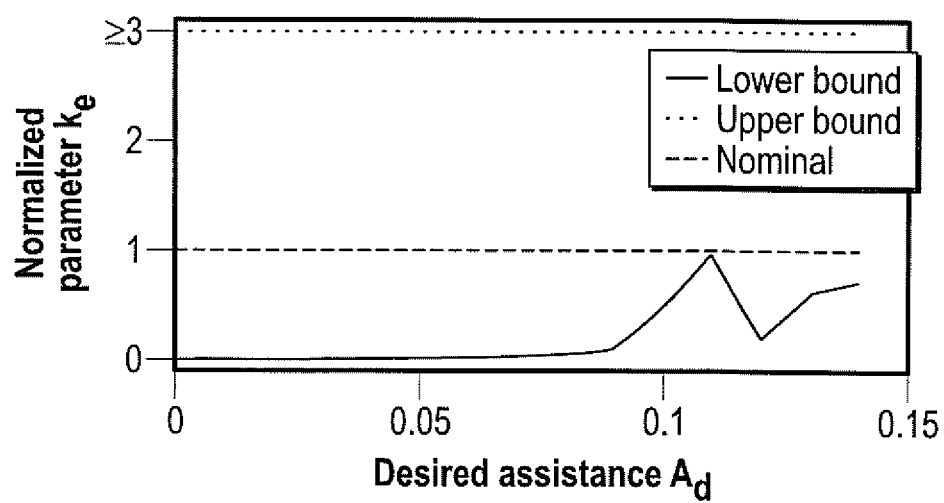

FIGS. 11A-11B shows the Nyquist plots of $-L_{heu}(s)$ corresponding to some of the optimal control parameters shown in FIGS. 10A-10D. None of the Nyquist plots encircle $-1+j0$, thereby emphasizing that the derived coupled human-exoskeleton systems are all stable irrespective of whether they are passive (FIG. 11A) or active (FIG. 11B). The integral admittance magnitude and phase plots of some of the derived coupled human-exoskeleton systems that satisfy the passivity constraint may be seen in FIGS. 12A-12B, while some of those that do not satisfy the passivity constraint may be seen in FIGS. 13A-13B. It may be seen from FIG. 13A that the magnitude response peak shifts to the right with an increase in desired assistance ratio similar to the ones in FIG. 12A for $A_d \leq 0.1$. However, for $A_d$>0.1, the passivity constraint shifts the magnitude response peak to the left as shown in FIG. 12A which may be indicative of the deviation in the control parameters in FIGS. 10A-10D. It may be seen from FIG. 12B that the coupled systems whose phase plots are shown satisfy the passivity condition in Equation 19, whereas FIG. 13B show the phase plots of the coupled systems that do not satisfy the passivity condition.

FIGS. 9-13B show the optimization results with and without the passivity constraint in order to understand the effect of adding the passivity constraint. Although the passivity constraint m ay reduce the level of assistance ($A \leq 0.1422$) that may be achieved with an exoskeleton, it still is essential so that the coupled human-exoskeleton system remains stable while interacting with any passive environment (J. E. Colgate and N. Hogan, "An analysis of contact instability in terms of passive physical equivalents," in Proc. IEEE Int. Conf. Robotics and Automation (ICRA), 1989, pp. 404-409.). For example, a leg exoskeleton that stably amplifies the human leg motion but becomes unstable when the leg interacts with the ground is undesirable.

An exoskeleton controller should be robust to uncertainties in the human parameters $\{I_h, b_h, k_h\}$, the exoskeleton parameters $\{I_e, b_e, k_e\}$ and the coupling parameters $\{b_c, k_c\}$. A concern is that the closed-loop coupled human-exoskeleton system should be robustly stable and passive to parameter uncertainties, i.e., the closed-loop coupled human-exoskeleton system should be stable and passive for a sufficiently large range of parameter variations. FIGS. 14A-14H presents the lower and upper bounds of the normalized parameters $\{\hat{I}_h, \hat{b}_h, \hat{k}_h, \hat{I}_e, \hat{b}_e, \hat{k}_e, \hat{b}_c, \hat{k}_c\}$ for which the coupled system is stable and passive using the control parameters in FIGS. 10A-10D that satisfy the passivity constraint. The nominal parameter values used in the optimization result in normalized parameter values of unity. It is to be noted that in each case, one parameter is varied and the rest of the parameters are maintained at their nominal values.

In FIGS. 14A-14H, the upper bound is visually limited to 3 (300%) and any upper bound$\geq 3$ is considered identical visually. All the upper bounds in FIGS. 14A-14H are in actuality$\geq 10^5$, which is significantly larger than 3. This may indicate that even if the human limb gets stiffer, damper or heavier, the coupled human-exoskeleton system will continue to be stable. This may indicate that underestimating the parameters is better than overestimating in terms of robust stability and passivity because it is the lower bound that increases with increased assistance, while the upper bound remains large. However, it should be noted that although stability and passivity are achieved, the desired assistance may not be achieved as will be discussed below.

It may be seen from FIGS. 14A-14H that the coupled human-exoskeleton system may have large robust stability and passivity margins for variations in the moment of inertia and joint stiffness coefficient of both the human and the exoskeleton, and the coupling damping coefficient i.e., $\{I_h, k_h, I_e, k_e, b_c\}$. However, the coupled system may have negligible robust stability and passivity margins for variations in the damping coefficients $b_h$, $b_e$ and the coupling stiffness coefficient $k_c$ for desired assistance ratio $A_d \geq 0.1$. The human joint damping coefficient $b_h$ appears to be the parameter that affects coupled stability and passivity to any significant extent for $A_d < 0.1$. Overall, the coupled human-exoskeleton system that provides lower assistance is robustly more stable and passive than the one providing higher assistance.

While robust stability and passivity are concerns in exoskeleton control design, the performance of the controller should not be largely compromised with parameter uncertainties. In order to evaluate robust performance, one needs to define the performance criteria, which are considered satisfactory. In embodiments of the present disclosure, a controller is said to have robust performance if the resulting absolute variation in desired assistance ratio and resistance ratio are within 2%, i.e., $\Delta A \leq 0.02$ and $\Delta R \leq 0.02$.

FIGS. 15A-15H depicts the lower and upper bounds of the normalized parameters $\{\hat{I}_h, \hat{b}_h, \hat{k}_h, \hat{I}_e, \hat{b}_e, \hat{k}_e, \hat{b}_c, \hat{k}_c\}$ for which the coupled system is robustly performing using the optimal control parameters in FIGS. 10A-10D. It should be noted that the parameter variations that are robustly stable and passive from FIGS. 14A-14H are considered here, and when one parameter is varied, the other parameters are maintained at unity. Just like in FIGS. 14A-14H, the upper bound of the parameter variations in FIGS. 15A-15H are visually limited to 3, and any variation$\geq 3$ is considered identical visually.

Figure 15A:
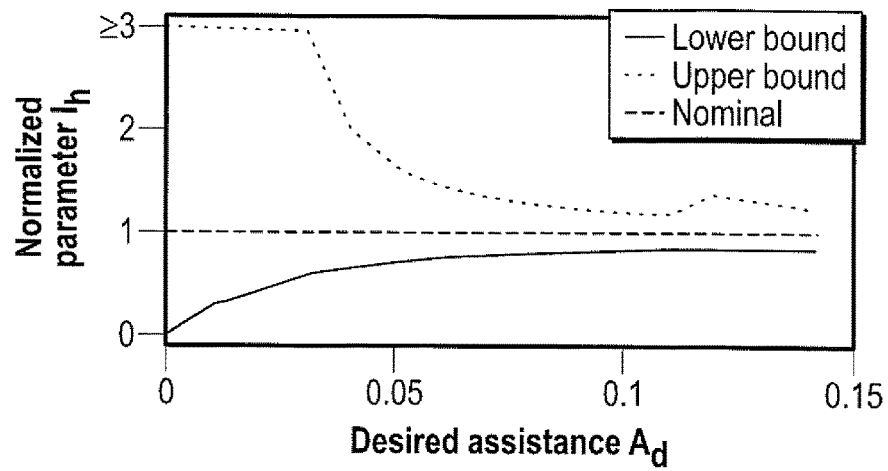
FIGS. 15A-15H are illustrative graphs showing lower and upper bounds of variations in the different normalized system parameters that the coupled human-exoskeleton system may handle while achieving the desired assistance ratio and resistance ratio within a tolerance of 2%, i.e., $\Delta A \leq 0.02$ and $\Delta R \leq 0.02$ in accordance with one aspect of the present application.
Figure 15B:
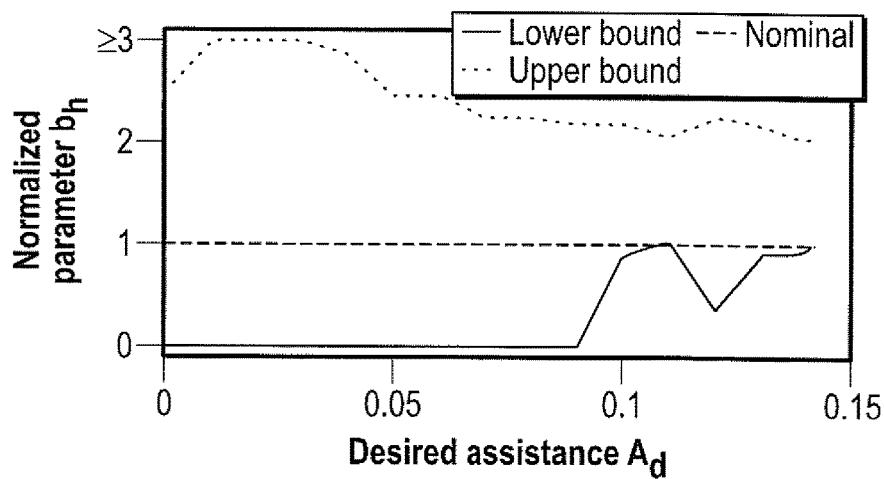
Figure 15C:
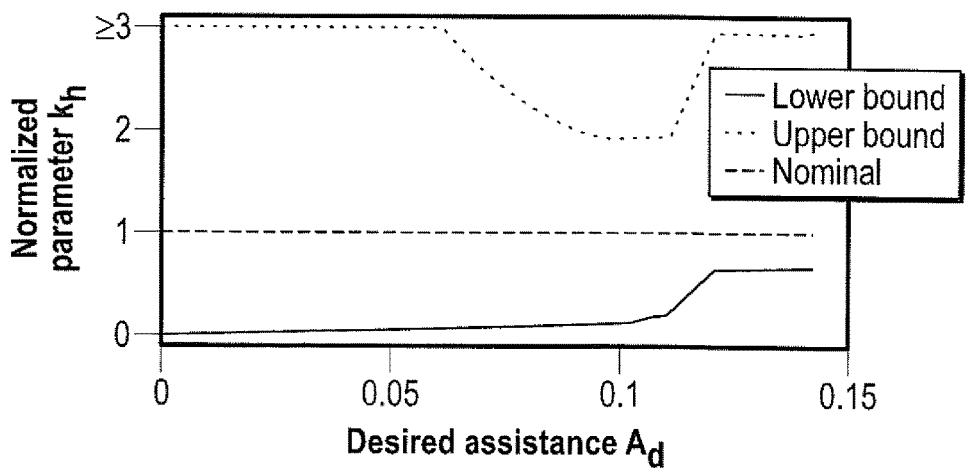
Figure 15D:
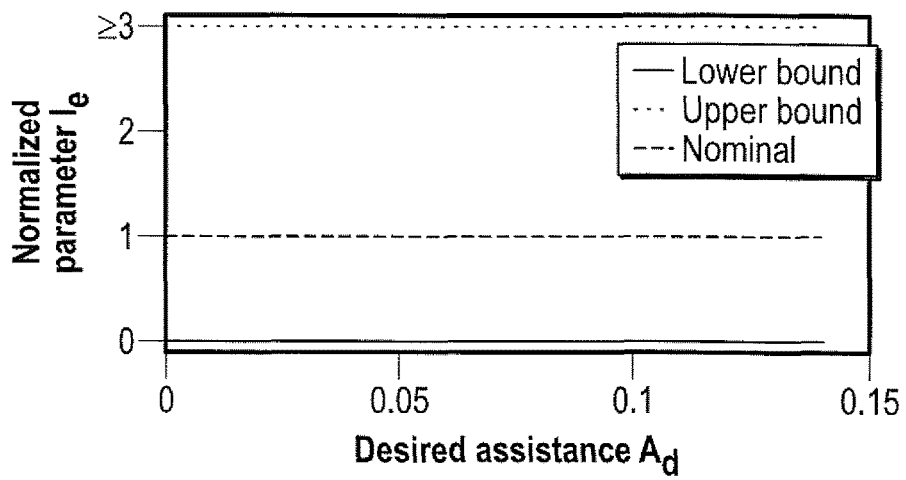
Figure 15E:
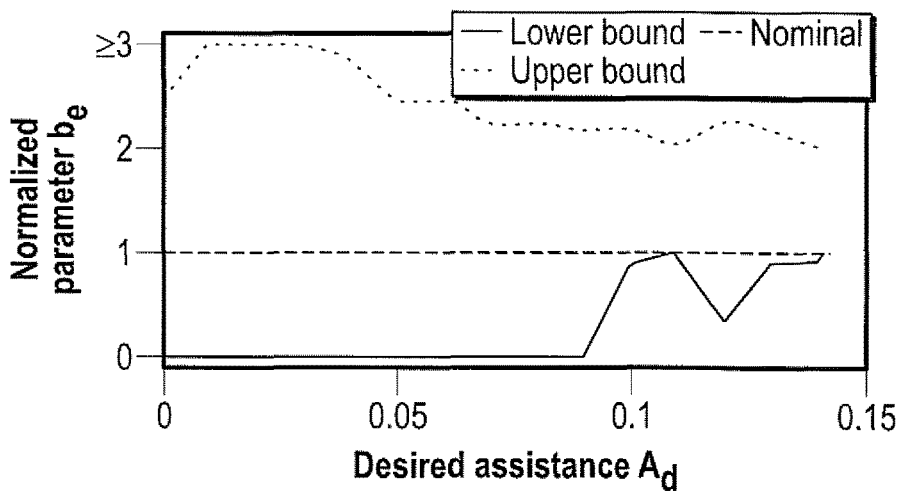
Figure 15F:
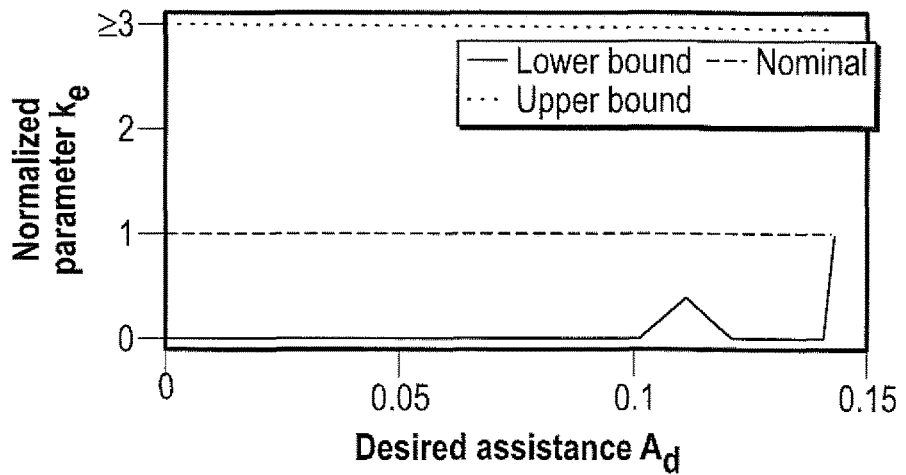
Figure 15G:
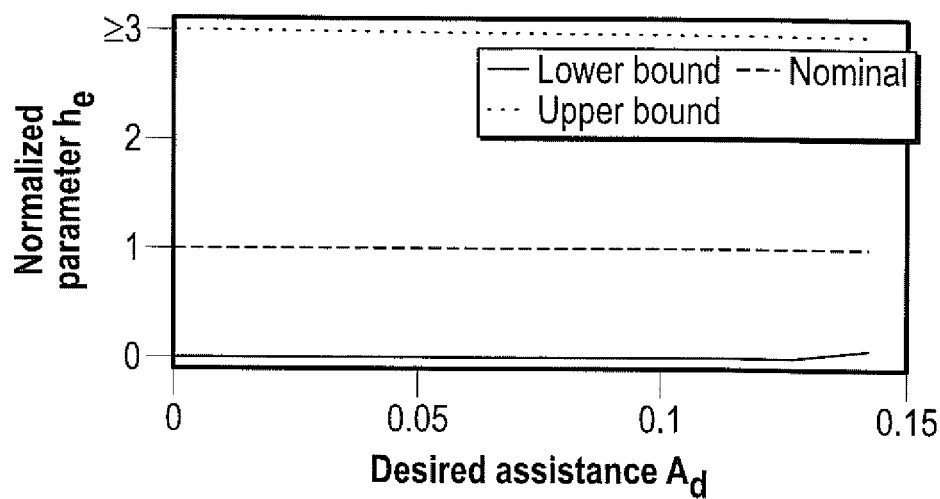
Figure 15H:
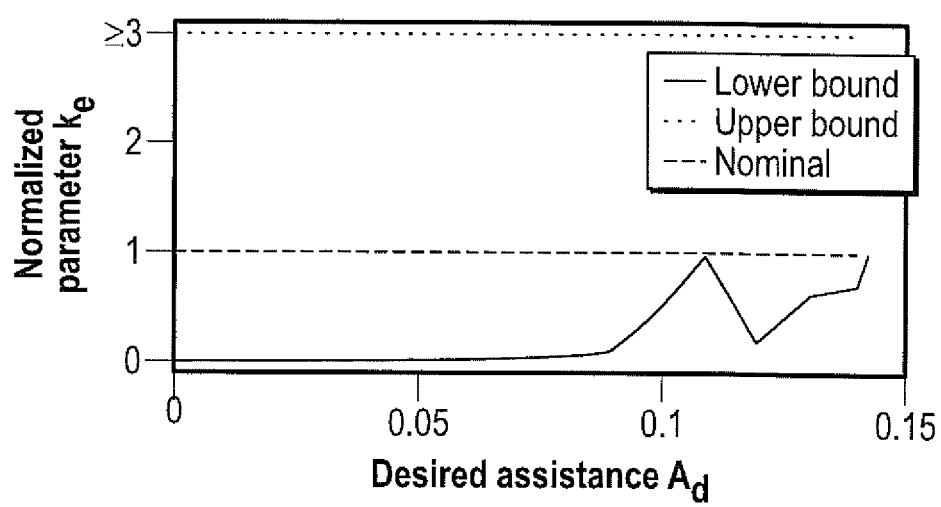
Figure 16A:
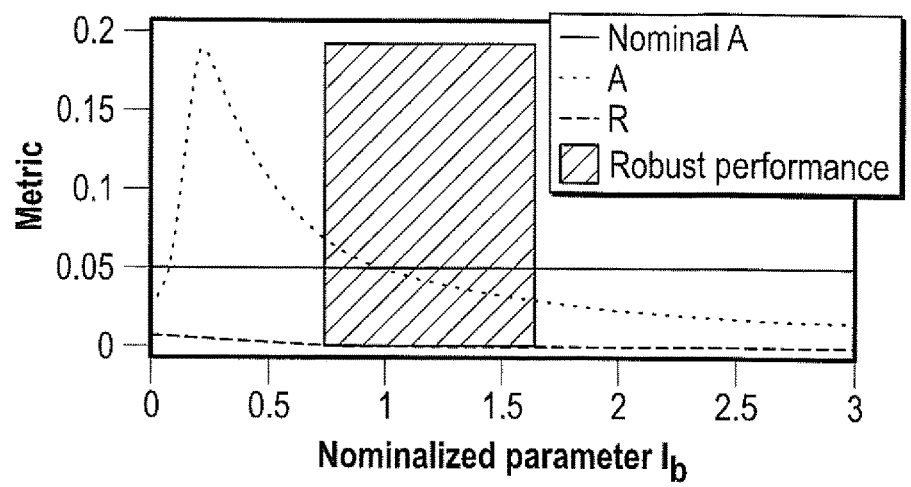
FIGS. 16A-16H are illustrative graphs showing the variation of the achieved assistance ratio A and resistance ratio R with the variation of the different system parameters for the coupled human-exoskeleton system with the optimal control parameters corresponding to a desired assistance ratio $A_d=0.05$ in accordance with one aspect of the present application.
Figure 16B:
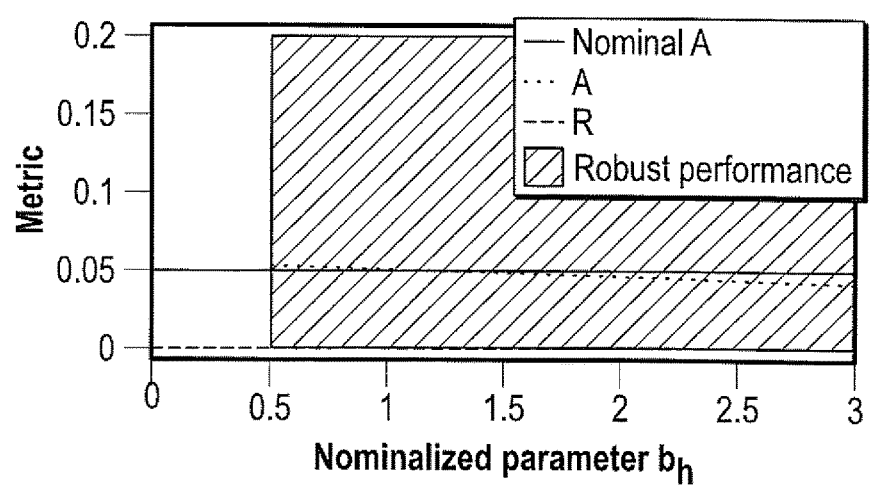
Figure 16C:
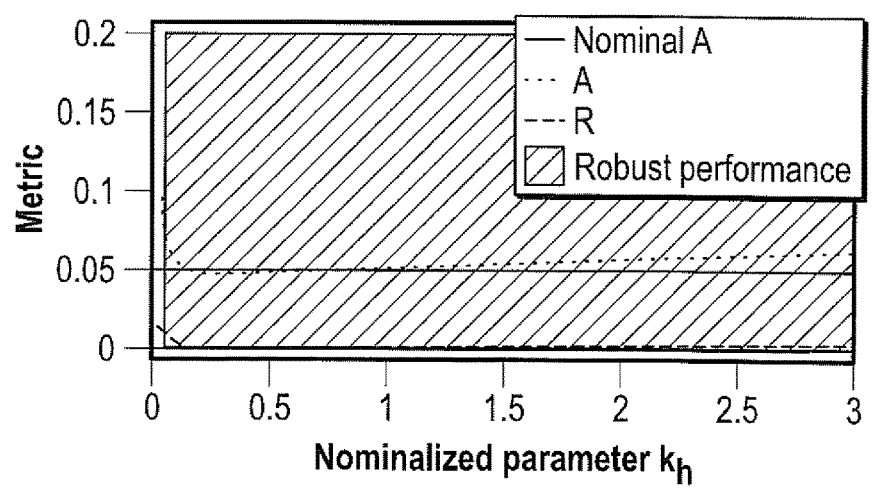
Figure 16D:
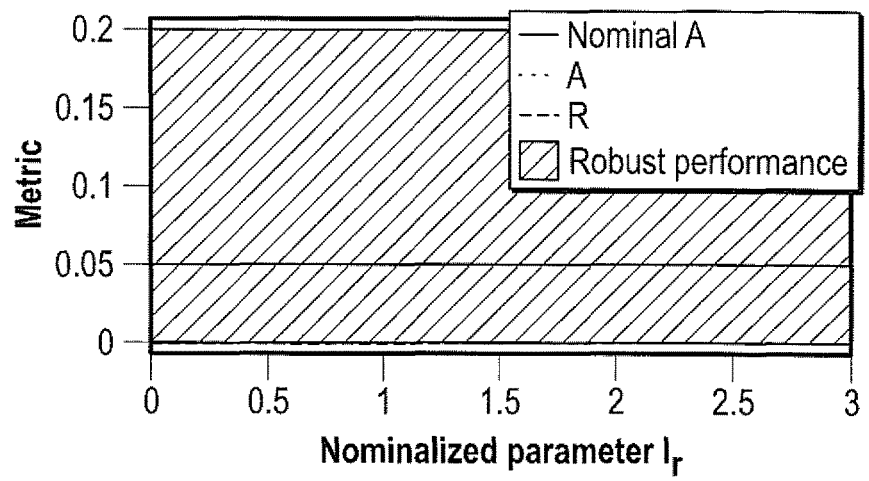
Figure 16E:
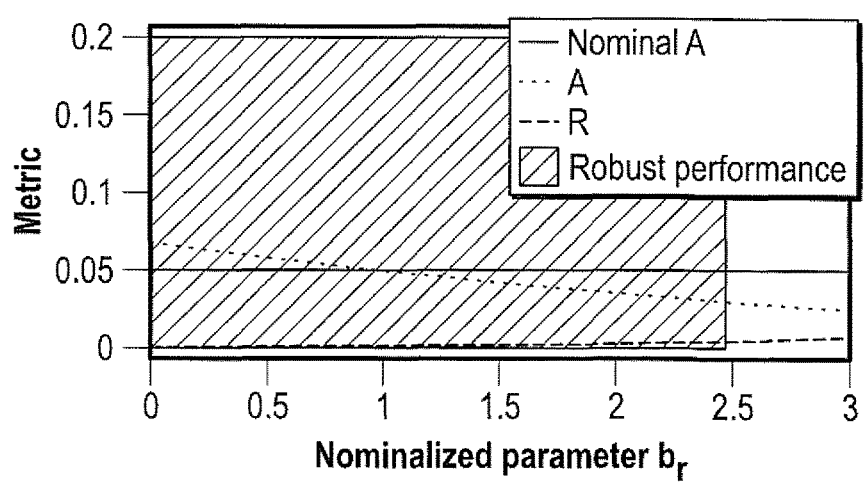
Figure 16F:
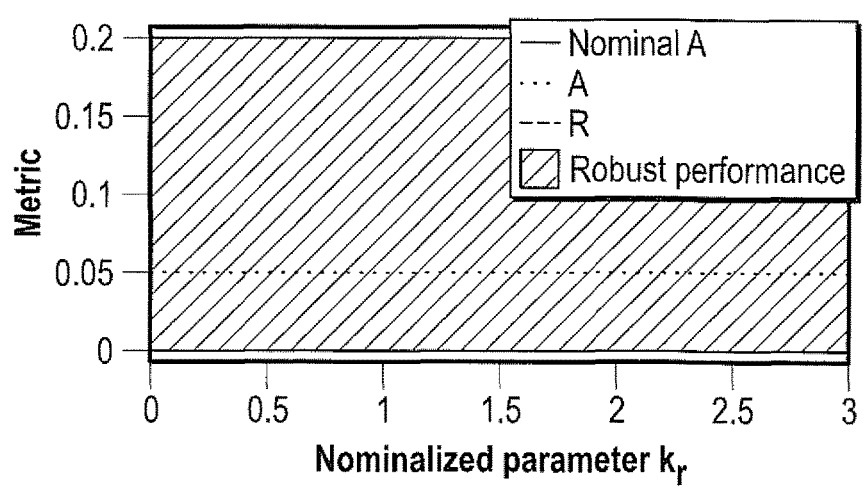
Figure 16G:
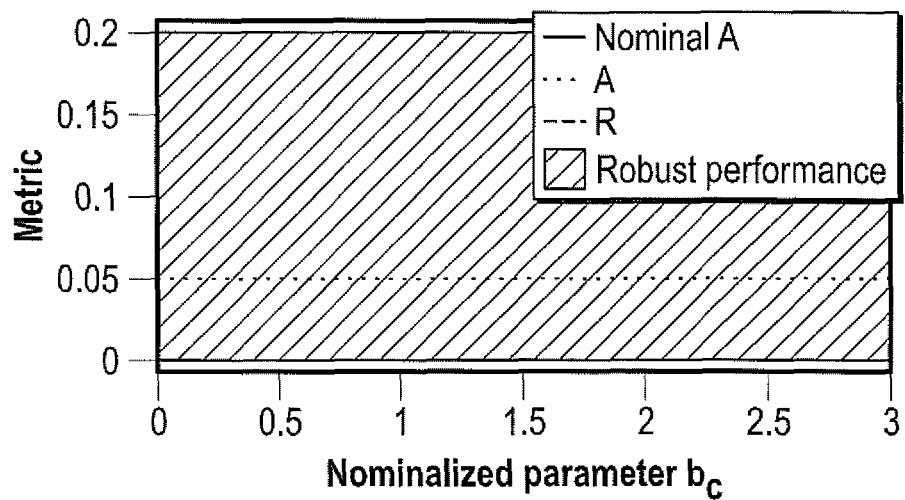
Figure 16H:
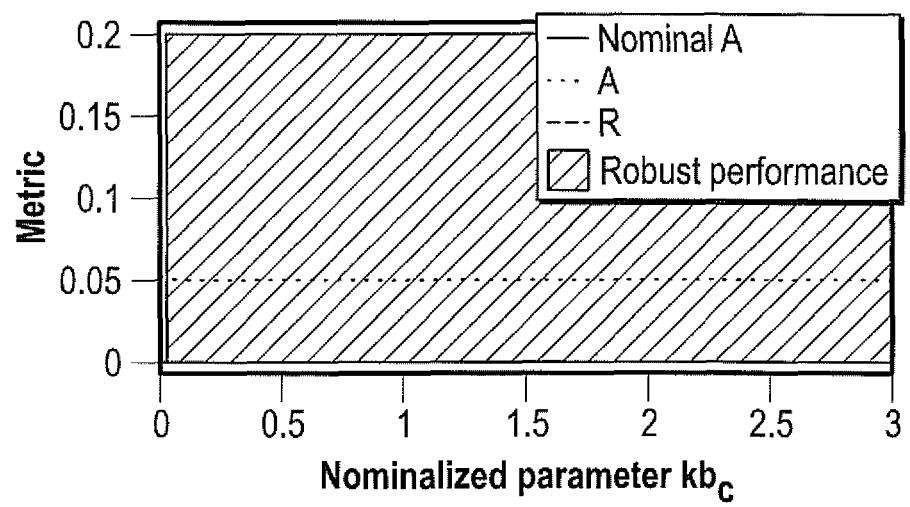

It may be seen from FIGS. 15D, 15F and 15G that the closed-loop coupled human-exoskeleton system is robustly performing against variations in the exoskeleton moment of inertia $I_e$, joint stiffness coefficient $k_e$ and the coupling damping coefficient $b_c$. The human joint stiffness coefficient $k_h$, the exoskeleton joint damping coefficient $b_e$ and the coupling stiffness coefficient $k_c$ may affect the performance of the exoskeleton for desired assistance ratios $A_d \geq 0.1$ as shown in FIGS. 15C, 15E and 15H respectively. FIGS. 15A and 15B show that the human parameters $I_h$, $b_h$ appear to be the most sensitive to parameter variations especially at desired assistance ratios $A_d \geq 0.1$.

FIGS. 16A-16H shows the robustly performing parameter variations for a desired assistance ratio $A_d = 0.05$. The assistance ratio A and resistance ratio R for all stable parameter variations in [0, 3] are also shown along with the nominal A. It may be seen from FIG. 16A that the human moment of inertia $I_h$ limits the robust performance margin the most with a variation of 72.9% to 163.4%. It may be seen from FIG. 16D and FIGS. 16F-16H the controller for $A_d = 0.05$ may achieve robust performance for the whole range of parameter variation of interest.

Figure 17:
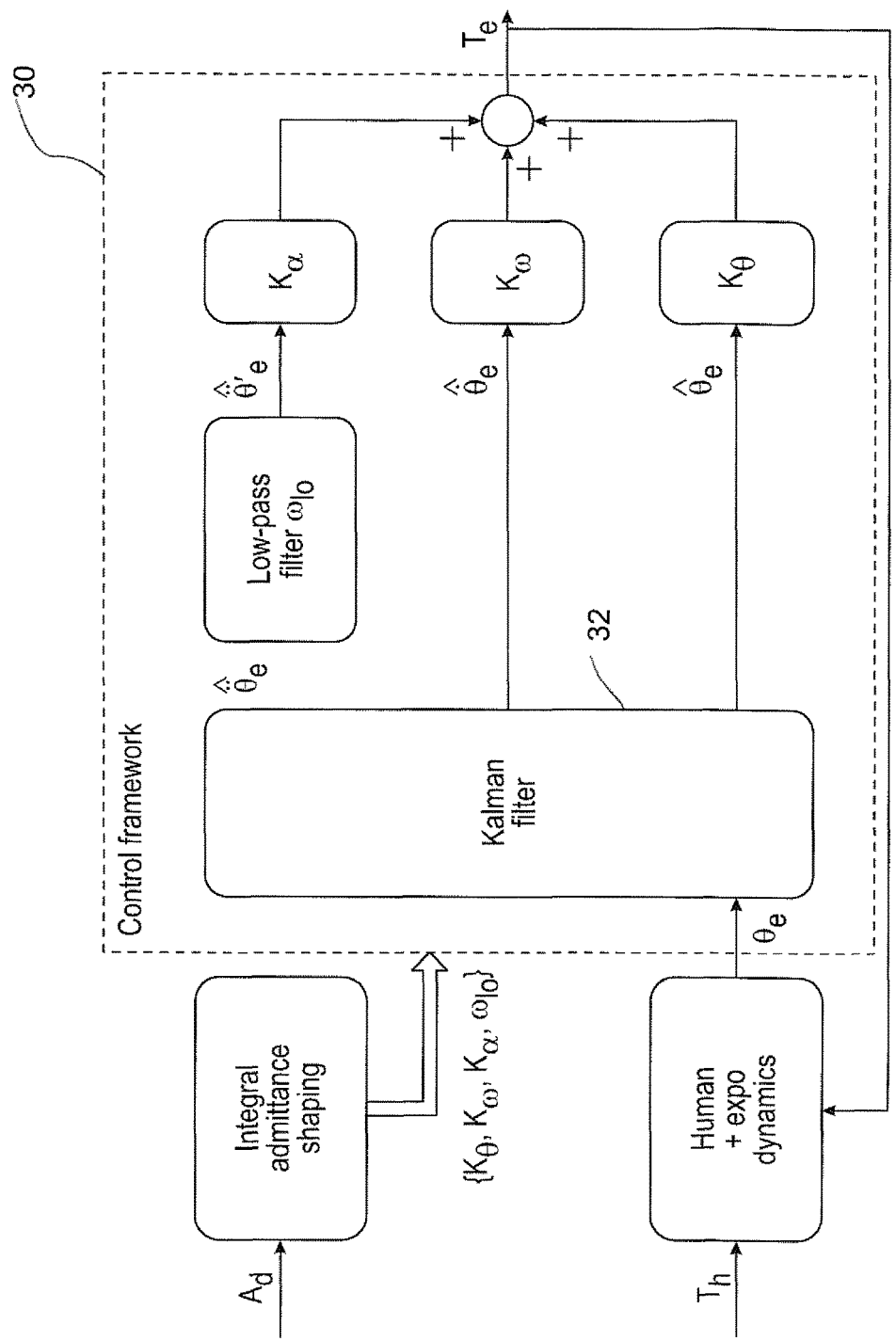
FIG. 17 is a block diagram showing a control framework for executing exoskeleton control in accordance with one aspect of the present application.

FIG. 17 shows a control framework 30 that executes the exoskeleton control using the optimized control parameters from integral admittance shaping all of which was disclosed above. As may be seen in FIG. 17, a Kalman filter 32 may be used to estimate the exoskeleton joint angle $\theta_e$, angular velocity $\dot{\theta}_e$ and angular acceleration $\ddot{\theta}_e$ needed to implement the control law in Equation 31. In embodiments of the present disclosure, the Kalman filter implementation may be based on an article by P. Canet, "Kalman filter estimation of angular velocity and acceleration: On-line implementation," McGill University, Montreal, Canada, Tech. Rep. TR-CIM-94-15, November 1994.

Figure 18:
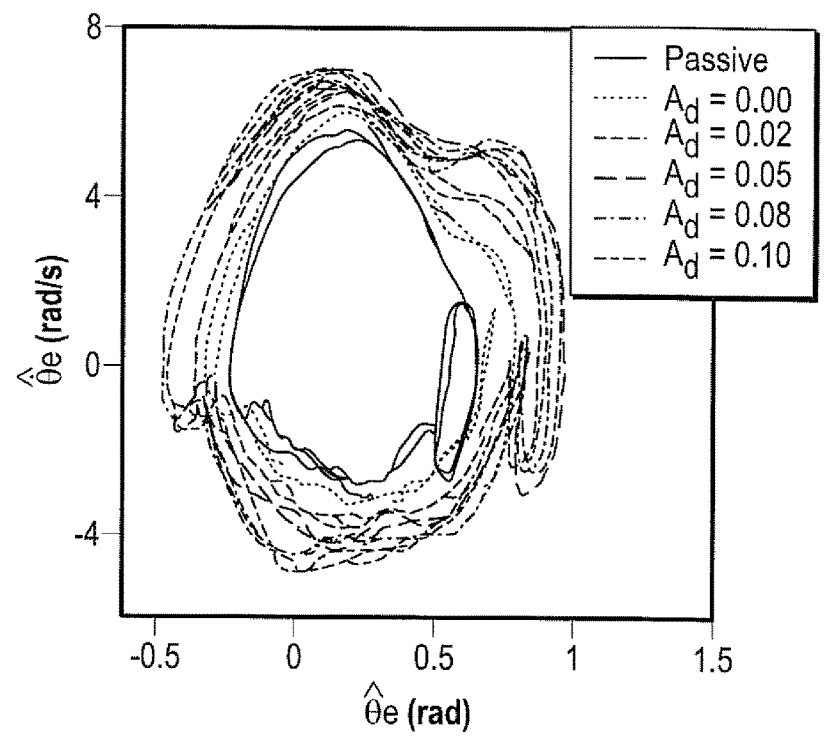
FIG. 18 is an illustrative graph showing hip joint phase plots ($\hat{\theta}_e$ vs $\hat{\theta}_e$) for different desired assistance ratios in accordance with one aspect of the present application.

FIG. 18 shows hip joint phase plots ($\dot{\theta}_e$ vs $\theta_e$) for six different cases, namely, passive device with no assist, zero desired assist, i.e., $A_d = 0(|X_{heu}(j\omega)| = |X_h(j\omega)|)$, and four non-zero desired assists ($A_d = 0.02, 0.05, 0.08, 0.1$). Their corresponding exoskeleton torque trajectories may be seen in FIG. 19. In each case, the human subject was instructed to walk at their normal pace. As may be seen from FIG. 18, the phase plot corresponding to $A_d = 0$ is bigger than that with just the passive exoskeleton. This confirms that the passive exoskeleton weighs the human leg down and shrinks its phase plot, whereas with $A_d = 0$, the active exoskeleton is able to recover the human's original joint dynamics. Moreover, it can be seen from FIG. 18 that the phase plot grows with increasing assistance from $A_d = 0$ to $A_d = 0.05$. Therefore, the integral admittance shaping control framework amplifies the motion of the hip joint, and the level of amplification increases with increasing assistance.

Figure 19:
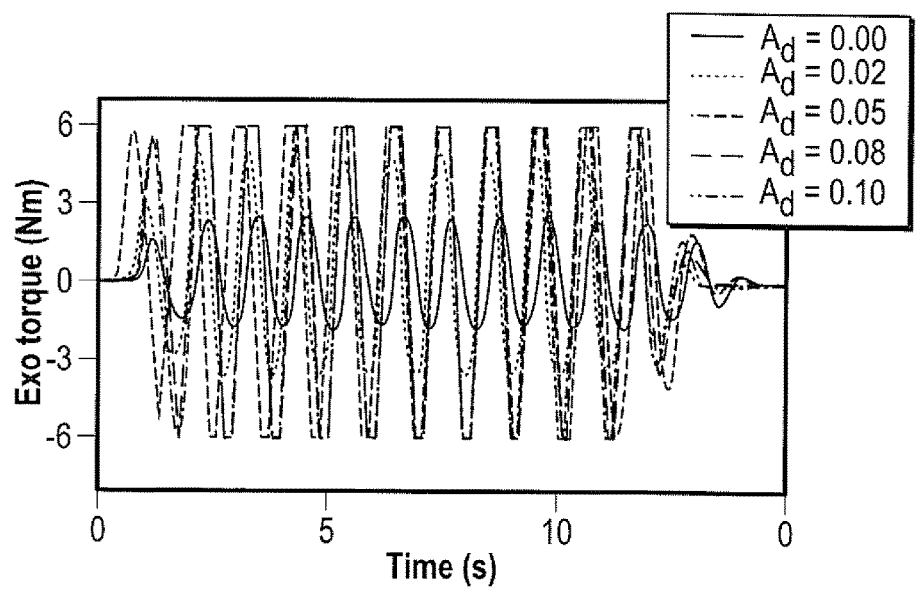
FIG. 19 is an illustrative graph showing exoskeleton joint torque trajectories for different desired assistance ratios in accordance with one aspect of the present application.

However, the phase plots may begin to saturate after $A_d = 0.05$. The reason for this behavior is that the exoskeleton torque trajectories may begin saturating at $A_d = 0.05$ as shown in FIG. 19.

Embodiments of the present disclosure present conceptual and quantitative definitions of assistance and resistance based on the frequency response of the integral admittance of 1-DOF joint exoskeleton devices. An exoskeleton may be considered assistive if it increases the admittance of the coupled human-exoskeleton system resulting in motion amplification and torque reduction. Embodiments of the present disclosure use Integral Admittance Shaping to shape the frequency response magnitude profile of the integral admittance of the coupled human-exoskeleton joint such that the desired assistance may be achieved. It may ensure that the coupled system is stable and passive, which ensures stable interaction with passive environments. Integral admittance shaping was formulated as a constrained optimization problem with the objective of finding the optimal exoskeleton control parameters that achieve the desired assistance, zero resistance and satisfy stability and passivity constraints.

Figure 20:
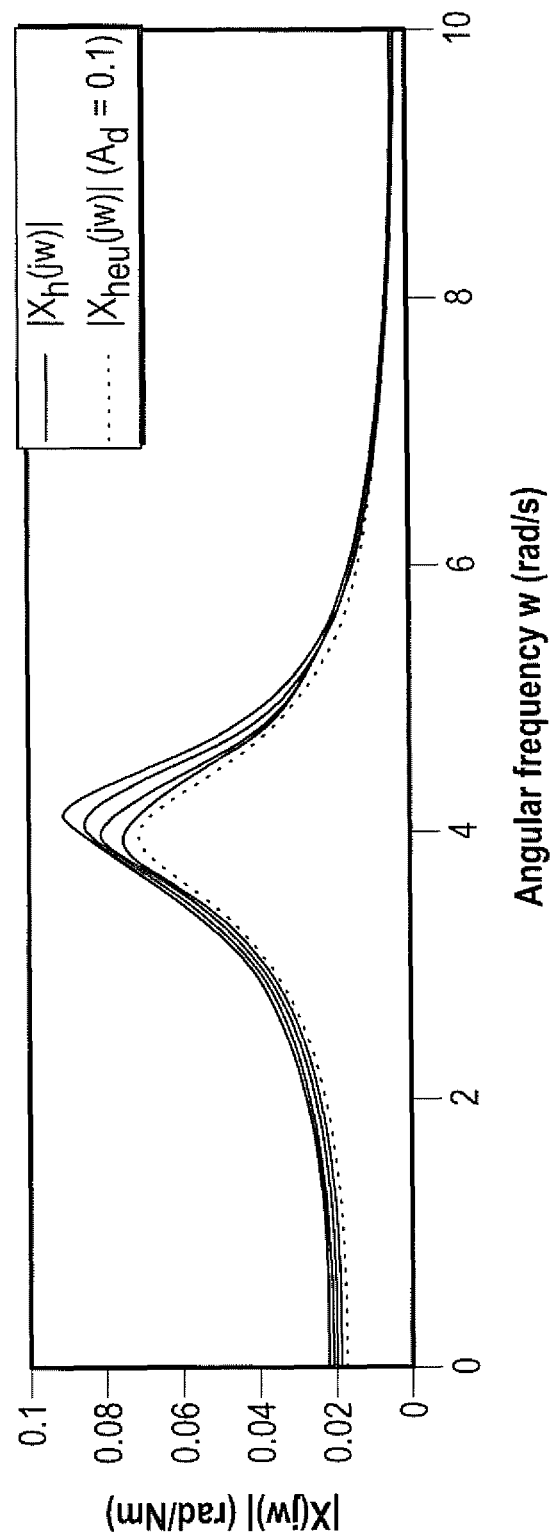
FIG. 20 is an illustrative graph showing multiple integral admittance shapes that achieve the same assistance ratio $A_d=0.1$ while guaranteeing coupled stability and passivity in accordance with one aspect of the present application.

It should be noted that there are infinite shapes that may produce the same assistance ratio as shown in FIG. 20, and choosing between these shapes is non-trivial. For the results presented in FIG. 10, the optimal control parameters for $A_d=0$ ($|X_{heu}(j\omega)|=|X_h(j\omega)|$) were first obtained, and then the optimal control parameters for $A_d$ were chosen as the initial optimization parameters for $A'_d=A_d+0.01$. Therefore, the optimization in Equation 34 converges to the closest control parameters from those that match the unassisted human integral admittance's magnitude curve.

However, for the same desired assistance, the user may use other metrics and even other constraints to pick from the set of infinite solutions. For example, similar to the constraint on damping ratio in Equation 33, constraints on natural frequency and resonant peak magnitude may also be added to Equation 33 to restrict the set of possible solutions.

Embodiments of the present disclosure present conceptual and quantitative definitions for assistance and resistance, and used these definitions to find appropriate shapes for the frequency response magnitude of the integral admittance of the coupled human-exoskeleton system. However, these definitions of assistance and resistance in no way restrict the utility of the integral admittance shaping framework.

Integral admittance shaping is a general framework that may find optimal control parameters for the exoskeleton system that shape the integral admittance of the coupled system. This shape may be provided by the user too. For example, the user might want to achieve an increase in natural frequency while maintaining the same damping ratio and resonant peak magnitude of the unassisted human as shown in FIG. 6. It is to be noted that in this ease, the resistance ratio will be non-zero, i.e., R=0, and the constraint on the resistance ratio in Equation 33 may be removed to accommodate it. Since the desired integral admittance magnitude shape is provided in this case, the optimization in Equation 33 may also be modified to achieve the desired shape rather than achieve the desired assistance as presented above.

Moreover, the exoskeleton control transfer function presented in Equation 31 does not restrict the integral admittance shaping procedure either. Any exoskeleton control law may be used and its parameters may be optimized for using the integral admittance shaping framework presented above. However, the coupled stability and passivity conditions presented in Equation 16 and Equation 19 respectively still hold and are important in designing exoskeleton controllers that enable the coupled human-exoskeleton system to stably interact with passive environments.

Inertia compensation may be essential for providing assistance to the humans ("Design of an active one-degree-of-freedom lower-limb exoskeleton with inertia compensation," Int. J. Robotics Research, vol. 30, no. 4, pp. 486-499, 2011; "Inertia compensation control of a one-degree-of-freedom exoskeleton for lower-limb assistance: Initial experiments," IEEE Trans. Neural Syst. Rehabil. Eng., vol. 20, no. 1, pp. 68-77, 2012; and "A one-degree-of-freedom assistive exoskeleton with inertia com-pensation: the effects on the agility of leg swing motion," *Proc. Inst. Mech. Eng. H.*, vol. 225, no. 3, pp. 228-245, 20."). The moment of inertia of the coupled human-exoskeleton system may be reduced below that of the unassisted human if the exoskeleton control emulates a negative moment of inertia for the exoskeleton, i.e., the desired exoskeleton moment of inertia $I^d_c<0$, which may be achieved using positive feedback of joint acceleration $\ddot{\theta}_e$. However, it should be noted that coupled stability is an important requirement for the design of exoskeleton controllers, which should be compromised. The coupled stability requirement may limit the amount of inertia that can be compensated using an exoskeleton controller, and as shown below will find this limit using positive acceleration feedback. In Eq. 28, with no loss of generality, let's assume $b^d_c=b_e$, $k^d_e=ke$. Then, the desired exoskeleton dynamics reduces to that of a pure inertia $I^d_c<0$, and the exoskeleton torque in Eq. 28 reduces to In Equation 28, with no loss of generality, assume $b^d_e=b_e$, $k^d_e=k_e$. Then, the desired exoskeleton dynamics reduces to that of a pure inertia $I^d_e<0$, and the exoskeleton torque in Equation 28 reduces to:

$$\tau_e(t)=K_\alpha \ddot{\theta}_e(t), \quad (35)$$

where $K_\alpha>0$ is the positive acceleration feedback gain given by:

$$K_\alpha=(I_e-I^d_e), \quad (36)$$

Figure 21A:
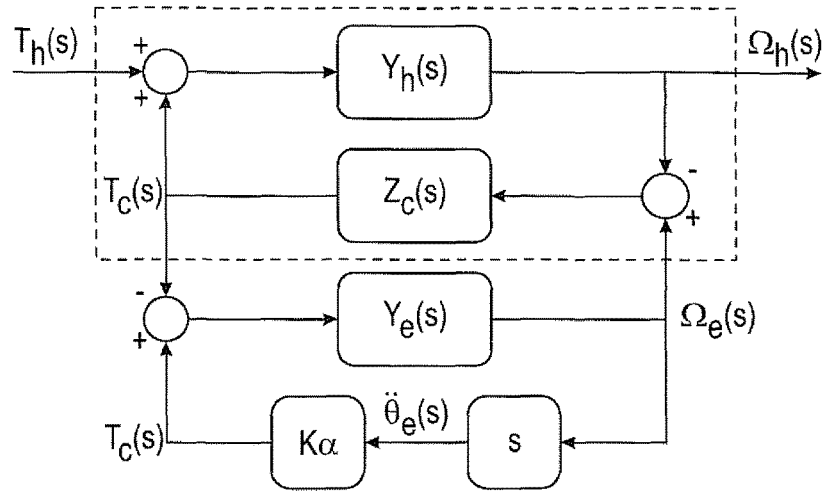
FIGS. 21A-21C are block diagrams of the overall coupled human-exoskeleton system with an acceleration feedback gain $K_\alpha$ in accordance with one aspect of the present application.

With the exoskeleton control law in Equation 35, the control system block diagram in FIG. 5A may reduces to the one in FIG. 21A. In order to evaluate the stability of the coupled system when the exoskeleton behaves like a negative inertia, the block diagram in FIG. 21A should be simplified to find the loop gain of the coupled system as follows.

Figure 21B:
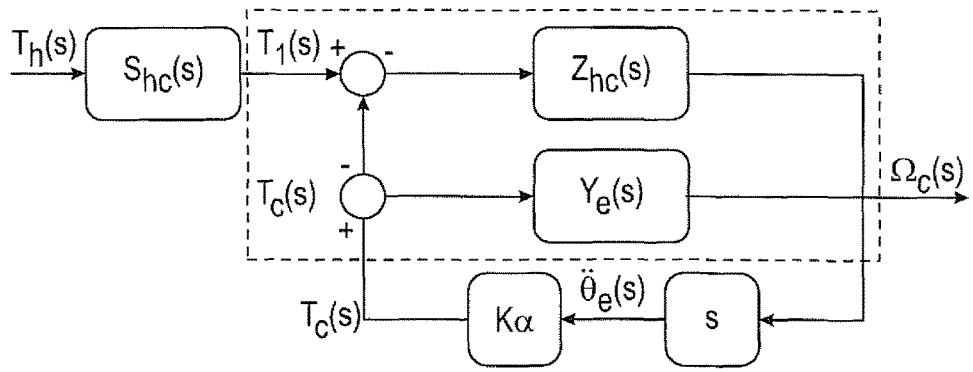

Consider the highlighted region containing $Y_h(s)$ and $Z_c(s)$ in FIG. 21A, which may be thought of as a single block with two inputs, $\tau_h(s)$ and $\omega_e(s)$, and one output $\tau_e(s)$. Using the principle of superposition, one may write:

$$\tau_c(s) = S_{hc}(s)\tau_h(s) + Z_{hc}(s)\Omega_c(s), \quad (37)$$

where $$S_{hc}(s) = \frac{\tau_c(s)}{\tau_h(s)}\bigg|_{\Omega_e=0}, \quad (38)$$

$$= \frac{-Y_h(s)Z_c(s)}{1+Y_h(s)Z_c(s)}.$$

$$Z_{hc}(s) = \frac{\tau_c(s)}{\Omega_e(s)}\bigg|_{\tau_h=0}, \quad (39)$$

$$= \frac{Z_c(s)}{1+Y_h(s)Z_c(s)}.$$

as shown in FIG. 21B.

Figure 21C:
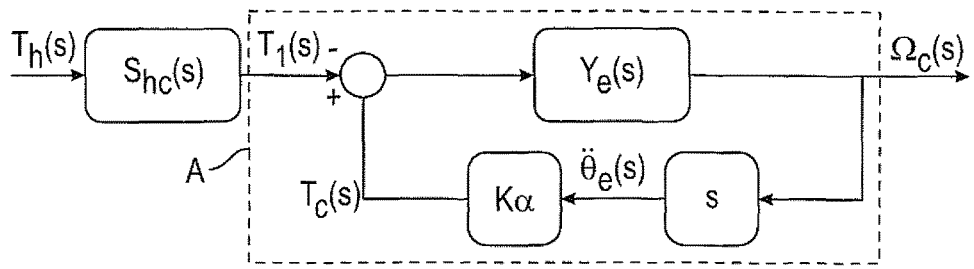

Similarly, consider the highlighted region containing $Z_{he}(s)$ and $Y_e(s)$ in FIG. 21B, which can be thought of as a single block with two inputs, $\tau_e(s)$ and $\tau_1(s)$, and one output $\Omega_e(s)$. Using the principle of superposition, one may write:

$$\Omega_e(s) = Y_{hc}(s)(\tau_e(s) - \tau_1(s)). \tag{40}$$

where $$Y_{he}(s) = \frac{\Omega_e(s)}{\tau_e(s)}\bigg|_{\tau_1=0} \tag{41}$$

$$= \frac{Y_e(s)}{1 + Y_e(s)Z_{he}(s)}.$$

as shown in FIG. 21C.

FIG. 21C represents the same closed-loop linear system in FIG. 21A but with a simpler structure more suitable for stability analysis. Since $S_{hc}(s)$ in Equation 38 depends on the human and coupling parameters, it is generally always stable, and the stability of the closed-loop system depends on the stability of the feedback loop in the A region in FIG. 21C. The transfer function of the loop gain $L_{he}(s)$ used for the stability analysis of this feedback loop is given by:

$$L_{he}(s) = s Y_{he}(s). \tag{42}$$

Since the closed-loop system in region A in FIG. 21C has a positive feedback loop, one should look at gain margin of $-L_{he}(s)$ in Equation 42 to evaluate the stability of the closed-loop system. The gain margin GM of $-L_{he}(s)$ is given by:

$$GM(-L_{he}) = \frac{1}{|-L_{he}(j\omega_c)|}. \tag{43}$$

where $\omega_c$ is the phase-crossover frequency when the phase of $-L_{he}(s)$ is 180°, $\angle L_{he}(j\omega_c) = 180°$. The gain margin GM $(-L_{he})$ gives the maximum positive gain $K_\alpha$ (Equation 36), exceeding which the closed-loop system may become unstable.

In order to determine the phase-crossover frequency, one needs to look into the phase of $-L_{he}(s)$, which is given by:

$$\angle -L_{he}(j\omega) = \angle -Y_{he}(j\omega) + \angle s(j\omega) \tag{44}$$

$$= \angle -Y_{he}(j\omega) + \angle j\omega$$

$$= \angle -Y_{he}(j\omega) + 90°.$$

Here, $Y_{he}(s)$ represents the admittance of the coupled human and passive exoskeleton, which is overall passive. Hence, $\angle -Y_{he}(j\omega) \in [-90°, 90°] \ \forall \omega \geq 0$ There from Equation 44:

$$\angle -L_{he}(j\omega) \in [0°, 180°], \forall \omega \geq 0. \tag{45}$$

Where $\angle -L_{he}(j\omega) = 0$ for $\omega = 0$ and $\angle -L_{he}(j\omega) = 180°$ for $\omega = \infty$. From Equation 45, one may see that the phase of $-L_{he}(s)$ remains within 0° and 180°, and it reaches 180° when $\omega = \infty$. Therefore, the phase-crossover frequency $\omega_c$ of $-L_{he}(s)$ is:

$$\omega_c(-L_{he}) = \infty. \tag{46}$$

Using Equations 8, 10, 11, 39 and 41 in Equation 42, the loop gain transfer function $L_{he}(s)$ may be written as:

$$L_{he}(s) = \frac{I_h s^4 + (b_h + b_c)s^3 + (k_h + k_e)s^2}{I_h I_e s^4 + b_3 s^3 + b_2 s^2 + b_1 s + b_0}, \tag{47}$$

$$= \frac{I_h + \frac{b_h + b_c}{s} + \frac{k_h + k_c}{s^2}}{I_h I_e + \frac{b_3}{s} + \frac{b_2}{s^2} + \frac{b_1}{s^3} + \frac{b_0}{s^4}}$$

where

-continued $$b_0 = k_h k_c + k_h k_c + k_c k_e, \tag{48}$$

$$b_1 = b_h(k_c + k_e) + b_c(k_h + k_e) + b_e(k_h + k_e),$$

$$b_2 = I_h(k_c + k_e) + I_e(k_h + k_e) + b_h b_e + b_h b_c + b_c b_e,$$

$$b_3 = I_h(b_c + b_e) + I_e(b_h + b_c).$$

For $\omega = \infty$, $s = \infty$, and hence the loop transfer function at For $\omega = \infty$ from Equation 47 reduces to:

$$L_{he}(\infty) = \frac{1}{I_e}. \tag{49}$$

Therefore, from Equation 46 and 49, the gain margin of $-L_{he}(s)$ reduces to:

$$GM(-L_{he}) = I_e. \tag{50}$$

It should be noted that the gain margin in Equation 50 depends on the moment of inertia of the exoskeleton and is invariant to the parameters of the human joint and the coupling element. Therefore:

$$\text{Coupled System is:} \begin{cases} \text{Stable} & \text{if } K_\alpha < I_e(I_e^d > 0) \\ \text{Marginally Stable} & \text{if } K_\alpha = I_e(I_c^d = 0) \\ \text{Unstable} & \text{if } K_\alpha > I_e(I_c^d < 0) \end{cases} \tag{51}$$

Equation 51 indicates that for $K_\alpha > I_e$, the coupled human-exoskeleton system will be unstable irrespective of how stiff and damped the coupling between them is. Moreover, Equation 51 indicates that the desired emulated moment of inertia $I_e^d$ of the exoskeleton obtained from Equation 36 cannot be negative as desired. As shown in Equation 51, the exoskeleton with a soft coupling (irrespective of how stiff and damped the coupling is) cannot emulate a human joint dynamics with lower moment of inertia using positive feedback of joint acceleration.

Figure 22:
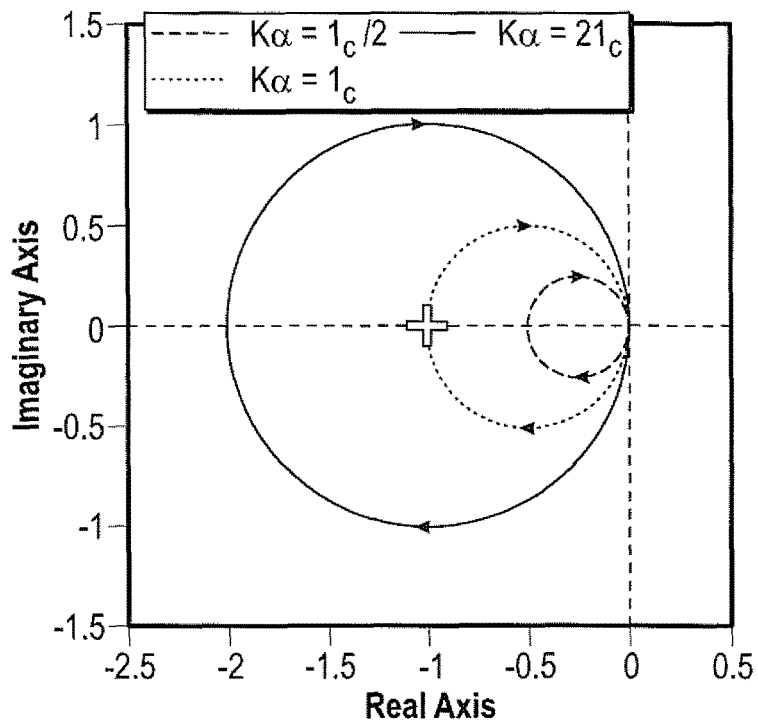
FIG. 22 is an illustrative graph of Nyquist diagrams of $-K_\alpha L_{he}(s)$ for different values of $K_\alpha$ in accordance with one aspect of the present application.

The Nyquist diagrams of $-K_\alpha L_{he}(s)$ for different values of $K_\alpha$ of a coupled system with the parameters listed in Table 1 are shown in FIG. 22. It can be seen from FIG. 22 that when $K_\alpha = 2I_e(>I_e)$, the Nyquist diagram encircles $-1+j0$ once in the clockwise direction, and hence results in an unstable closed-loop system, whereas when $K_\alpha = I_e/2(<I_e)$, the Nyquist diagram does not encircle $-1+j0$, and hence results in a stable closed-loop system. FIG. 22 also shows that when $K_\alpha = I_e$, the Nyquist diagram does not encircle $1+j0$ but passes through it resulting in a marginally stable closed-loop system, which is generally not desired either.

For any exoskeleton to effectively transmit torque/force to the human joint/limb, it may be necessary to have it coupled to the human limb as rigidly as possible, which may imply high coupling stiffness and high coupling damping $b_c$ as shown in Table 1. However, it may be important to note that irrespective of how stiff and damped the coupling is, the exoskeleton with soft coupling cannot emulate a human joint with moment of inertia lower than its nominal value using positive feedback of joint acceleration.

The above analysis shows that the coupled human-exoskeleton system's moment of inertia cannot be reduced below the human moment of inertia using positive acceleration feedback. However, this doesn't necessarily mean that inertia reduction cannot be achieved. One approach to achieve pure inertia reduction is shown below.

Figure 23A:
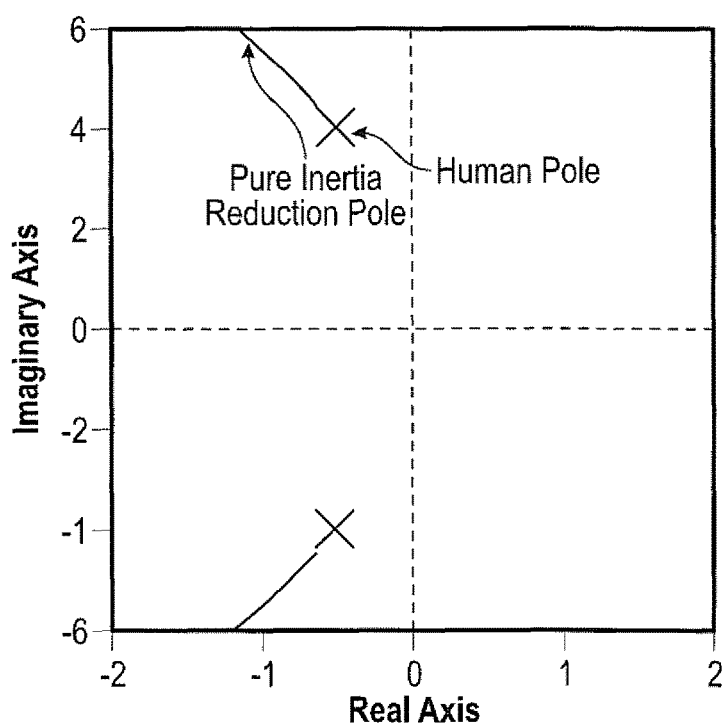
FIGS. 23A-23F are illustrative root locus plots of $-L_{he}(s)$ used to study the effect of adding low-pass Butterworth filters of different orders to the exoskeleton controller in accordance with one aspect of the present application.

The problem of achieving pure inertia reduction, i.e., reducing the moment of inertia of the human limb, while its joint damping and stiffness coefficients remain the same, can be formulated as a pole-placement problem. The primary bottleneck is to ensure coupled stability. It is important to note that the unassisted human joint dynamics in Equation 1 have two poles, whereas the coupled human-exoskeleton joint dynamics in Equations 4-6 have four poles. However, the coupled dynamics has two dominant poles and behaves predominantly like a second-order system. FIG. 23A shows the two poles corresponding to the unassisted human leg dynamics in the complex plane, whose parameters are shown in Table 1. It also shows the path along which those two poles will move when there is pure inertia reduction. Now, the goal of the exoskeleton control attempting to achieve pure inertia reduction is to place the dominant poles of the closed-loop dynamics of the coupled human and exoskeleton system anywhere on this path of pure inertia reduction poles.

Figure 23B:
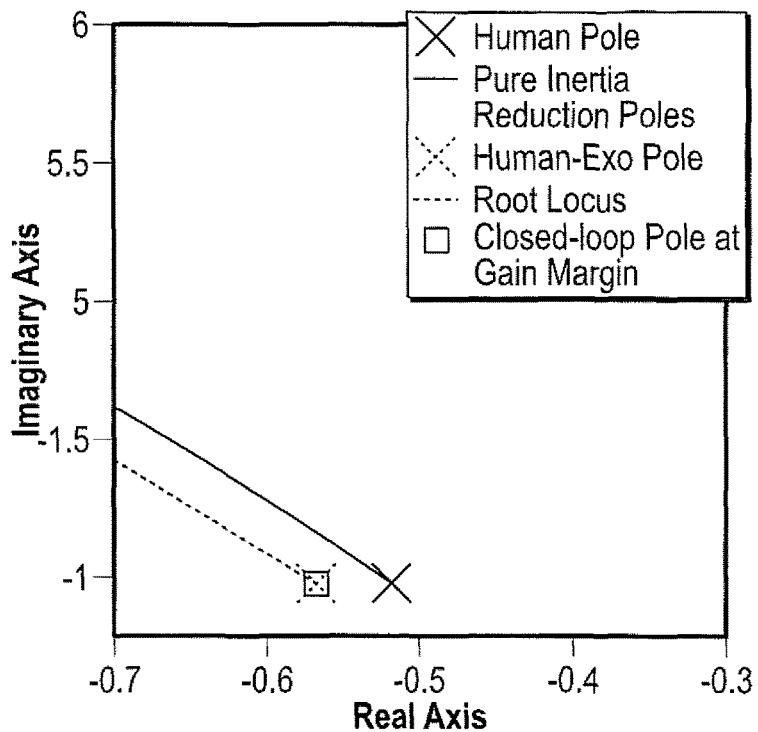
Figure 23C:
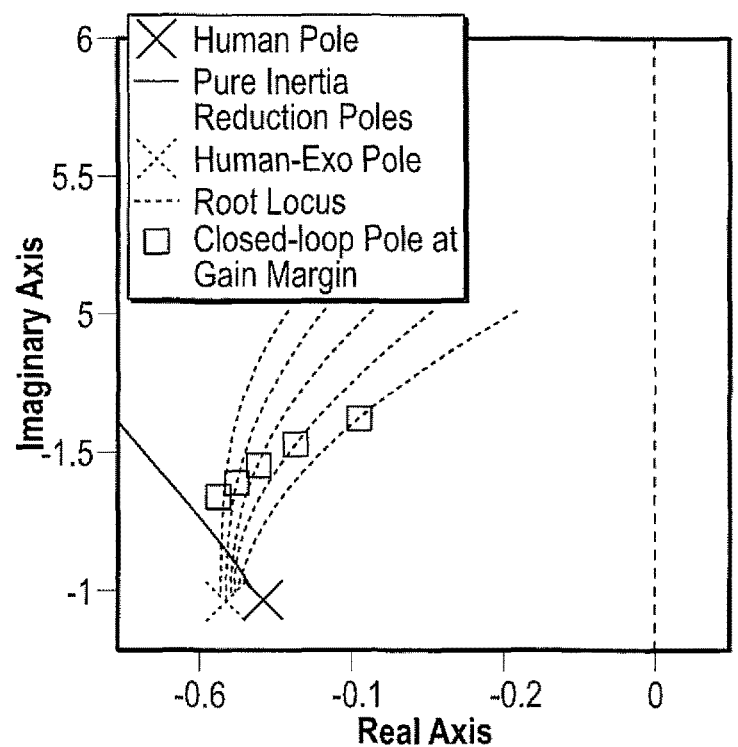
Figure 23D:
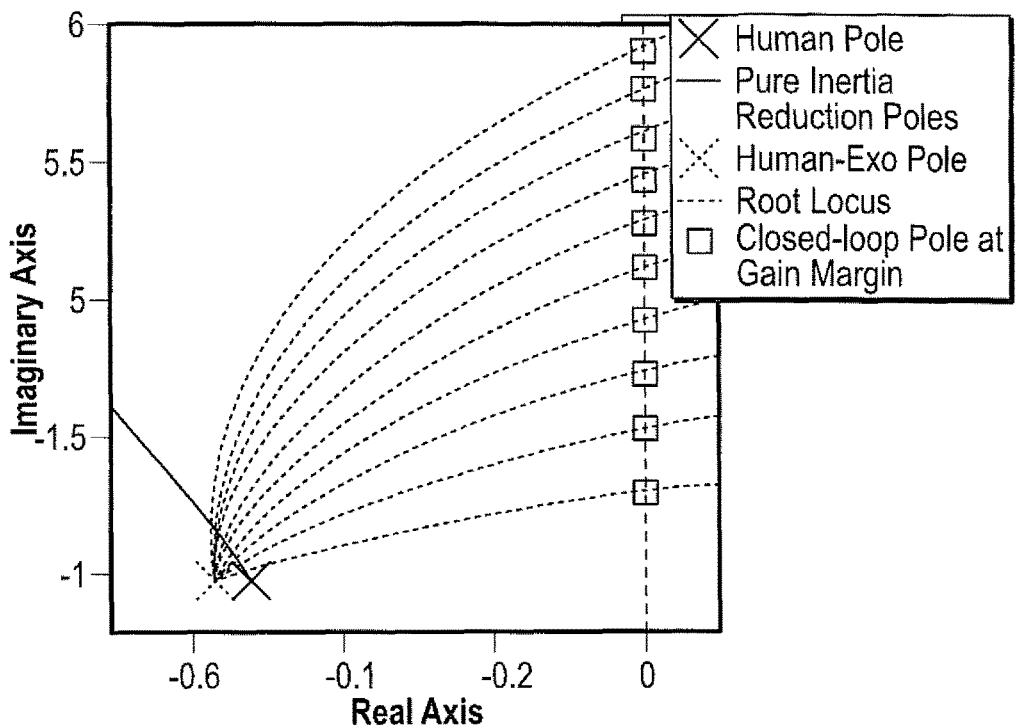
Figure 23E:
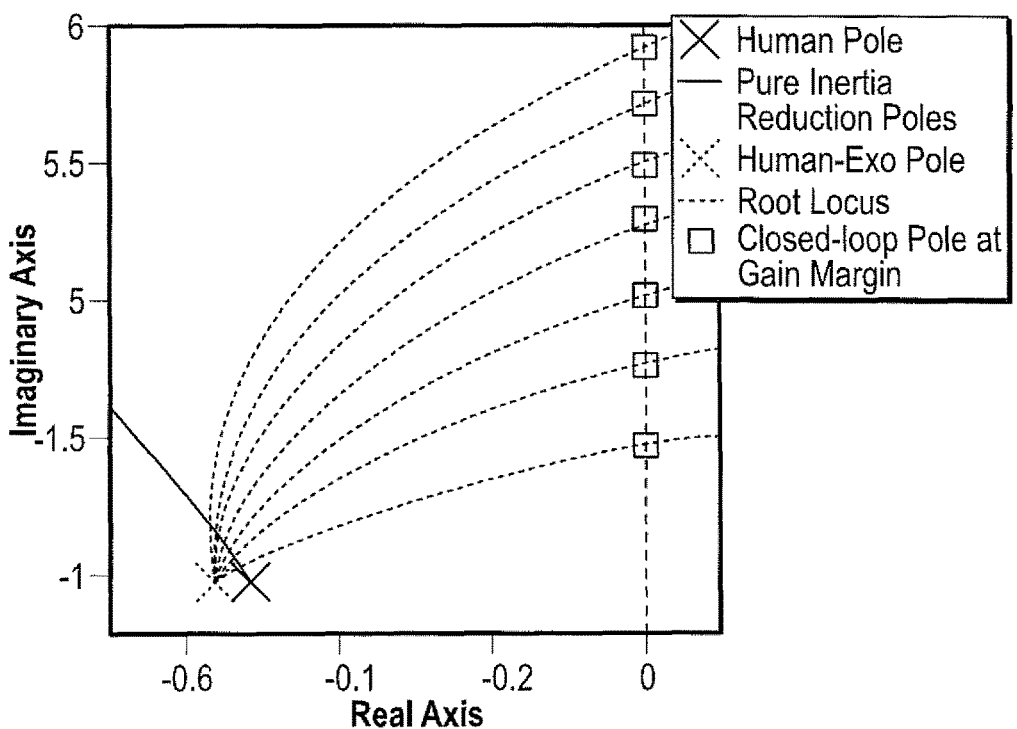
Figure 23F:
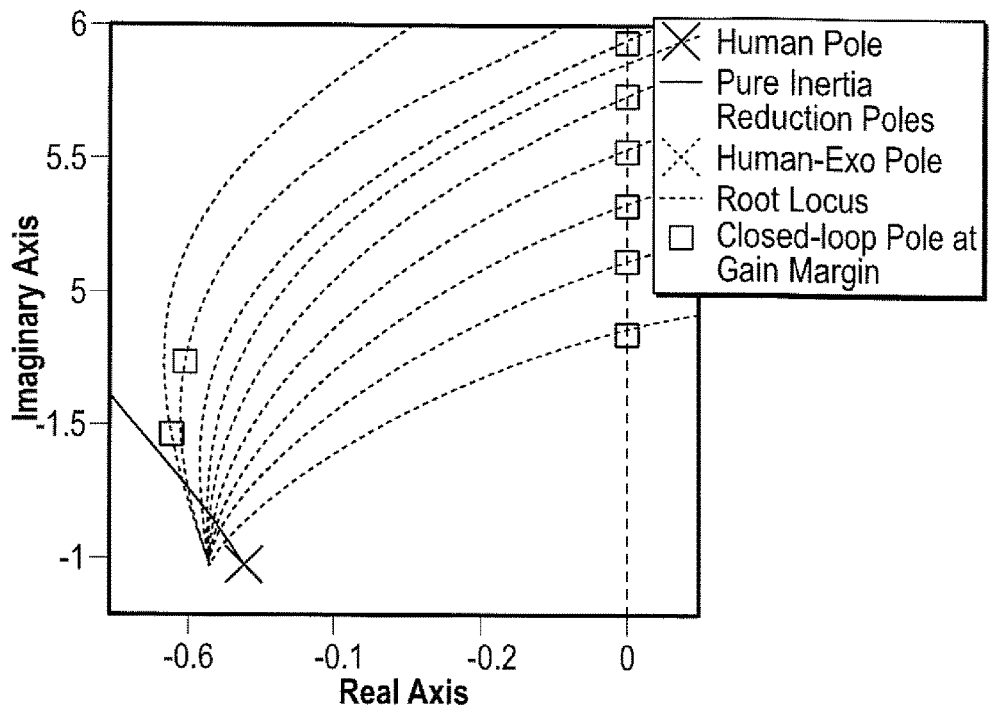

FIG. 23B shows a magnified view of the area in the complex plane around the dominant pole with positive imaginary part. It shows the open-loop pole of $-L_{he}(s)$, its root locus and the closed-loop pole at its gain margin. It may be seen that the root locus does not intersect the curve of desired poles, and moreover at gain margin, i.e., the gain at which the closed-loop system goes unstable, the closed-loop pole has not moved much and hence, does not produce any desired pure inertia reduction.

It is important to note that in this case, the root locus is fixed, and hence there is no available parameter to modify the root locus. Therefore, the way to modify the root locus so as to achieve reduced inertia is to add either poles or zeros to the system. From Equation 47, it may be seen that the loop transfer function $L_{he}(s)$ has a relative degree of zero, i.e., equal number of poles and zeros. If a zero is added to the loop transfer function, its relative degree will be negative, which will cause its frequency response magnitude to increase linearly with higher frequencies, which is not desired. Hence, only poles can be added to the loop transfer function $L_{he}(s)$. Adding poles is similar to using low-pass filters of different orders.

The effect of adding a low-pass Butterworth filter is shown below whose transfer function is given by:

$$H_{lo}(s) = \frac{\omega_{lo}^n}{\prod_{k=1}^{n}(s-s_k)}, \quad (52)$$

where n is the order of the filter, $\omega_{lo}$ is the cut-off angular frequency and $$s_k = \omega_{lo} e^{j\frac{(2k+n-1)\pi}{2n}}, \quad (53)$$

where $e^{jx} = \cos x + j \sin x$. It is important to note that the order of the filter is identical to the number of poles added, and irrespective of the order, the Butterworth filter has one tunable parameter $\omega_{lo}$. FIGS. 23C-23F show plots similar to FIG. 23B with Butterworth filters of orders n=1 to n=4 respectively for different cut-off frequencies $\omega_{lo}$. It may be seen that Butterworth filters of all orders considered here have multiple cut-off frequencies for which the non-zero pure inertia reduction may be achieved.

Figure 24:
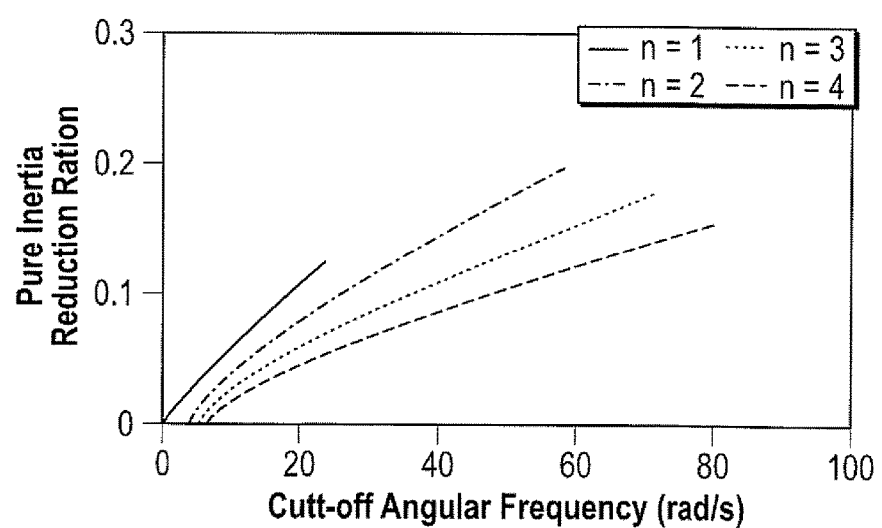
FIG. 24 are plots of achievable pure inertia reduction using low-pass Butterworth filters of the different orders n=1 to n=4 with increasing cut-off frequency $\omega_{lo}$.

The plots of achievable pure inertia reduction using the low-pass Butterworth filters of the different orders n=1 to n=4 with increasing cut-off frequency $\omega_{lo}$ are shown in FIG. 24. It may be seen that for low-pass filters of order n=1 to n=4, there exists a range of cut-off frequencies for which non-zero pure inertia reduction may be achieved, and the achievable inertia reduction increases with cut-off frequency until it reaches its maximum. It should be noted that coupled stability may limit the amount of achievable inertia reduction. FIG. 24 shows that the second-order low-pass filter achieves the maximum possible pure inertia reduction, and hence is chosen for the exoskeleton control law in Equation 31.

While embodiments of the disclosure have been described in terms of various specific embodiments, those skilled in the art will recognize that the embodiments of the disclosure may be practiced with modifications within the spirit and scope of the claims.

What is claimed is:

1. An assistive exoskeleton control system comprising:
a controller configured to:
generate a positive assistance for a coupled human exoskeleton system by shaping a closed loop integral admittance of the coupled human exoskeleton system to a desired assistance ratio $A_d$ by modifying a control transfer function using a cut-off frequency of a low pass filter; and
optimize the desired assistance ratio $A_d$ by minimizing an optimization equation defined by: $|A-A_d|+\omega R$ wherein A is an assistance ratio over a desired frequency range and R is a resistance ratio over the desired frequency range.

2. The assistive exoskeleton control system of claim 1, wherein the controller is further configured to modify feedback gains on angular acceleration using the cut-off frequency of the low pass filter.

3. The assistive exoskeleton control system of claim 1, wherein the low pass filter is a Butterworth low-pass filter.

4. The assistive exoskeleton control system of claim 1, wherein the control transfer function is defined by:

$$U_c(s) = \frac{K_\alpha H_{lo}(s)s^2 + K_\omega s + K_\theta}{s}$$

where $K_\alpha = I_? - I_?^d$, $K_? = b_? - b_?^d$ and $K_{\theta=k?} - k_?^d$ are feedback gains on an angular acceleration $\ddot{\theta}$, angular velocity $\dot{\theta}$ and angle $\theta$ respectively and $H_{lo}(s)$ is a second-order Butterworth low-pass filter defined by:

$$H_{lo}(s) = \frac{\omega_{lo}^2}{s^2\sqrt{2}\,\omega_{lo}s + \omega_{lo}^2}$$

where $\omega_{lo}$ is the cut-off frequency of the second-order Butterworth low-pass filter.

5. The assistive exoskeleton control system of claim 1, wherein the assistance ratio is defined by:

$$\mathcal{A} = \frac{1}{\omega_f}\int_o^{\omega_f} \mathcal{AF}(\omega)d\omega \text{ wherein} \quad (19)$$

-continued $$\mathcal{AF}(\omega) = \begin{cases} \frac{|X_{heu}(j\omega)| - |X_h(j\omega)|}{|X_h(j\omega)|} & \text{if } |X_{heu}(j\omega)| \geq |X_h(j\omega)| \\ 0 & \text{if } |X_{heu}(j\omega)| < |X_h(j\omega)| \end{cases}$$

where $X_h(j\omega)$ is the integral admittance of a human joint and $X_{heu}(j\omega)$ is the integral admittance of a coupled human-exoskeleton system.

6. The assistive exoskeleton control system of claim 1, wherein the resistance ratio is defined by:

$$R = \frac{1}{\omega f} \int_o^{\omega f} \mathcal{RF}(\omega) d\omega \text{ wherein} \quad (19)$$

$$RF(\omega) = \begin{cases} 0 & \text{if } |X_{heu}(j\omega)| \geq |X_h(j\omega)| \\ \frac{|X_h(j\omega)| - X_{heu}(j\omega)|}{|X_h(j\omega)|} & \text{if } |X_{heu}(j\omega)| < |X_h(j\omega)| \end{cases}$$

where $X_h(j\omega)$ is the integral admittance of a human joint and $X_{heu}(j\omega)$ is the integral admittance of a coupled human-exoskeleton system.

7. The assistive exoskeleton control system of claim 1, wherein the controller is further configured to control a damping ratio of the coupled human-exoskeleton system and an unassisted human joint to a desired value.

8. The assistive exoskeleton control system of claim 1, wherein the controller is further configured to control a damping ratio defined by: $|\zeta_{heu} - \zeta_h|/|\zeta_h| < \epsilon$, where $\zeta_{heu}$ is a damping ratio of the coupled human-exoskeleton system, $\zeta_h$ is a damping ratio of an unassisted human joint and c is a desired variation in the damping ratio of human joint dynamics.

9. The assistive exoskeleton control system of claim 1, wherein the controller has a gain margin greater than 1.

10. The assistive exoskeleton control system of claim 1, wherein the controller has coupled passivity.

11. The resistive exoskeleton control system of claim 10, wherein a phase of the closed loop integral admittance is defined by: $X_{heu}'(j\omega) \in [-180°, 0°] \forall \omega$.

12. An assistive exoskeleton control system comprising:
a controller generating a positive assistance for a coupled human exoskeleton system by shaping a closed loop integral admittance of the coupled human exoskeleton system, wherein a frequency response magnitude of the closed loop integral admittance is greater than that of a natural human joint, wherein the controller generating a control transfer function defined by:

$$U_c(s) = \frac{K_\alpha H_{lo}(s) s^2 + K_\omega s + K_\theta}{s}$$

where $K_\alpha = I_? - I_?^d$, $K_? = b_? - b_?^d$ and $K_\theta = k_? - k_?^d$ are feedback gains on angular acceleration $\ddot{\theta}$, angular velocity $\dot{\theta}$ and angle $\theta$ respectively and $H_{lo}(s)$ is a second-order Butterworth low-pass filter defined by:

$$H_{lo}(s) = \frac{\omega_{lo}^2}{s^2 \sqrt{2} \omega_{lo} s + \omega_{lo}^2}$$

where $\omega_{lo}$ is a cut-off frequency of the second-order Butterworth low-pass filter.

13. The assistive exoskeleton control system of claim 12, wherein the controller is further configured to optimize a desired assistance ratio $A_d$ by minimizing an optimization equation defined by: $|A-A_d|+\omega R$ herein A is an assistance ratio over a desired frequency range and R is a resistance ratio over the desired frequency range.

14. The assistive exoskeleton control system of claim 13, wherein the assistance ratio is defined by::

$$\mathcal{A} = \frac{1}{\omega_f} \int_o^{\omega_f} \mathcal{AF}(\omega) d\omega \text{ wherein} \quad (20)$$

$$AF(\omega) = \begin{cases} \frac{|X_{heu}(j\omega)| - |X_h(j\omega)|}{|X_h(j\omega)|} & \text{if } |X_{heu}(j\omega)| \geq |X_h(j\omega)| \\ 0 & \text{if } |X_{heu}(j\omega)| < |X_h(j\omega)| \end{cases}$$

where $X_h(j\omega)$ is the integral admittance of a human joint and $X_{heu}(j\omega)$ is the integral admittance of a coupled human-exoskeleton system.

15. The assistive exoskeleton control system of claim 13, wherein the resistance ratio is defined by:

$$R = \frac{1}{\omega f} \int_o^{\omega f} RF(\omega) d\omega \text{ wherein} \quad (19)$$

$$RF(\omega) = \begin{cases} 0 & \text{if } |X_{heu}(j\omega)| \geq |X_h(j\omega)| \\ \frac{|X_h(j\omega)| - X_{heu}(j\omega)|}{|X_h(j\omega)|} & \text{if } |X_{heu}(j\omega)| < |X_h(j\omega)| \end{cases}$$

where $X_h(j\omega)$ is the integral admittance of a human joint and $X_{heu}(j\omega)$ is the integral admittance of coupled human-exoskeleton system.

16. The assistive exoskeleton control system of claim 12, wherein the controller is further configured to control a damping ratio defined by: $|\zeta_{heu} - \zeta_h|/|\zeta_h| < \epsilon$, where $\zeta_{heu}$ is a damping ratio of the coupled human-exoskeleton system, $\zeta_h$ is a damping ratio of an unassisted human joint and $\epsilon$ is a desired variation in the damping ratio of human joint dynamics.

17. The assistive exoskeleton control system of claim 11, wherein the controller has a gain margin greater than 1 and wherein a phase of the closed loop integral admittance is defined by $X_{heu}'(j\omega) \in [-180°, 0°] \forall \omega$.

18. An assistive exoskeleton control system comprising:
a controller configured to:
generate a positive assistance for a coupled human exoskeleton system by shaping closed loop integral admittance of a coupled human exoskeleton system to a desired assistance ratio $A_d$ by generating a control transfer function defined by:

$$U_c(s) = \frac{K_\alpha H_{lo}(s) s^2 + K_\omega s + K_\theta}{s}$$

where $K_\alpha = I_? - I_?^d$, $K_? = b_? - b_?^d$ and $K_\theta = k_? - k_?^d$ are the feedback gains on angular acceleration $\ddot{\theta}$, angular velocity $\dot{\theta}$ and angle $\theta$ respectively and $H_{lo}(s)$ is a second-order Butterworth low-pass filter defined by:

$$H_{lo}(s) = \frac{\omega_{lo}^2}{s^2 + \sqrt{2} \omega_{lo} s + \omega_{lo}^2},$$

wherein $\omega_{lo}$ is a cut-off frequency of the second-order Butterworth low-pass filter;

optimize the desired assistance ratio $A_d$ by minimizing an optimization equation defined by: $|A-A_d|^2+\omega R$, wherein A is an assistance ratio over a desired frequency range and R is a resistance ratio over the desired frequency range; and control a damping ratio defined by: $|\zeta_{heu}-\zeta_h|/|\zeta_h|<\epsilon$, where $\zeta_{heu}$ is a damping ratio of the coupled human-exoskeleton system, $\zeta_h$ is a damping ratio of an unassisted human joint and $\epsilon$ is a desired variation in the damping ratio of human joint dynamics, the controller being stable and passive.

19. The assistive exoskeleton control system of claim 18, wherein the assistance ratio is defined by:

$$\mathcal{A} = \frac{1}{\omega_f}\int_o^{\omega_f} \mathcal{AF}(\omega)d\omega \text{ wherein} \tag{20}$$

$$AF(\omega) = \begin{cases} \frac{|X_{heu}(j\omega)| - |X_h(j\omega)|}{|X_h(j\omega)|} & \text{if } |X_{heu}(j\omega)| \geq |X_h(j\omega)| \\ 0 & \text{if } |X_{heu}(j\omega)| < |X_h(j\omega)| \end{cases}$$

where $X_h(j\omega)$ is the integral admittance of a human joint and $X_{heu}(j\omega)$ is the integral admittance of a coupled human-exoskeleton system and the resistance ratio is defined by:

$$R = \frac{1}{\omega f}\int_o^{\omega f} RF(\omega)d\omega \text{ wherein} \tag{19}$$

$$RF(\omega) = \begin{cases} 0 & \text{if } |X_{heu}(j\omega)| \geq |X_h(j\omega)| \\ \frac{|X_h(j\omega)| - X_{heu}(j\omega)|}{|X_h(j\omega)|} & \text{if } |X_{heu}(j\omega)| < |X_h(j\omega)| \end{cases}.$$

\* \* \* \* \*